(12) United States Patent
Falco et al.

(10) Patent No.: US 7,026,527 B2
(45) Date of Patent: Apr. 11, 2006

(54) PLANT METHIONINE SYNTHASE GENE AND METHODS FOR INCREASING THE METHIONINE CONTENT OF THE SEEDS OF PLANTS

(75) Inventors: Saverio Carl Falco, Arden, DE (US); Omolayo O. Famodu, Newark, DE (US); Jan Antoni Rafalski, Wilmington, DE (US); Michael Lee Ramaker, Greenville, DE (US); Mitchell Christian Tarczynski, West Des Moines, IA (US); Catherine Thorpe, Cambridgeshire (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 345 days.

(21) Appl. No.: 09/989,339

(22) Filed: Jan. 28, 2002

(65) Prior Publication Data
US 2003/0088886 A1 May 8, 2003

Related U.S. Application Data

(63) Continuation of application No. 09/377,431, filed on Aug. 19, 1999, now abandoned, which is a continuation-in-part of application No. 08/703,829, filed on Aug. 27, 1996, now abandoned.
(60) Provisional application No. 60/002,973, filed on Aug. 30, 1995.

(51) Int. Cl.
| | |
|---|---|
| A01H 1/00 | (2006.01) |
| A01H 4/00 | (2006.01) |
| C12N 15/82 | (2006.01) |
| C12N 5/10 | (2006.01) |
| C07H 21/04 | (2006.01) |

(52) U.S. Cl. .............. 800/278; 435/320.1; 435/468; 435/410; 435/419; 435/69.1; 435/183; 536/23.1; 536/23.2; 536/23.4; 536/23.6; 536/24.1; 800/281; 800/290; 800/295; 800/298

(58) Field of Classification Search .............. 435/320.1, 435/468, 410, 419, 69.1, 183; 536/23.1, 23.2, 536/23.4, 23.6, 24.1; 800/278, 281, 290, 800/295, 298
See application file for complete search history.

(56) References Cited

U.S. PATENT DOCUMENTS 5,912,414 A    6/1999    Falco et al.

OTHER PUBLICATIONS

Phillips, R.L. et al., Elevated Protein–Bound Methionine in Seeds of a Maize Line Resistant to Lysine Plus Threonine, *American Assoication of Cereral Chemist, In.c*, 62(3), 213–218, 1985.

Madison, James T. et al., Characterization of soybean tissue culture cell lines resistant to methionine analogs, *Plant Cell Reports*, 7, 473–476, 1988.

Giovanelli, John et al., In Vivo Regulation of De Novo Methionine Biosynthesis in a Higher Plant (*Lemna*), *Plant Physiol.*, 77, 450–455, 1985.

Eichel, Johannes et al., Vitamin–B$_{12}$–independent methionine synthase from a higher plant (*Catharanthus roseus*)— Molecular characterization, regulation, heterologous expression, and enzyme properties, *Eur. J. Biochem.*, 230, 1053–1058, 1995.

Peterson, Maike et al., Plant Gene Register PGR95–049— Full–length cDNA clone from *Coleus blumei* (Accession No. Z49150) with high similarity to cobalamine–independent methionine synthease (1), *Plant Physiol.*, 109, 338, 1995.

Ravanel, Stephane et al., The specific features of methionine biosynthesis and metabolism in plants, *Proc. Natl. Acad. Sci. USA*, 95, 7805–7812, Jun. 1998.

Yamada, Yazuhiro et al., Cloning, Sequencing, and Heterologous Expression of Rat Methionine Synthase cDNA, *Biosci. Biotechnol. Biochem*, 62(11): 2155–2160, 1998.

Thompson, Gregory A. et al., Methionine Biosynthesis in *Lemna*, *Plant Physiol.*, 69, 1077–1083, 1982.

Le Guen, L. et al., Gene density and organization in a small region of the *Arabidopsis thaliana* genome, *Mol. Gen. Genet.*, 245, 390–396, 1994.

*Primary Examiner*—David Guzo

(57) ABSTRACT

This invention relates to a nucleic acid fragment encoding a plant 5-methyltetra-hydropteroyltriglutamate-homocysteine methyltransferase or methionine synthase. The invention also includes chimeric genes, a first encoding a plant methionine synthase (MS) gene, a second encoding a plant cystathionine γ-synthase (CS) gene, a third encoding feedback-insensitive aspartokinase (AK) or bifunctional feedback-insensitive aspartokinase-homoserine dehydrogenase (AK-HDH), which is operably linked to a plant chloroplast transit sequence, and a fourth encoding a methionine-rich protein, all operably linked to plant seed-specific regulatory sequences. Methods for their use to produce increased levels of methionine in the seeds of transformed plants are provided.

15 Claims, 9 Drawing Sheets

Figure 1: MS alignment

```
                    1                                                           60
E. coli MS          MTILNHTLGFPRVGLRRELKKAQESYWAGNSTREELLAVGRELRARHWDQQKQAGIDLLP
yeast MS            MVQ.SAVLGFPRIGPNRELKKATEGYWNGKITVDELFKVGKDLRTQNWKLQKEAGVDIIP
tobacco MS          MA..SHIVGYPRMGPKRELKFALESFWDGKSSAEDLKKVAADLRSSIWKQMADAGIKYIP
C. roseus MS        MA..SHIVGYPRMGPKRELKFALESFWDKKSSAEDLQKVAADLRSSIWKQMADAGIKYIP
corn MS/partial     ............................................................
soy MS/partial      ............................................................

61                                                          120
E. coli MS          VGDFAWYDHVLTTSLLLGNVPARHQN.KDGSVDIDTLFRIGRG..RAPTGE...PAAAA
yeast MS            SNDFSFYDQVLDLSLLFNVIPDRYTKYDLSPI..DTLFAMGRGLQRKATETEKAVDVTAL
tobacco MS          XNTFSYYDQVLDTTAMLGAVPARY.NWAGGEIAFDTYFSMARG..........NXSVPAM
C. roseus MS        SNTFSYYDQVLDTATMLGAVPPRY.NFAGGEIGFDTYFSMARG...........NASVPAM
corn MS/partial     ............................................................
soy MS/partial      ............................................................

121                                                         180
E. coli MS          EMTKWFNTNYHYMVPEFVKGQQFKLTWTQLLDEVDEALALGHKVKPVLLGPVTWLWLGKV
yeast MS            EMVKWFDSNYHYVRPTFSKTTQFKLNGQKPVDEFLEAKELGIHTRPVLLGPVSYLFLGKA
tobacco MS          EMTKWXDTNYHFIVPELGPDVNFSYASHKAVDEYKEAKGLGVDTVPVLIGPVSYLLLSKP
C. roseus MS        EMTKWFDTNYHYIVPELGPEVNFSYASHKAVNEYKEAKELGVDTVPVLVGPVTFLLLSKP
corn MS/partial     ............................................................
soy MS/partial      ............................................................

181                                                         240
E. coli MS          .KGEQ..FDRLSLLNDILPVYQQVLAELAKRGIEWVQIDEPALVLELPQAWLDAYKPAYD
yeast MS            DKDSLDLEPL.SLLEQLLPLYTEILSKLASAGATEVQIDEPVLVLDLPANAQAAIKKAYT
tobacco MS          AKGVEKSFPLLSLLDKVLPIYKEVIAELKAAGASWIQFDEPTLVLDLQAHQLEAFTKAYA
C. roseus MS        AKGVEKTFPLLSLLDKILPVYKEVIGELKAAGASWIQFDEPTLVLDLESHQLEAFTKAYS
corn MS/partial     ............................................................
soy MS/partial      ............................................................
```

FIGURE 1 CONTINUED

```
                 241                                                          300
E. coli MS       ALQGQV...KLLLTTYFEGVTPN....LDTITALPVQGLHVDLVHGKDDVAELHKRLPSD
yeast MS         YFGEQSNLPKITLATYFGTVVPN....LDAIKGLPVAALHVDFVRAPEQFDEVVAAIGNK
tobacco MS       ELESSLSGLNVLTETYFADVPAEAFKTLTALKG..VTAFGFDLVRGAQTLDLIKGGFPSG
C. roseus MS     ELESTLSGLNVIVETYFADIPAETYKILTALKG..VTGFGFDLVRGAKTLDLIKGGFPSG
corn MS/partial  ............................................................
soy MS/partial   ............................................................

301                                                          360
E. coli MS       WLLSAGLINGRNVWRADLTEKYAQIK...DIVGKRDLWVASSCSLLHSPIDLSVETRLDA
yeast MS         QTLSVGIVDGRNIWKNDFKKSSAIVNKAIEKLGADRVVATSSSLLHTPVDLNNETKLDA
tobacco MS       KYLFAGVVDGRNIWANDLAASLNLLQSLEGIVGKDKLVVSTSCSLLHTAVDLVNETKLDD
C. roseus MS     KYLFAGVVDGRNIWANDLAASLSTLQSLEGIVGKDKLVVSTSCSLLHTAVDLVNEPKLDK
corn MS/partial  ............................................................
soy MS/partial   ............................................................

361                                                          420
E. coli MS       EVKSWFAFALQKCHELALLRDALNSGDTAA.LAEWSAPIQARRHSTRVHNPAVEKRLAAI
yeast MS         EIKGFFSFATQKLDEVVITKNVSGQDVAAALEANAKSVESRGKSKFIHDAAVKRRVASI
tobacco MS       EIKSWLAFAAQKVVEVNALAKALAXHKDEAFFSANATAQASRKSSPRVTNEAVQKAAAAL
C. roseus MS     EIKSWLAFAAQKVVEVNALAKALAGEKDEAFFSENAAAQASRKSSPRVTNQAVQKAAAAL
corn MS/partial  ...........FAAQKVVEVNALAKALSGQKDEVFFSANAAALASRKSSPRVINEAVQKAAAAL
soy MS/partial   ............................................................

421                                                          480
E. coli MS       TAQDSQRANVYEVRAEAQRARFKLPAWPTTTIGSFPQTTEIRTLRLDFKKGNLDANNYRT
yeast MS         DEKMSTRAAPFEQRLPEQQKVFNLPLFPTTTIGSFPQTKDIRINRNKFNKGTISAEEYEK
tobacco MS       KGSDHRRATNVSSRLDAQQKKLNLPVLPTTIGSFPQTVELRVRREYKAKKISEEEYVK
C. roseus MS     RGSDHRRATTVSARLDAQQKKLNLPVLPTTIGSFPQTLELRRVRREYKAKKISEDDYVK
corn MS/partial  ...................................................VTXGEXIS
soy MS/partial   KGSDHRRATNVSARLDAQQKKLNLSVLPTTTIGSFPQTADLRRVRREFKANKISEEEYVK
```

FIGURE 1 CONTINUED

```
                    481                                                                          540
E. coli MS          GIAEHIKQAIVEQERLGLDVLVHGEAERNDMVEYFGEHLDGFVFTQNGWVQSYGSRCVKP
yeast MS            FINSEIEKVIRFQEEIGLDVLVHGEPERNDMVQYFGEQINGYAFTVNGWVQSYGSRYVRP
tobacco MS          AIKAEIKKVVDLQEELDIDVLVHGEPERNDMVEYFGEQLSGFAFTANGWVQSYGSRCVKP
C. roseus MS        AIKEEISKVVKLQEELDIDVLVHGEPERNDMVEYFGEQLSGFAFTANGWVQSYGSRCVKP
corn MS/partial     AIMEXISKXVRIQELDIDVVHGEPERXDXXXYFGEXLSAFASTATGWXXSYGSR....
soy MS/partial      SIKEEIRKVVELQEELDIDVLVHGEPERNDMVEYFGEQLSGFAFTVNGWVQSYGSRCVKP 541                                                                          600
E. coli MS          PIVIGDISRPAPITVEWAKYAQSLTDKPVKGMLTGPVTILCWSFPREDVSRETIAKQIAL
yeast MS            PIIVGDLSRPKAMSVKESVYAQSITSKPVKGMLTGPITCLRWSFPRDDVDQKTQAMQLAL
tobacco MS          PIIYGDVSRPNPMTVFWSKTAQSMTKRPMKGMLTGPVTILNWSFVRNDQPRXETCYQIAX
C. roseus MS        PIIYGDVSRPNPMTVFWSQTAQSMTKRPMKGMLTGPVTILNWSFVRNDQPRFETCYQIAL
corn MS/partial     ..........PIIYGDVSRPKPMTVFWSSLAQSFTKRPMKGMLTGPVTILNWXFVRNDQPRSETTYQIAL
soy MS/partial      PIIYGDVSRPKPMTVFWSSLAQSFTKRPMKGMLTGPVTILNWSFVRNDQPRSETTYQIAL 601                                                                          660
E. coli MS          ACVMKWPIWKPLELASSRLTNRRLRQGLPLRRS..DWDAYLQWGVEAFRINAAVAKDDTQI
yeast MS            ALRDEVNDLEAAGIKVIQVDEPALREGLPLREGTERSAYYTWAAEAFRVATSGVANKTQI
tobacco MS          XIKDEVEDLEKAXITVIQIDEAALREGLPLRKA.EHAFYLNWAVHSFRITNVGIQDTTQI
C. roseus MS        AIKDEVEDLEKAGINVIQIDEAALREGLPLRKA.EHAFYLDWAVHSFRITNLPLQDTTQI
corn MS/partial     .............................................................
soy MS/partial      AIKDEVEDLEKAGITVIQIDEAALREGLPLXKS.EQAHYLDWAVHAFRITNVGVQDTTQI 661                                                                          720
E. coli MS          HTHMCYCEFNDIMDSIAALDRDVITIE.TSRSDMELLESFEE.FDYPNEIGPGVYDIHSP
yeast MS            HSHFCYSDLDP..NHIKALDADVVSIEFSKKDDANYIAEFKN...YPNHIGLGLFDIHSP
tobacco MS          HTHMCYSNFNDIIHSIIDMDADVITIE.NSRSDEKLLSVFREGVKYGAGIGPGVYDIHSP
C. roseus MS        HTHMCYSNFNDIIHSIIDMDADVMTIE.NSRSSEKLLSVFREGVKYGAGIGPGVYDIHSP
corn MS/partial     .............................................................
soy MS/partial      HTHMCYSNFNDIIHSIIDMDADVITIE.NSRSDEKLLSVFREGVKYGAGIXPGVYDIHSP
```

FIGURE 1 CONTINUED

```
                    721                                                           780
E. coli MS         NVPSVEWIEALLKKAAKRIPAERLWVNPDCGLKTRGWPETRAALANMVQAAQNLRRG...
yeast MS           RIPSKDEFIAKISTILKSYPAEKFWVNPDCGLKTRGWEETRLSLTHMVEAAKYFREQY..
tobacco MS         RIPSTEEIADRVNKMLAVLDTNILWVNPDCGLKTRKYAEVKPALENMVSAAKAIRTQLAS
C. roseus MS       RIPSTEEIADRINKMLAVLDTNILWVNPDCGLKTRKYAEVKPALENMVSAAKLIRTQLAS
corn MS/partial    ............................................................
soy MS/partial     RIPPTEEIADRINKMLAVLEKNILWVNPDCGLKTRKYTEVKPALTNMVAAAKLIRNELAK 781
E. coli MS         ...
yeast MS           KN.
tobacco MS         SK.
C. roseus MS       AK.
corn MS/partial    ...
```

FIGURE 2

```
SEQ ID NO:02   ****************************************************************
SEQ ID NO:04   MASHIVGYPRMGPKRELKFALESFWDGKSSAEDLEKVATDLRSSIWKQMSEAGIKYIPSN
SEQ ID NO:06   MASHIVGYPRMGPKRELKFALESFWDGKSSAEDLQKVAADLRSSIWKQMAGAGIKYIPSN
SEQ ID NO:08   MASHIVGYPRMGPKRELKFALESFWDGKSSAEDLKKVAADLRSSIWKQMADAGIKYIPSN
SEQ ID NO:10   MASHIVGYPRMGPKRELKFALESFWDGKSSAEDLEKVAADLRASIWKQMSEAGIKYIPSN
SEQ ID NO:11   MASHIVGYPRMGPKRELKFALESFWDKKSSAEDLQKVAADLRSSIWKQMADAGIKYIPSN
                                                                            60
                                                                             1

SEQ ID NO:02   ****************************************************************
SEQ ID NO:04   TSSYYDQVLDTTAMLGAVPERYSWTGGEIGLSTYFSMARGNATVPAMEMTKWFDTNYHFI
SEQ ID NO:06   TFSFYDQLLDATATLGAVPPRYGWTGGEIGFDTYFSMARGNATVPAMEMTKWFDTNYHFI
SEQ ID NO:08   TFSYYDQVLDTTAMLGAVPARYNWAGGEIAFDTYFSMARGNASVPAMEMTKWFDTNYHFI
SEQ ID NO:10   TFSYYDQVLDTTAMLGAVPDRYSWTGGEIGHSTYFSMXKGNATVPAMEMTKWFDTNXHFX
SEQ ID NO:11   TFSYYDQVLDTATMLGAVPPRYNFAGGEIGFDTYFSMARGNASVPAMEMTKWFDTNYHYI
                                                                           120
                                                                            61

SEQ ID NO:02   ****************************************************************
SEQ ID NO:04   VPELGPSTKFTYASHKAVSEYKEAKALGIDTVPVLVGPVSYLLLSKPAKGVEKSFSLLSL
SEQ ID NO:06   VPELGPDVNFTXASQKAVDEYKEAKAVDEYKEAKGLGVDTIPVLVGPVTYLLLSKPAKGVEKSFLLSL
SEQ ID NO:08   VPELGPDVNFSYASHKAVDEYKEAKGLGVDTVPVLIGPVSYLLLSKPAKGVEKSFPLLSL
SEQ ID NO:10   VPEL--------------------------------------------------------
SEQ ID NO:11   VPELGPEVNFSYASHKAVNEYKEAKELGVDTVPVLVGPVTFLLLSKPAKGVEKTFPLLSL
                                                                           180
                                                                           121
```

FIGURE 2 CONTINUED

```
              *    ****  ****  ********   ***      **   *  *  *  **   *  *  **
SEQ ID NO:02  LGSILPIYKEVVAELKAAGASWIQLDEPTLVKDLDAHELAAFSSAYAELESSFSGLNVLI
SEQ ID NO:04  LPKVLAVYKEVIADLKAAGASWIQFDEPTLVLDLESHKLQAFTDAYAELAPALSDLNVLV
SEQ ID NO:06  LDKVLPIYKEVIAELKAAGASWIQFDEPTLVLDQAHQLEAFTKAYAELESSLSGLNVLT
SEQ ID NO:08  ------------------------------------------------------------
SEQ ID NO:10  ------------------------------------------------------------
SEQ ID NO:11  LDKILPVYKEVIGELKAAGASWIQFDEPTLVLDLESHQLEAFTKAYSELESTLSGLNVIV
                                                                         240

******  ***  *   ***    *    ********  **   ***********
SEQ ID NO:02  ETYFADIPAESYKTLTSLSGVTAYGFDLIRGAKTLDLIRSSFPSGKYLFAGVVDGRNIWA
SEQ ID NO:04  ETYFADIPAEAYKTLTSLNGVTAYGFDLVRGTHTLDLIKGGFPSGKYLFAGVVDGRNIWA
SEQ ID NO:06  ETYFADVPAEAFKTLTALKGVTAFGFDLVRGAQTLDLIKGGFPSGKYLFAGVVDGRNIWA
SEQ ID NO:08  ------------------------------------------------------------
SEQ ID NO:10  ------------------------------------------------------------
SEQ ID NO:11  ETYFADIPAETYKILTALKGVTGFGFEDLVRGAKTLDLIKGGFPSGKYLFAGVVDGRNIWA
              181                                                        300

******   *  **   ******** ******************   ***********
SEQ ID NO:02  DDLAASLSTLHSLEAVAGKDKLVVSTSCSLMHTAVDLVNETKLDDEIKSWLAFAAQKVVE
SEQ ID NO:04  NDLAASLTTLQGLEGIVGKDKLVVSTSSLLHTAVDLVNETKLDDEIKSWLAFAAQKIVE
SEQ ID NO:06  NDLAASLNLLQSLEGIVGKDKLVVSTSCSLLHTAVDLVNETKLDDEIKSWLAFAAQKVVE
SEQ ID NO:08  ------------------------------------------------------------
SEQ ID NO:10  ------------------------------------------------------------
SEQ ID NO:11  NDLAASLSTLQSLEGIVGKDKLVVSTSCSLLHTAVDLVNEPKLDKEIKSWLAFAAQKVVE
              241                                                        360
              301
```

FIGURE 2 CONTINUED

```
                  *  **       *     *  *****  ******          *******          ** **
SEQ ID NO:02      VNALAKALAGQKDEVYFAANAAAQASRSSPRVTNEEVQKAAAALRGSDHRRSTTVSARL
SEQ ID NO:04      VNALAKALSGNKDVAFFSANAAAQASRKSSPRVTNEAVQKAAAALKGSDHRRATNVSARL
SEQ ID NO:06      VNALAKALAGHKDEAFFSANATAQASRKSSPRVTNEAVQKAAAALKGSDHRRATNVSSRL
SEQ ID NO:08      ------------------------------SSPRVNNE-VQKAAAALKGSDHRRATPVSARL
SEQ ID NO:10      ------------------------------SSPRVNNE-VQKAAAALKGSDHRRATPVSARL
SEQ ID NO:11      VNALAKALAGEKDEAFFSENAAAQASRKSSPRVTNQAVQKAAAALRGSDHRRATTVSARL
                                                                             420
                  ************ ******  ****  ** *********************  *
SEQ ID NO:02      DAQQKKLNLPVLPTTTIGSFPQTVELRRVRREYKAKKITEDEYISAIKEEISKVVKIQEE
SEQ ID NO:04      DAQQKKLNLPILPTTTIGSFPQTVELRRVRREFKANKISEEEYVKSIKEEIRKVVELQEE
SEQ ID NO:06      DAQQKKLNLPVLPTTTIGSFPQTVELRRVRREYKAKKISEEEYVKAIKAEIKKVVDLQEE
SEQ ID NO:08      ------------------------------------------------------------
SEQ ID NO:10      DAQQKKLNLPILPTTTIGSFPQTMDLRRVRREYKAKEDLXGVCQCYQGRNXQRLSRFKEE
SEQ ID NO:11      DAQQKKLNLPVLPTTTIGSFPQTLELRRVRREYKAKKISEDDYVKAIKEEISKVVKLQEE
                                                                             480
                  ******* *****  ********************** *****************
SEQ ID NO:02      LDIDVLVHGEPERNDMVEYFGEQLSGFAFTANGWVQSYGSRCVKPPIIYGDVSRPNPMTV
SEQ ID NO:04      LDIDVLVHGEPERNDMVEYFGEQLSGFAFTVNGWVQSYGSRCVKPPIIYGDVSRPKPMTV
SEQ ID NO:06      LDIDVLVHGEPERNDMVEYFGEQLSGFAFTANGWVQSYGSRCVKPPIIYGDVSRPNPMTV
SEQ ID NO:08      LDIDVLXQ----------------------------------------------------
SEQ ID NO:10      LDIDVLVHGEPERNDMVEYFGEQLSGFAFTANGWVQSYGSRCVKPPIIYGDVSRPNPMTV
SEQ ID NO:11      
                                                                             540
                                                                             481
```

FIGURE 2 CONTINUED

```
                **  *  *********************** **  *  ******************** *** ***
SEQ ID NO:02    FWSKMAQSMTPRPMKGMLTGPVTILNWSFVRNDQPRFETCYQIALALKKEVEDLEAAGIQ
SEQ ID NO:04    FWSSLAQSFTKRPMKGMLTGPVTILNWSFVRNDQPRSETTYQIALAIKDEVEDLEKAGIT
SEQ ID NO:06    FWSKTAQSMTKRPMKGMLTGPVTILNWSFVRNDQPRFETCYQIALAIKDEVEDLEKAGIT
SEQ ID NO:08    ------------------------------------------------------------
SEQ ID NO:10    -WRS--------------------------------------------------------
SEQ ID NO:11    FWSQTAQSMTKRPMKGMLTGPVTILNWSFVRNDQPRFETCYQIALAIKDEVEDLEKAGIN
                541                                                          600

********************************  *  *  *  ********************
SEQ ID NO:02    VIQIDEAALREGLPLRKSEHAFYLDWAVHSFRITNCGVQDTTQIHTHMCYSNFNDIIHSI
SEQ ID NO:04    VIQIDEAALREGLPLRKSEQAHYLDWAVHAFRITNVGVQDTTQIHTHMCYSNFNDIIHSI
SEQ ID NO:06    VIQIDEAALREGLPLRKAEHAFYLNWAVHSFRITNVGIQDTTQIHTHMCYSNFNDIIHSI
SEQ ID NO:08    ------------------------------------------------------------
SEQ ID NO:10    ----------LXKMTXVXYFGXQI------------------------------------
SEQ ID NO:11    VIQIDEAALREGLPLRKAEHAFYLDWAVHSFRITNLPLQDTTQIHTHMCYSNFNDIIHSI
                601                                                          660

************************************************************
SEQ ID NO:02    IDMDADVITIENSRSDEKLLSVFREGVKYGAGIGPGVYDIHSPRIPSTEEIADRVEKMLA
SEQ ID NO:04    IDMDADVITIENSRSDEKLLSVFREGVKYGAGIGPGVYDIHSPRIPPTEEIADRINKMLA
SEQ ID NO:06    IDMDADVITIENSRSDEKLLSVFREGVKYGAGIGPGVYDIHSPRIPSTEEIADRVNKMLA
SEQ ID NO:08    ------------------------------------------------------------
SEQ ID NO:10    ------------------------------------------------------------
SEQ ID NO:11    IDMDADVMTIENSRSSEKLLSVFREGVKYGAGIGPGVYDIHSPRIPSTEEIADRINKMLA
                661                                                          720
```

FIGURE 2 CONTINUED

```
              *  ****   ***********  ***  *   * *** *  * **  **
SEQ ID NO:02  VEDTNILWVNPDCGLKTRKYTEVKPALTNMVSATKLIRTQLASAK
SEQ ID NO:04  VLEKNILWVNPDCGLKTRKYTEVKPPSQNMVAAAKLIRYELA--K
SEQ ID NO:06  VLDTNILWVNPDCGLKTRKYAEVKPALENMVSAAKAIRTQLASSK
SEQ ID NO:08  ---------------------------------------------
SEQ ID NO:10  ---------------------------------------------
SEQ ID NO:11  VLDTNILWVNPDCGLKTRKYAEVKPALENMVSAAKLIRTQLASAK
              721                                        765
```

PLANT METHIONINE SYNTHASE GENE AND METHODS FOR INCREASING THE METHIONINE CONTENT OF THE SEEDS OF PLANTS

CROSS-REFERENCE TO RELATED APPLICATIONS

This application is a Continuation of application Ser. No. 09/377,431, filed Aug. 19, 1999, abandoned, which is a continuation-in-part of application Ser. No. 08/703,829, filed on Aug. 27, 1996 now abandoned, which claims benefit under 35 USC 119(e) to provisional Application 60/002,973, filed Aug. 30, 1995.

TECHNICAL FIELD

This invention relates to a nucleic acid fragment encoding a plant methionine synthase or methionine synthase. The invention also includes chimeric genes, a first encoding a plant methionine synthase (MS) gene, a second encoding a plant cystathionine γ-synthase (CS) gene, a third encoding feedback-insensitive aspartokinase (AK) or bifunctional feedback-insensitive aspartokinase-homoserine dehydrogenase (AK-HDH), which is operably linked to a plant chloroplast transit sequence, and a fourth encoding a methionine-rich protein, all operably linked to plant seed-specific regulatory sequences. Methods for their use to produce increased levels of methionine in the seeds of transformed plants are provided.

BACKGROUND OF THE INVENTION

Human food and animal feed derived from many grains are deficient in the sulfur amino acids, methionine and cysteine, which are required in an animal diet. In corn, the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Efforts to improve the sulfur amino acid content of crops through plant breeding have met with limited success on the laboratory scale and no success on the commercial scale. A mutant corn line which had an elevated whole-kernel methionine concentration was isolated from corn cells grown in culture by selecting for growth in the presence of inhibitory concentrations of lysine plus threonine [Phillips et al., *Cereal Chem.*, (1985), 62, 213–218[2ea]However, agronomically-acceptable cultivars have not yet been derived from this line and commercialized. Soybean cell lines with increased intracellular concentrations of methionine were isolated by selection for growth in the presence of ethionine [Madison and Thompson, *Plant Cell Reports*, (1988), 7, 472–476[, ]but plants were not regenerated from these lines.

The amino acid content of seeds is determined primarily by the storage proteins which are synthesized during seed development and which serve as a major nutrient reserve following germination. The quantity of protein in seeds varies from about 10% of the dry weight in cereals to 20–40% of the dry weight of legumes. In many seeds the storage proteins account for 50% or more of the total protein. Because of their abundance, plant seed storage proteins were among the first proteins to be isolated. Only recently, however, have the amino acid sequences of some of these proteins been determined with the use of molecular genetic techniques. These techniques have also provided information about the genetic signals that control the seed-specific expression and the intracellular targeting of these proteins.

One genetic engineering approach to increase the sulfur amino acid content of seeds is to isolate genes coding for proteins that are rich in the sulfur-containing amino acids methionine and cysteine, to link the genes to strong seed-specific regulatory sequences, to transform the chimeric gene into crops plants and to identify transformants wherein the gene is sufficiently-highly expressed to cause an increase in total sulfur amino acid content. However, increasing the sulfur amino acid content of seeds by expression of sulfur-rich proteins may be limited by the ability of the plant to synthesize methionine, by the synthesis and stability of the methionine-rich protein, and by effects of over-accumulation of the methionine-rich protein on the viability of the transgenic seeds.

An alternative approach would be to increase the production and accumulation of the free amino acid, methionine, via genetic engineering technology. However, little guidance is available on the control of the biosynthesis and accumulation of methionine in plants, particularly in the seeds of plants.

Methionine, along with threonine, lysine and isoleucine, are amino acids derived from aspartate. The first step in the pathway is the phosphorylation of aspartate by the enzyme aspartokinase (AK), and this enzyme has been found to be an important target for regulation of the pathway in many organisms. The aspartate family pathway is also believed to be regulated at the branch-point reactions. For methionine the reduction of aspartyl β-semialdehyde by homoserine dehydrogenase (HDH) may be an important point of control. The first committed step to methionine, the production of cystathionine from O-phosphohomoserine and cysteine by cystathionine γ-synthase (CS), appears to be an important point of control of flux through the methionine pathway [Giovanelli et al., *Plant Physiol.*, (1984), 77, 450–455[. ]The final step in methionine biosynthesis is catalyzed by the enzyme 5-methyltetrahydropteroyltriglutamate-homocysteine methyltransferase, also known as methionine synthase (MS). Nucleic acid fragments encoding full-length vitamin-B12 independent methionine synthases from Madagascar periwinkle (*Catharanthus roseus*) [Eichel et al., *Eur. J Biochem.* (1995), 230, 1053–1058[ C]oleus (*Solenoslemon scutellarioides*) [Petersen et al., *Plant Physiol.* (1995), 109, 338[, ]*Arabidopsis thaliana* [Ravanel et al., *Proc. Natl. Acad. Sci. USA* (1998), 95, 7805–7812[, ]and *Mesembryanthemum crystallinum* [NCBI General Identification No. 1814403[, ]as well as nuceic acid fragments encoding a portion of vitamin-B12 independent methionine synthase from a number of plant species such as soybean, rice, and corn have been disclosed previously.

SUMMARY OF THE INVENTION

The present invention provides plant genes encoding MS, specifically tobacco, corn and soybean MS genes, additional MS nucleic acid fragments from wheat, as well as chimeric MS genes for seed-specific over-expression of the plant enzyme. Combinations of these genes with other chimeric genes encoding AK, HDH, CS and methionine-rich seed storage protein provide methods to increase the level of methionine in seeds.

More specifically, the present invention concerns an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code.

In a second embodiment, this invention concerns an isolated nucleic acid fragment comprising:
  (a) a first nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code, and
  (b) a second nucleic acid fragment encoding a plant cystathionine γ-synthase or a functionally equivalent subfragment thereof.

In a third embodiment, this invention concerns chimeric genes comprising the isolated nucleic acid fragments discussed above operably linked to regulatory sequences.

In a fourth embodiment, this invention concerns plants and transformed hosts comprising such chimeric genes in their genome and seeds obtained from such plants, In a fifth embodiment, this invention concerns a polypeptide comprising all or a substantial portion of the amino acid sequence set forth in SEQ ID NOS:2, 4, 6, 8 and 10.

In a sixth embodiment, this invention concerns a method for increasing methionine content of the seeds of plants comprising:
  (a) transforming plant cells with the chimeric genes discussed above or the nucleic acid fragment discussed above;
  (b) growing fertile mature plants from the untransformed plant cells obtained from step (a) under conditions suitable to obtain seeds; and selecting progeny seed of step (b) for those seeds containing increased levels of methionine compared to untransformed seeds.

In a seventh embodiment, this invention concerns a method for producing plant methionine synthase comprising the following steps:
  (a) transforming microbial host cells with a chimeric gene wherein a nucleic acid fragment encoding a plant methionine synthase is operably linked to regulatory sequences capable of expression in microbial cells; then
  (b) growing the transformed microbial cells obtained from step (a) under conditions that result in expression of the methionine synthase protein.

In an eighth embodiment, this invention concerns a method for evaluating at least one compound for its ability to inhibit the activity of a plant methionine synthase, the method comprising the steps of: (a) transforming a host cell with a chimeric gene comprising a nucleic acid fragment encoding a plant methionine synthase, operably linked to suitable regulatory sequences; (b) growing the transformed host cell under conditions that are suitable for expression of the chimeric gene wherein expression of the chimeric gene results in production of plant methionine synthase in the transformed host cell; (c) optionally purifying the plant methionine synthase expressed by the transformed host cell; (d) treating the plant methionine synthase with a compound to be tested; and (e) comparing the activity of the plant methionine synthase that has been treated with a test compound to the activity of an untreated plant methionine synthase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows a comparison of the amino acid sequences of *E. coli* (SEQ ID NO:56), yeast (SEQ ID NO:57), tobacco (SEQ ID NO:58), *Catharanthus roseus* (SEQ ID NO:11), corn (SEQ ID NO:59) and soybean (SEQ ID NO:60) MS proteins.

FIG. 2 depicts the amino acid sequence alignment between the methionine synthase encoded by the corn clone p0026.ccras26rb (SEQ ID NO:2), contig assembled from soybean clones s2.17c08, sdc2c.pk001.g7, sdp2c.pk001.e21, sdp2c.pk001.n20, sdp2c.pk012.121, sdp2c.pk013.d12, sdp2c.pk042.g18, sdp3c.pk001.j3, sdp3c.pk006.n23, sdp3c.pk020.i10, ses4d.pk0010.f10, sfl1.pk129.j22, srm.pk0037.h2 and ssm.pk0070.h6 (SEQ ID NO:4), tobacco clone np.2d06.sk20 (SEQ ID NO:6), wheat clone wlm96.pk0018.c10 (SEQ ID NO:8), wheat clone wl1n.pk0038.e8 (SEQ ID NO:10) and a methionine synthase gene from *Catharanthus roseus* (NCBI General Identifier No. 1362086, SEQ ID NO:11). Amino acids which are conserved among all sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Methionine Synthase

| | | SEQ ID NO: | |
|---|---|---|---|
| Protein | Clone Designation | (Nucleotide) | (Amino Acid) |
| Methionine synthase (corn) | p0026.ccras26rb | 1 | 2 |
| Methionine synthase (soybean) | Contig of s2.17c08 sdc2c.pk001.g7 sdp2c.pk001.e21 sdp2c.pk001.n20 sdp2c.pk012.121 sdp2c.pk013.d12 sdp2c.pk042.g18 sdp3c.pk001.j3 sdp3c.pk006.n23 sdp3c.pk020.i10 ses4d.pk0010.f10 sfl1.pk129.j22 srm.pk0037.h2 ssm.pk0070.h6 | 3 | 4 |

TABLE 1-continued

Methionine Synthase

| Protein | Clone Designation | SEQ ID NO: | |
|---|---|---|---|
| | | (Nucleotide) | (Amino Acid) |
| Methionine synthase (tobacco) | np.2d06.sk20 | 5 | 6 |
| Methionine synthase (wheat) | w1m96.pk0018.c10 | 7 | 8 |
| Methionine synthase (wheat) | w1ln.pk0038.e8 | 9 | 10 |

SEQ ID NO:11 is the amino acid sequence of a *Catharanthus roseus* methionine synthase NCBI General Identifier No. 1362086.

SEQ ID NOS:12 and 13 set forth the sequences of oligonucleotides that were used in Example 8 to create a BspH I site at the translation start codon of the tobacco methionine synthase gene.

SEQ ID NOS:14 and 15 set forth the sequences of oligonucleotides that were used in Example 8 to create a Kpn I site following the translation stop codon of the tobacco methionine synthase gene.

SEQ ID NO:16 shows the nucleotide sequence of a corn CS cDNA described in Example 3.

SEQ ID NO:17 shows the deduced amino acid sequence of a corn CS protein derived from the nucleotide sequence of SEQ ID NO:16.

SEQ ID NO:18 shows the nucleotide sequence of a 3639 bp Xba I corn genomic DNA fragment encoding two-thirds of the corn CS protein and including 806 bp upstream from the protein coding region as described in Example 3.

SEQ ID NO:19 shows the complete amino acid sequence of the corn CS protein deduced from the corn cDNA fragment of SEQ ID NO:16 and the corn genomic DNA fragment of SEQ ID NO:18.

SEQ ID NOS:20 and 21 show oligonucleotides used to add a translation initiation codon to the corn CS gene.

SEQ ID NO:22 shows the nucleotide sequence of the coding region of the wild type *E. coli* lysC gene, which encodes AKIII, described in Example 5.

SEQ ID NO:23 shows the amino acid sequence of AKIII derived from the nucleotide sequence of SEQ ID NO:22.

SEQ ID NOS:24 and 25 were used in Example 5 to create an Nco I site at the translation start codon of the *E. coli* lysC gene.

SEQ ID NOS:26 and 27 were used in Example 6 to screen a corn library for a high methionine 10 kD zein gene.

SEQ ID NO:28 shows the nucleotide sequence (2123 bp) of the corn HSZ gene. Nucleotides 753–755 are the putative translation initiation codon and nucleotides 1386–1388 are the putative translation termination codon. Nucleotides 1–752 and 1389–2123 include putative 5' and 3' regulatory sequences, respectively.

SEQ ID NO:29 shows the deduced amino acid sequence of the primary translation product of the corn HSZ gene derived from the nucleotide sequence of SEQ ID NO:28.

SEQ ID NOS:30 and 31 were used in Example 7 to modify the HSZ gene by in vitro mutagenesis.

SEQ ID NO:32 shows a 639 bp DNA fragment including the corn HSZ coding region only, which can be isolated by restriction endonuclease digestion using Nco I (5'-CCATGG) to Xba I (5'-TCTAGA). Two Nco I sites that were present in the native HSZ coding region were eliminated by site-directed mutagenesis, without changing the encoded amino acid sequence.

SEQ ID NO:33 shows the deduced amino acid sequence of the corn HSZ protein derived from the nucleotide sequence of SEQ ID NO:32.

SEQ ID NOS:34 and 35 were used in Example 7 to create a form of the HSZ gene with alternative unique restriction endonuclease sites.

SEQ ID NOS:36 and 37 were used in Example 7 to create a gene to code for the mature form of HSZ.

SEQ ID NO:38 shows a 579 bp DNA fragment including the coding region of the mature corn HSZ protein only, which can be isolated by restriction endonuclease digestion using BspH I (5'-TCATGA) to Xba I (5'-TCTAGA). Two Nco I sites that were present in the native HSZ coding region were eliminated by site-directed mutagenesis. This was accomplished without changing the encoded amino acid sequence.

SEQ ID NO:39 shows the deduced amino acid sequence of the corn HSZ protein derived from the nucleotide sequence of SEQ ID NO:38.

SEQ ID NOS:40–45 were used in Example 8 to create a corn chloroplast transit sequence and link the sequence to the *E. coli* lysC-M4 gene.

SEQ ID NOS:46–49 were used in Example 9 to create a soybean chloroplast transit sequence and link the sequence to the *E. coli* lysC-M4 gene.

SEQ ID NOS:50–51 were used in Example 9 and 10 as PCR primers to prepare a DNA fragment carrying the soybean chloroplast transit sequence.

SEQ ID NO:52 was used in Example 9 to remove the corn chloroplast transit sequence from the corn CS gene.

SEQ ID NOS:53–54 were used in Example 10 as PCR primers to isolate and modify the *E. coli* metL gene.

SEQ ID NO:55 shows the nucleotide sequence of a partial soybean MS cDNA, described in Example 1.

The Sequence Descriptions contain the one letter code for nucleotide sequence characters and the three letter codes for amino acids as defined in conformity with the IUPAC-IYUB standards described in Nucleic Acids Research 13:3021–3030(1985) and in the Biochemical Journal 219 (No. 2):345–373(1984) which are incorporated by reference herein. The symbols and format used for nucleotide and amino acid sequence data comply with the rules set forth in 37 C.F.R. §1.822.

DETAILED DESCRIPTION OF THE INVENTION

The teachings below describe nucleic acid fragments, chimeric genes and procedures useful for increasing the accumulation of methionine in the seeds of transformed plants, as compared to levels of methionine in untransformed plants.

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in co-suppression or antisense by linking a nucleic acid fragment or subfragment thereof, whether or not it encodes an active enzyme, in the appropriate orientation relative to a plant promoter sequence.

The terms "substantially similar" and "corresponding substantially" as used herein refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the nucleic acid fragment of the invention. Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal method of alignment (Higgins and Sharp (1989) *CABIOS.* 5:151–153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are GAP PENALTY=10, GAP LENGTH PENALTY=10, KTUPLE=2, GAP PENALTY=5, WINDOW=4 and DIAGONALS SAVED=4.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F., et al., (1993) *J. Mol. Biol.* 215:403–410) and Gapped Blast (Altschul, S. F. et al., (1997) *Nucleic Acids Res.* 25:3389–3402). Thus, a substantial portion of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence often or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

As was mentioned above, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent similarity of the amino acid sequences that they encode to the amino acid sequences disclosed herein, as determined by algorithms commonly employed by those skilled in this art. Most preferred are nucleic acid fragments that encode amino acid sequences that are at least 87.6% identical to the amino acid sequence set forth in SEQ ID NO:2, or at least 87.8% identical to the amino acid sequence set forth in SEQ ID NO:4, or at least 92.5% identical to the amino acid sequence set forth in SEQ ID NO:6, or at least 86.3% identical to the amino acid sequence set forth in SEQ ID NO:8, or at least 80% identical to the amino acid sequence set forth in SEQ ID NO:10. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially assailable machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. "Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. "Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The CDNA can be single-stranded or converted into the double-stranded form using the klenow fragment of DNA polymerase I. "Sense" RNA refers to RNA transcript that includes the MRNA and so can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Altered expression" refers to the production of gene product(s) in transgenic organisms in amounts or proportions that differ significantly from that activity in comparable tissue (organ and of developmental type) from wild-type organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"End-product inhibition" or "feedback inhibition" refers to a biological regulatory mechanism wherein the catalytic activity of an enzyme in a biosynthetic pathway is reversibly reduced by binding to one or more of the end-products of the pathway when the concentration of the end-product(s) reaches a sufficiently high level, thus slowing the biosynthetic process and preventing over-accumulation of the end-product.

"Transformation" refers to the transfer of a nucleic acid fragment into the genome of a host organism, resulting in genetically stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature (London)* 327:70–73; U.S. Pat. No. 4,945,050), or an Agrobacterium-mediated method using an appropriate Ti plasmid containing the transgene (Ishida Y. et al., 1996, Nature Biotech. 14:745–750).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

An "expression construct" as used herein comprises any of the isolated nucleic acid fragments of the invention used either alone or in combination with each other as discussed herein and further may be used in conjunction with a vector or a subfragment thereof. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis. The terms "expression construct" and "recombinant expression construct" are used interchangeably herein.

The invention concerns an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code.

Isolation of a Plant MS Gene

In order to increase the accumulation of free methionine in the seeds of plants via genetic engineering, a gene encoding 5-methyltetrahydropteroyl-triglutamate-homocysteine methyltransferase, also known as methionine synthase (MS), was isolated from several crop plants. MS catalyzes the final reaction in the biosynthesis of methionine.

It is shown that plant MS genes can be isolated and identified by comparison of random plant cDNA sequences to the GenBank database using the BLAST algorithms well known to those skilled in the art. The use of this approach to isolate tobacco, soybean and corn MS cDNA genes is presented in detail in Example 1. The nucleotide sequence of a corn MS cDNA is provided in SEQ ID NO:1, the nucleotide sequence of a soybean MS cDNA assembled from a contig is provided in SEQ ID NO:3, the nucleotide sequence of a tobacco MS cDNA is provided in SEQ ID NO:5, and the partial nucleotide sequence of wheat MS cDNAs is provided in SEQ ID NOS:7 and 9. MS genes from other plants can now be identified by comparison of random cDNA sequences to the plant MS sequences provided herein. Alternatively, other plant MS genes, either as cDNAs or genomic DNAs, could be isolated directly by using either the tobacco, soybean, corn or wheat MS nucleic acid fragment as a DNA hybridization probe to screen libraries from any desired plant employing methodology well known to those skilled in the art.

Nucleic acid fragments carrying plant MS genes can be used to create chimeric genes which are useful for overexpressing MS in plant cells and in heterologous host cells. When over-expressed in plant cells, either alone or in combination with other proteins described below, MS is useful for increasing the biosynthesis and accumulation of methionine in those cells. It is particularly useful to use the MS gene to increase the methionine content in the cells of the seeds of plants.

It may also be desirable to reduce or eliminate expression of the MS gene in plants for some applications. In order to accomplish this, a chimeric gene designed for cosuppression of MS can be constructed by linking the MS gene or gene fragment to a plant promoter sequences. (See U.S. Pat. No. 5,231,020 for methodology to block plant gene expression via cosuppression.) Alternatively, a chimeric gene designed to express antisense RNA for all or part of the MS gene can be constructed by linking the MS gene or gene fragment in reverse orientation to a plant promoter sequences. (See U.S. Pat. No. 5,107,065 for methodology to block plant gene expression via antisense RNA.) Either the cosuppression or antisense chimeric gene could be introduced into plants via transformation. Transformants wherein expression of the endogenous MS gene is reduced or eliminated are then selected.

The plant MS protein produced in heterologous host cells, particularly in the cells of microbial hosts, can be used to prepare antibodies to the protein by methods well-known to those skilled in the art. The antibodies are useful for detecting plant MS protein in situ in cells or in vitro in cell extracts. Preferred heterologous host cells for production of plant MS protein are microbial hosts. Microbial expression systems and expression vectors containing regulatory sequences that direct high level expression of foreign proteins are well known to those skilled in the art. Any of these could be used to construct chimeric genes for production of plant MS. These chimeric genes could then be introduced into appropriate microorganisms via transformation to provide high level expression of plant MS. An example of a vector for high level expression of plant MS in a bacterial host is provided (Example 2).

In another aspect, this invention concerns a polypeptide comprising all or a substantial portion of the amino acid sequence set forth in SEQ ID NOS:2, 4, 6, 8 and 10.

Additionally, the plant methionine synthase protein can be used as a target to design and/or identify inhibitors of the enzyme that may be useful as herbicides. This is desirable because methionine synthase catalyzes a necessary step in the essential methionine biosynthetic pathway. Since methionine is metabolized to S-adenosyl-methionine, which is used in many important cellular processes, inhibition of methionine biosynthesis results in pleiotropic effects, which potentiate herbicidal activity. Accordingly, inhibition of methionine synthase activity could lead to inhibition of plant growth. Plant methionine synthase differs sufficiently from animal methionine synthase in amino acid sequence and action mechanism (Eichel et al. (1995) *Eur J Biochem* 230:1053–1058; Yamada et al. (1998) *Biosci Biotechnol Biochem* 62:2155–2160) that some inhibitors of plant methionine synthase are likely to be plant-specific. Thus, the instant polypeptides could be appropriate for new herbicide discovery and design.

In still another embodiment, this invention concerns a method for evaluating at least one compound for its ability to inhibit the activity of a plant methionine synthase, the method comprising the steps of:
  (a) transforming a host cell with a chimeric gene comprising a nucleic acid fragment encoding a plant methionine synthase, operably linked to suitable regulatory sequences;
  (b) growing the transformed host cell under conditions that are suitable for expression of the chimeric gene wherein expression of the chimeric gene results in production of the plant methionine synthase encoded by the operably linked nucleic acid fragment in the transformed host cell;
  (c) optionally purifying the plant methionine synthase expressed by the transformed host cell;
  (d) treating the plant methionine synthase with a compound to be tested; and
  (e) comparing the activity of the plant methionine synthase that has been treated with a test compound to the activity of an untreated plant methionine synthase,
thereby selecting compounds with potential for inhibitory activity.

Another aspect of the invention concerns an isolated nucleic acid fragment comprising:
  (a) a first nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code, and
  (b) a second nucleic acid fragment encoding a plant cystathionine γ-synthase or a functionally equivalent subfragment thereof.

Isolation of a Plant CS Gene

Cystathionine γ-synthase (CS) catalyzes the first reaction wherein cellular metabolites are committed to the synthesis of methionine and has been implicated to play a key role in the regulation of methionine biosynthesis. Regulation is not achieved through feedback inhibition of CS by any of the pathway end-products [Thompson et al. (1982) *Plant Physiol.* 69:1077–1083[, ]however. Thus, over-expression of CS is expected to increase flux through the methionine branch of the biosynthetic pathway, even when high levels of methionine are accumulated.

In order to increase the accumulation of free methionine in the seeds of plants it may desirable to increase the expression of cystathionine γ-synthase (CS) in concert with MS. Therefore a gene encoding plant cystathionine γ-synthase (CS) is provided. Also provided herein is a unique nucleic acid fragment containing a plant MS gene linked to a plant CS gene.

A plant CS gene was isolated by complementation of an *E. coli* host strain bearing a metB mutation. Such a strain requires methionine for growth due to inactivation of the *E. coli* gene that encodes CS. Functional expression of the plant CS gene allowed the strain to grow in the absence of methionine. The use of this approach to isolate a corn CS cDNA gene is presented in detail in Example 3. The nucleotide sequence of a corn CS cDNA is provided in SEQ ID NO:16. CS genes from other plants could be similarly isolated by functional complementation of an *E. coli* metB mutation. Alternatively, other plant CS genes, either as cDNAs or genomic DNAs, could be isolated by using the corn CS gene as a DNA hybridization probe.

This invention also concerns a method for increasing methionine content of the seeds of plants comprising:
  (a) transforming plant cells with a chimeric gene comprising an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code operably linked to a regulatory sequence, or a nucleic acid fragment comprising (1) a chimeric gene comprising an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code operably linked to a regulatory sequence and (2) a second chimeric gene comprising a nucleic acid fragment encoding a plant cystathionine γ-synthase or a functionally equivalent subfragment thereof or a complement thereof operably linked to a regulatory sequence;
  (b) growing fertile mature plants from the untransformed plant cells obtained from step (a) under conditions suitable to obtain seeds; and
selecting progeny seed of step (b) for those seeds containing increased levels of methionine compared to untransformed seeds.

Also of interest are plants comprising in their genome such chimeric genes and seeds obtained from such plants.

In still another aspect this invention conerns a method for producing plant methionine synthase comprising:
  (a) transforming host cells with a chimeric gene comprising an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code operably linked to a regulatory sequence, or a nucleic acid fragment comprising (1) a chimeric gene comprising an isolated nucleic acid fragment comprising a nucleotide sequence selected from the group consisting of (a) a nucleotide sequence corresponding to any of the nucleotide sequences set forth in SEQ ID NOS:1, 3, 5, 7 or 9 or the complement thereof, or (b) the nucleotide sequence of (a) wherein said sequence is degenerate in accordance with the degeneracy of the genetic code operably linked to a regulatory sequence and (2) a second chimeric gene comprising a nucleic acid fragment encoding a plant cystathionine γ-synthase or a functionally equivalent subfragment thereof or a complement thereof operably linked to a regulatory sequence;
  (b) growing the transformed microbial cells obtained from step (a) under conditions that result in expression of a plant methionine synthase protein.

As is clear from the discussion above, the host cell can be a plant cell or a microbial cell.

Isolation of AK Genes

Over-expression of feedback-insensitive AK increases flux through the entire pathway of aspartate-derived amino acids even in the presence of high concentrations of the pathway end-products lysine, threonine and methionine. This increased flux provides more substrate for CS and MS and increases the potential for methionine over-accumulation.

Provided herein is a unique nucleic acid fragment containing a plant MS gene linked to a plant CS gene and a gene for AK, which is insensitive to feedback-inhibition by end-products of the biosynthetic pathway. Also provided is a unique nucleic acid fragment containing a plant MS gene linked to a plant CS gene and a gene for AK-HDH, both activities of which are insensitive to feedback-inhibition by end-products of the biosynthetic pathway. Over-expression of feedback-insensitive AK-HDH directs the increased flux through the methionine-threonine branch of the aspartate-derived amino acid pathway, further increasing the potential for methionine biosynthesis.

A number of AK and AK-HDH genes have been isolated and sequenced. These include the thrA gene of *E. coli* (Katinka et al. (1980) *Proc. Natl. Acad. Sci. USA* 77:5730–5733[, ]the metL gene of *E. coli* (Zakin et al. (1983) *J. Biol. Chem.* 258:3028–3031[2ca]the lysC gene of *E. coli* [Cassan et al. (1986) *J. Biol. Chem.* 261:1052–1057[, ]and the HOM3 gene of *S. cerevisiae* [Rafalski et al. (1988)*J. Biol. Chem.* 263:2146–2151[. ]The thrA gene of *E. coli* encodes a bifunctional protein, AKI-HDHI. The AK activity of this enzyme is inhibited by threonine. The metL gene of *E. coli* also encodes a bifunctional protein, AKII-HDHII, and the AK activity of this enzyme is insensitive to all pathway end-products. The *E. coli* lysC gene encodes AKIII, which is sensitive to lysine inhibition. The HOM3 gene of yeast encodes an AK which is sensitive to threonine.

As indicated above AK genes are readily available to one skilled in the art for use in the present invention. A preferred class of AK genes encoding feedback-insensitive enzymes are derived from the *E. coli* lysC gene. Procedures useful for the isolation of the wild type *E. coli* lysC gene and lysine-insensitive mutations are presented in detail in Example 5.

The sequences of three mutant lysC genes that encoded lysine-insensitive aspartokinase each differed from the wild type sequence by a single nucleotide, resulting in a single amino acid substitution in the protein. Other mutations could be generated at these target sites in vitro by site-directed mutagenesis, using methods known to those skilled in the art. Such mutations would be expected to result in a lysine-insensitive enzyme. Furthermore, the in vivo method described in Example 5 could be used to easily isolate and characterize as many additional mutant lysC genes encoding lysine-insensitive AKIII as desired.

Another preferred class of AK genes are those encoding bi-functional enzymes, AK-HDH, wherein both catalytic activities are insensitive to end-product inhibition. A preferred AK-HDH enzyme is *E. coli* AKII-HDHII encoded by the metL gene. As indicated above, this gene has been isolated and sequenced previously. Thus, it can be easily obtained for use in the present invention by the same method used to obtain the lysC gene described in Example 5. Alternatively, the gene can be isolated from *E. coli* genomic DNA via PCR using oligonucleotide primers designed based on the published DNA sequence as described in Example 9.

In addition to these genes, several plant genes encoding lysine-insensitive AK are known. In barley, lysine plus threonine-resistant mutants bearing mutations in two unlinked genes that result in two different lysine-insensitive AK isoenzymes have been described [Bright et al., *Nature*, (1982), 299, 278–279, Rognes et al., *Planta*, (1983), 157, 32–38, Arruda et al., *Plant Phsiol.*, (1984), 76, 442–446[. ]In corn, a lysine plus threonine-resistant cell line had AK activity that was less sensitive to lysine inhibition than its parent line [Hibberd et al., *Planta*, (1980), 148, 183–187[. ]A subsequently isolated lysine plus threonine-resistant corn mutant is altered at a different genetic locus and also produces lysine-insensitive AK [Diedrick et al., *Theor. AppL Genet.*, (1990), 79, 209–215, Dotson et al., *Planta*, (1990), 182, 546–552[. ]In tobacco there are two AK enzymes in leaves, one lysine-sensitive and one threonine-sensitive. A lysine plus threonine-resistant tobacco mutant that expressed completely lysine-insensitive AK has been described [Frankard et al., *Theor. Appl. Genet.*, (1991), 82, 273–282[. ]These plant mutants could serve as sources of genes encoding lysine-insensitive AK and used, based on the teachings herein, to increase the accumulation of methionine in the seeds of transformed plants.

A partial amino acid sequence of AK from carrot has been reported [Wilson et al., *Plant Physiol.*, (1991), 97, 1323–1328[. ]Using this information a set of degenerate DNA oligonucleotides could be designed, synthesized and used as hybridization probes to permit the isolation of the carrot AK gene. Recently the carrot AK gene has been isolated and its nucleotide sequence has been determined [Matthews et al., (1991), U.S. Ser. No. 07/746, 705[2ea]This gene was used as a heterologous hybridization probe to isolate the *Arabidopsis thaliana* AK-HUH gene [Ghislain et al., *Plant Mol Biol*, (1994), 24, 835–851[, ]and thus can be used as a heterologous hybridization probe to isolate the plant genes encoding lysine-insensitive AK or AK-HDH described above.

Methionine-Rich Storage Protein Genes

It may be useful for certain applications to incorporate the excess free methionine produced via deregulation of the biosynthetic pathway into a storage protein. This can help to prevent metabolism of the excess free methionine into such products as S-adenosyl-methionine, which may be undesirable. The storage protein chosen should contain higher levels of methionine than average proteins. Ideally, these methionine-rich storage proteins should contain at least 15% methionine by weight.

A number of methionine-rich plant seed storage proteins have been identified and their corresponding genes have been isolated. A gene in corn for a 15 kD zein protein containing about 15% methionine by weight [Pedersen et al., *J. Biol. Chem.*, (1986), 261, 6279–6284[, ]a gene for a 10 kD zein protein containing about 30% methionine by weight [Kirihara et al., *Mol. Gen. Genet.*, (1988), 21, 477–484; Kirihara et al., *Gene*, (1988), 71, 359–370[ h]ave been isolated. A gene from Brazil nut for a seed 2S albumin containing about 24% methionine by weight has been isolated [Altenbach et al., *Plant Mol. Biol.*, (1987), 8, 239–250[. ]From rice a gene coding for a 10 kD seed prolamin containing about 25% methionine by weight has been isolated [Masumura et al., *Plant Mol. Biol.*, (1989), 12, 123–130[. ]A preferred gene, which encodes the most methionine-rich natural storage protein known, is an 18 kD zein protein designated high sulfur zein (HSZ) containing about 37% methionine by weight that has recently been isolated [World Patent Publication No. WO 92/14822, see Example 6[. ]Thus, methionine-rich storage protein genes are readily available to one skilled in the art.

Below is provided a discussion concerning the construction of chimeric genes for high-level seed-specific expression of methionine-rich storage protein genes. In addition, there have been several reports on the expression of methionine-rich seed storage protein genes in transgenic plants. The high-methionine 2S albumin from Brazil nut has been expressed in the seeds of transformed tobacco under the control of the regulatory sequences from a bean phaseolin storage protein gene. The protein was efficiently processed from a 17 kD precursor to the 9 kD and 3 kD subunits of the mature native protein. The accumulation of the methionine-rich protein in the tobacco seeds resulted in an up to 30% increase in the level of methionine in the seeds [Altenbach et al., *Plant Mol. Biol.*, (1989), 13, 513–522[. ]This methionine-rich storage protein has also been efficiently expressed in Canola seeds [Altenbach et al., *Plant Mol. Biol.*, (1992), 18, 235–245.[ I]n another case, high-level seed-specific expression of the 15 kD methionine-rich zein, under the control of the regulatory sequences from a bean phaseolin storage protein gene, was found in transformed tobacco; the signal sequence of the monocot precursor was also correctly processed in these transformed plants [Hoffman et al., *EMBO J*, (1987), 6, 3213–3221[. ]As another example, the 18 kD zein protein containing 37% methionine has been expressed in tobacco and soybean seeds [World Patent Publication No. WO 92/14822[2ea]

Construction of Chimeric Genes for Expression of MS, CS, AK, AK-HDH and Methionine-Rich Storage Proteins in the Seeds of Plants In order to increase biosynthesis of methionine in seeds, suitable regulatory sequences are provided to create chimeric genes for high level seed-specific expression of the MS, CS, AK or AK-HDH and methionine-rich storage proteins. The replacement of the native regulatory sequences accomplishes three things: 1) any methionine-concentration-dependent regulatory sequences are removed, permitting biosynthesis to continue in the presence of high levels of free methionine, 2) any pleiotropic effects that the accumulation of excess free methionine might have on the vegetative growth of plants is prevented because the chimeric gene(s) is not expressed in vegetative tissue of the transformed plants 3) high level expression of the enzyme(s) and storage protein(s) is obtained in the seeds.

The expression of foreign genes in plants is well-established [De Blaere et al., *Meth. Enzymol.*, (1987), 143, 277–291[. ]Proper level of expression of MS, CS, AK or AK-HDH and methionine-rich storage protein mRNAs may require the use of different chimeric genes utilizing different promoters. Such chimeric genes can be transferred into host plants either together in a single expression vector or sequentially using more than one vector. Preferred among the higher plants and the seeds derived from them are soybean, rapeseed (*Brassica napus, B. campestris*), sunflower (*Helianthus annus*), cotton (*Gossypium hirsulum*), corn, tobacco (*Nicotiana Tubacum*), alfalfa (*Medicago sativa*), wheat (*Triticum* sp.), barley (*Hordeum vulgare*), oats (*Avena sativa*, L), sorghum (*Sorghum bicolor*), rice (*Oryza sativa*), and forage grasses. Expression in plants will use regulatory sequences functional in such plants.

The origin of the promoter chosen to drive the expression of the coding sequence is not critical as long as it has sufficient transcriptional activity to accomplish the invention by expressing translatable mRNA for MS, CS, AK or AK-HDH and methionine-rich storage protein genes in the desired host tissue.

Preferred promoters are those that allow expression of the protein specifically in seeds. This may be especially useful, since seeds are the primary source of vegetable amino acids and also since seed-specific expression will avoid any potential deleterious effect in non-seed organs. Examples of seed-specific promoters include, but are not limited to, the promoters of seed storage proteins. The seed storage proteins are strictly regulated, being expressed almost exclusively in seeds in a highly organ-specific and stage-specific manner [Higgins et al., *Ann. Rev. Plant Physiol.*, (1984), 35, 191–221; Goldberg et al., *Cell*, (1989), 56, 149–160; Thompson et al., *BioEssays*, (1989), 10, 108–113[. ]Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin [Sengupta-Goplalan et al., *Proc. Natl. Acad. Sci. USA*, (1985), 82, 3320–3324; Hoffman et al., *Plant Mol. Biol.*, (1988), 11, 717–729[, ]bean lectin [Voelker et al., *EMBO J.*, (1987), 6, 3571–3577[, ]soybean lectin [Okamuro et al., *Proc. Natl. Acad. Sci. USA*, (1986), 83, 8240–8244[, ]soybean kunitz trypsin inhibitor [Perez-Grau et al., *Plant Cell*, (1989), 1, 095–1109[, ]soybean β-conglycinin [Beachy et al., *EMBO J.*, (1985), 4, 3047–3053; Barker et al., *Proc. Natl. Acad. Sci. USA*, (1988), 85, 458–462; Chen et al., *EMBO J.*, (1988), 7, 297–302; Chen,et al., *Dev. Genet.*, (1989), 10, 112–122; Naito et al., *Plant Mol Biol.*, (1988), 11, 109–123[, ]pea vicilin [Higgins et al., *Plant Mol. Biol.*, (1988), 11, 683–695[, ]pea convicilin [Newbigin et al., *Planta*, (1990), 180, 461[, ]pea legumin [Shirsat et al., *Mol. Gen. Genetics*, (1989), 215, 326[; ]rapeseed napin [Radke et al., *Theor. Appl. Genet.*, (1988), 75, 685–694[ a]s well as genes from monocotyledonous plants such as for maize 15 kD zein [Hoffman et al., *EMBO J.*, (1987), 6, 3213–3221; Schemthaner et al., *EMBO J.*, (1988), 7, 1249–1253; Williamson et al., *Plant Physiol.*, (1988), 88, 1002–1007[2ca]barley β-hordein [Marris et al., *Plant Mol. Biol.*, (1988), 10, 359–366[ a]nd wheat glutenin [Colot et al., *EMBO J.*, (1987), 6, 3559–3564[. ]Moreover, promoters of seed-specific genes, operably linked to heterologous coding sequences in chimeric gene constructs, also maintain their temporal and spatial expression pattern in transgenic plants. Such examples include linking either the Phaseolin or Arabidopsis 2S albumin promoters to the Brazil nut 2S albumin coding sequence and expressing such combinations in tobacco, Arabidopsis, or Brassica napus [Altenbach et al., *Plant Mol. Biol.*, (1989), 13, 513–522; Altenbach et al., *Plant Mol. Biol.*, (1992), 18, 235–245; De Clercq et al., *Plant Physiol.*, (1990), 94, 970–979[2ca]bean lectin and bean β-phaseolin promoters to express luciferase [Riggs et al., *Plant Sci.*, (1989), 63, 47–57[, ]and wheat glutenin promoters to express chloramphenicol acetyl transferase [Colot et al., *EMBO J.*, (1987), 6, 3559–3564[.%]Of particular use in the expression of the nucleic acid fragment of the invention will be the heterologous promoters from several extensively-characterized soybean seed storage protein genes such as those for the Kunitz trypsin inhibitor [Jofuku et al., *Plant Cell*, (1989), 1, 1079–1093; Perez-Grau et al., *Plant Cell*, (1989), 1, 1095–1109[, ]glycinin [Nielson et al., *Plant Cell*, (1989), 1, 313–328[, ]β-conglycinin [Harada et al., *Plant Cell*, (1989), 1, 415–425[2ea]Promoters of genes for α'- and β-subunits of soybean β-conglycinin storage protein will be particularly useful in expressing the CS, AK and AK-HDH mRNAs in the cotyledons at mid- to late-stages of soybean seed development [Beachy et al., *EMBO J.*, (1985), 4, 3047–3053; Barker et al., *Proc. Natl. Acad. Sci. USA*, (1988), 85, 458–462; Chen et al., *EMBO J.*, (1988), 7, 297–302; Chen et al., *Dev. Genet.*, (1989), 10, 112–122; Naito et al., *Plant Mol. Biol.*, (1988), 11, 109–123[ i]n transgenic plants, since: a) there is very little position effect on their expression in transgenic seeds, and b) the two promoters show different temporal regulation: the promoter for the α'-subunit gene is expressed a few days before that for the β-subunit gene.

Also of particular use in the expression of the nucleic acid fragments of the invention will be the promoters from several extensively characterized corn seed storage protein genes such as endosperm-specific promoters from the 10 kD zein [Kirihara et al., *Gene*, (1988), 71, 359–370[, ]the 27 kD zein [Prat et al., *Gene*, (1987), 52, 51–49; Gallardo et al., *Plant Sci.*, (1988), 54, 211–281[, ]and the 19 kD zein [Marks et al., *J. Biol. Chem.*, (1985), 260, 16451–16459[. ]The relative transcriptional activities of these promoters in corn have been reported [Kodrzyck et al., *Plant Cell*, (1989), 1, 105–114[ p]roviding a basis for choosing a promoter for use in chimeric gene constructs for corn. For expression in corn embryos, the strong embryo-specific promoter from the GLB1 gene [Kriz, *Biochemical Genetics*, (1989), 27, 239–251, Wallace et al., *Plant Physiol.*, (1991), 95, 973–975[ c]an be used.

It is envisioned that the introduction of enhancers or enhancer-like elements into other promoter constructs will also provide increased levels of primary transcription for MS, CS, AK or AK-HDH and methionine-rich storage protein genes to accomplish the invention. These would include viral enhancers such as that found in the 35S promoter [Odell et al., *Plant Mol. Biol.*, (1988), 10, 263–272[, ]enhancers from the opine genes [Fromm et al., *Plant Cell*, (1989), 1, 977–984[, ]or enhancers from any other source that result in increased transcription when placed into a promoter operably linked to the nucleic acid fragment of the invention.

Of particular importance is the DNA sequence element isolated from the gene for the α-subunit of βconglycinin that can confer 40-fold seed-specific enhancement to a constitutive promoter [Chen et al., *EMBO J*, (1988), 7, 297–302; Chen et al., *Dev. Genet.*, (1989), 10, 112–122[. ]One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a polyadenylation signal and other regulatory sequences that may be required for the proper expression of the CS and AK coding regions can be used to accomplish the invention. This would include the 3' end from any storage protein such as the 3' end of the bean phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions [for example, see Ingelbrecht et al., *Plant Cell*, (1989), 1, 671–680[.%]DNA sequences coding for intracellular localization sequences may be added to the AK or AK-HDH coding sequence if required for the proper expression of the proteins to accomplish the invention. Plant amino acid biosynthetic enzymes are known to be localized in the chloroplasts and therefore are synthesized with a chloroplast targeting signal. The plant-derived MS, CS and methionine-rich storage protein coding sequences include the native intracellular targeting signals, but bacterial proteins such as *E. coli* AKIII and AKII-HDHII have no such signal. A chloroplast transit sequence could, therefore, be fused to the coding sequence. Preferred chloroplast transit sequences are those of the small subunit of ribulose 1,5-bisphosphate carboxylase, e.g. from soybean [Berry-Lowe et al., *J. Mol. Appl. Genet.*, (1982), 1, 483–498[ f]or use in dicotyledonous plants and from corn [Lebrun et al., *Nucleic Acids Res.*, (1987), 15, 4360[ f]or use in monocotyledonous plants.

Introduction of Chimeric Genes Into Plants

Various methods of introducing a DNA sequence into eukaryotic cells (i.e., of transformation) of higher plants are available to those skilled in the art (see EPO publications 0 295 959 A2 and 0 138 341 A1). Such methods include those based on transformation vectors utilizing the Ti and Ri plasmids of *Agrobacterium* spp. It is particularly preferred to use the binary type of these vectors. Ti-derived vectors transform a wide variety of higher plants, including monocotyledonous and dicotyledonous plants, such as soybean, cotton and rape [Pacciotti et al., *Bio/Technology*, (1985), 3, 241; Byme et al., *Plant Cell, Tissue and Organ Culture*, (1987), 8, 3; Sukhapinda et al., *Plant Mol. Biol.*, (1987), 8, 209–216; Lorz et al., *Mol. Gen. Genet.*, (1985), 199, 178; Potrykus, *Mol. Gen. Genet.*, (1985), 199, 183[.%]Other transformation methods are available to those skilled in the art, such as direct uptake of foreign DNA constructs [see EPO publication 0 295 959 A2[, ]techniques of electroporation [see Fromm et al., *Nature (London)*, (1986), 319, 791[ o]r high-velocity ballistic bombardment with metal particles coated with the nucleic acid constructs [see Kline et al., *Nature (London)*, (1987), 327, 70, and see U.S. Pat. No. 4,945,050[. ]Once transformed, the cells can be regenerated by those skilled in the art.

Of particular relevance are the methods to transform foreign genes into commercially important crops, such as rapeseed [see De Block et al., *Plant Physiol.*, (1989), 91, 694–701[2ca]sunflower [Everett et al., *Bio/Technology*, (1987), 5, 1201[, ]soybean [McCabe et al., *Bio/Technology*, (1988), 6, 923; Hinchee et al., *Bio/Technology*, (1988), 6, 915; Chee et al., *Plant Physiol.*, (1989), 91, 1212–1218; Christou et al., *Proc. Natl. Acad. Sci USA*, (1989), 86, 7500–7504; EPO Publication 0 301 749 A2[, ]and corn [Gordon-Kamm et al., *Plant Cell*, (1990), 2, 603–618; Fromm et al, *Biotechnology*, (1990), 8, 833–839[.%]There are a number of methods that can be used to obtain nucleic acid fragments and plants containing multiple chimeric genes of this invention. Chimeric genes for seed-specific expression of MS, CS, AK or AKHDH and methionine-rich storage proteins can be linked on a single nucleic acid fragment which can be used for transformation. Plants wherein two or more chimeric genes are linked on a nucleic acid fragment integrated into a plant chromosome are selected. In another method two or more of the MS, CS, AK or AKHDH and methionine-rich storage protein chimeric genes, carried on separate DNA fragments, are co-transformed into the target plant and transgenic plants carrying two or more chimeric genes linked on a nucleic acid fragment integrated into a plant chromosome are selected. Alternatively, a plant transformed with an MS chimeric gene can be crossed with a plant transformed with a CS, AK or AKHDH and/or a methionine-rich storage protein chimeric gene, and hybrid plants carrying two or more chimeric genes can be selected. In yet another method a plant transformed with one of the chimeric genes is re-transformed with another chimeric gene or genes.

Expression of Chimeric Genes in Transformed Plants

To analyze for expression of the chimeric MS, CS, AK, AK-HDH and methionine-rich storage protein gene in seeds and for the consequences of expression on the amino acid content in the seeds, a seed meal can be prepared by any suitable method. The seed meal can be partially or completely defatted, via hexane extraction for example, if desired. Protein extracts can be prepared from the meal and analyzed for MS, CS, AK or HDH enzyme activities. Alternatively the presence of any of the proteins can be tested for immunologically by methods well-known to those skilled in the art. To measure free amino acid composition of the seeds, free amino acids can be extracted from the meal by methods known to those skilled in the art [for example, Bieleski et al., *Anal. Biochem.*, (1966), 17, 278–293[.]Amino acid composition can then be determined using any commercially available amino acid analyzer. To measure total amino acid composition of the seeds, meal containing both protein-bound and free amino acids can be acid-hydrolyzed to release the protein-bound amino acids and the composition can then be determined using any commercially available amino acid analyzer. Seeds expressing the MS, CS, AK, AK-HDH and/or methionine-rich storage proteins and with higher methionine content than the wild type seeds can thus be identified and propagated.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Isolation of Plant MS Genes cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| np | Young Tobacco Green Seedling | np.2d06.sk20 |
| p0026 | Corn Regenerating Callus 5 Days After Auxin Removal | p0026.ccras26rb |
| s2 | Soybean Seed, 19 Days After Flowering | s2.17b10<br>s2.17c08 |
| sdc2c | Soybean Developing Cotyledon (6–7 mm) | sdc2c.pk001.g7 |
| sdp2c | Soybean Developing Pod (6–7 mm) | sdp2c.pk001.e21<br>sdp2c.pk001.n20<br>sdp2c.pk012.121 |

TABLE 2-continued cDNA Libraries from Corn, Rice, Soybean and Wheat

| Library | Tissue | Clone |
|---|---|---|
| | | sdp2c.pk013.d12<br>sdp2c.pk042.g18 |
| sdp3c | Soybean Developing Pod (8–9 mm) | sdp3c.pk001.j3<br>sdp3c.pk006.n23<br>sdp3c.pk020.i10 |
| ses4d | Soybean Embryogenic Suspension 4 Days After Subculture | ses4d.pk0010.f10 |
| sfl1 | Soybean Immature Flower | sfl1.pk129.j22 |
| srm | Soybean Root Meristem | srm.pk0037.h2 |
| ssm | Soybean Shoot Meristem | ssm.pk0070.h6 |
| wl1n | Wheat Leaf From 7 Day Old Seedling* | wl1n.pk0038.e8 |
| wlm96 | Wheat Seedling 96 Hours After Inoculation With *Erysiphe graminis f. sp tritici* | wlm96.pk0018.c10 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10 B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer. Complete nucleotide sequence of the cDNAs may be determined using a ABI Model 373A DNA sequencer.

cDNA clones encoding methionine synthase were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

A tobacco cDNA library was constructed using RNA derived from young green seedlings. The RNA was sent to Stratagene Cloning Systems (La Jolla, Calif.) for the custom synthesis of a CDNA library in the Lambda Uni-Zap™ XR vector. Randomly picked individual cDNA inserts were amplified from phage DNA via PCR and the DNA was sequenced using a ABI Model 373A DNA sequencer. The DNA sequences were analyzed for similarity to all publicly available previous DNA sequences in the GeneBank Database using the BLASTN algorithm provided by the National Center for Biotechnology Information (NCBI). The DNA sequences were translated in all reading frames and compared for similarity to all publicly available previous protein sequences in the GeneBank Database using the BLASTX algorithm provided by the NCBI.

The BLASTX search using clone np.2d06.sk20 revealed unmistakable similarity of the protein encoded by the DNA to *E. coli* MS and yeast MS. The amino acid sequence similarity began essentially at the start of both the *E. coli* and yeast proteins indicating that the tobacco cDNA was likely to be a nearly full length cDNA. *E. coli* MS is a protein of 753 amino acids and yeast MS contains 767 amino acids. Thus, the coding region of the tobacco MS would be expected to be 2250–2300 nucleotides long. A plasmid-borne vector carrying the tobacco MS cDNA insert was excised from the lambda phage using the standard lambda-zap procedure provided by Stratagene and designated pBT771. The ampicillin-resistant plasmid carried the CDNA insert in the vector pBluescript SK(−). Restriction endonuclease digests of the plasmid indicated that the CDNA insert was about 2.6 kb, thus long enough to encode a complete tobacco MS protein.

The complete nucleotide sequence of the full length tobacco MS cDNA clone was determined using a ABI Model 373A DNA sequencer. SEQ ID NO:5 shows the nucleotide sequence of the tobacco MS cDNA and the corresponding amino acid sequence of the tobacco MS protein. The amino acid sequence of tobacco MS shows approximately 44% sequence similarity to either the *E. coli* or yeast proteins.

Similarly, a corn CDNA library was constructed using RNA derived from developing kernels 15 days after pollination. The RNA was sent to Stratagene Cloning Systems (La Jolla, Calif.) for the custom synthesis of a cDNA library in the Lambda Uni-Zap™ XR vector, randomly picked individual cDNA inserts were amplified from phage DNA via PCR, and the DNA was sequenced using a ABI Model 373A DNA sequencer. The DNA sequences were analyzed as described above.

The BLASTX search using clone m.15.4.c03.sk20 revealed unmistakable similarity of the protein encoded by the DNA to *E coli* MS, yeast MS and tobacco MS (FIG. 1). The amino acid sequence similarity began in the middle of both the *E. coli* and yeast proteins indicating that the corn cDNA was not a full length cDNA. The partial corn MS amino acid sequence shows 45% similarity to *E. coli* MS, 48% similarity to yeast MS and 61% similarity to tobacco MS. Using similar methods, another corn cDNA clone, p0026.ccras26rb, was found to encode a full-length methionine synthase. The sequence of this corn MS CDNA is shown in SEQ ID NO:1.

Soybean cDNA libraries were constructed using RNA derived from developing seeds. The RNA was used to create cDNA libraries in the Lambda™Uni-Zap XR vector; bacterial plasmid cDNA libraries were derived from the phages using the Lambda-Zap procedure. Randomly picked individual CDNA clones were amplified from bacterial DNA via PCR, using primers complimentary to plasmid DNA that flanked the cDNA insert. The DNA was sequenced using a ABI Model 377 DNA sequences, and the DNA sequences were analyzed as described above.

The BLASTX search using clones s2.09c02, s2.11g02, s2.17b10, s2.17c08, s2.17f07 and se2.11f12 each revealed unmistakably similarity of the protein encoded by the DNA to *E. coli* MS, yeast MS, tobacco MS and *Catharanthus roseus* MS. A contiguous sequence was constructed using the 6 cDNA sequences above. The sequence of this soybean MS cDNA is shown in SEQ ID NO:55. The deduced amino acid sequence of the soybean cDNA showed strong similarity to the carboxy half of the *E. coli*, yeast and especially the tobacco and *Catharanthus roseus* MS proteins (FIG. 1). A longer contig from various soybean clones (Table 1) was assembled to encode a full-length methionine synthase, the nucleotide sequence of which is shown in SEQ ID NO:3.

The BLASTX search using the sequences from clones listed in Table 3 revealed similarity of the polypeptides encoded by the cDNAs to methionine synthase from different plant species. Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to Methionine Synthase

| | | BLAST Results | | |
|---|---|---|---|---|
| Clone | Status | Organism | General Identification No. | pLog Score |
| p0026.ccras26rb | FIS | Catharanthus roseus | 1362086 | >254.00 |
| Contig of s2.17c08 sdc2c.pk001.g7 sdp2c.pk001.e21 sdp2c.pk001.n20 sdp2c.pk012.121 sdp2c.pk013.d12 sdp2c.pk042.g18 sdp3c.pk001.j3 sdp3c.pk006.n23 sdp3c.pk020.i10 ses4d.pk0010.f10 sfl1.pk129.j22 srm.pk0037.h2 ssm.pk0070.h6 | Contig | Arabidopsis thaliana | 2738248 | >254.00 |
| np.2d06.sk20 | FIS | Catharanthus roseus | 1362086 | >254.00 |
| wlm96.pk0018.c10 | EST | Mesembryanthemum crystallinum | 1814403 | 70.40 |
| wlln.pk0038.e8 | EST | Catharanthus roseus | 1362086 | 29.30 |

FIG. 1 presents an alignment of the amino acid sequences set forth in SEQ ID NOs:2, 4, 6, 8 and 10 and the *Catha-*

*ranthus roseus* sequence (SEQ ID NO:11). The data in Table 4 represents a calculation of the percent identity of the amino acid sequences set forth in SEQ ID NOs:2, 4, 6, 8 and 10 and the *Catharanthus roseus* sequence (SEQ ID NO:11).

TABLE 4

Percent Identity of Amino Acid Sequences Deduced From the Nucleotide Sequences of cDNA Clones Encoding Polypeptides Homologous to Methionine Synthase

| SEQ ID NO. | Percent Identity to General Identification No. 1362086; SEQ ID NO:11 |
|---|---|
| 2 | 87.5 |
| 4 | 87.5 |
| 6 | 92.4 |
| 8 | 84.7 |
| 10 | 57.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a methionine synthase. These sequences represent the first monocot (corn), soybean and tobacco cDNA sequences encoding full-length methionine synthase as well as the first wheat partial cDNA sequences encoding methionine synthase.

Example 2

Construction of Chimeric MS Genes for Expression in *E. coli*

The tobacco MS gene was modified to permit the construction of chimeric genes for expression in *E. coli* and plant seeds. First, a BspH I site (TCATGA) was introduced at the ATG start codon using oligonucleotides CF49 and (SEQ ID NO:12) CF50 (SEQ ID NO:13). The oligonucleotides were annealed and inserted into pBT771 digested with EcoR I and EcoR V. This takes advantage of the unique EcoR I site at the junction of the vector and cDNA and a unique EcoR V site about 20 bp from the start codon. The result of this insertion is to remove the cDNA sequences upstream of the ATG start codon and to alter the second codon of the tobacco MS gene from GCA encoding alanine to ACA encoding threonine. Since threonine is the second amino acid in *E. coli* MS, the substitution of threonine for alanine in tobacco MS is not expected to affect the protein function. Insertion of an oligonucleotide with the correct sequence into this region was confirmed by DNA sequencing, yielding plasmid pBT772.

Next, a Kpn I site was added immediately following the translation stop codon. This was accomplished by using PCR employing pBT771 DNA as template and primers CF51 (SEQ ID NO:14) and CF52 (SEQ ID NO:15) to generate a modified 280 base pair fragment that was digested with Rsr II and Kpn I and inserted into similarly digested pBT772. This DNA fragment replacement removes the 3' non-coding sequences present in the tobacco MS cDNA. Insertion of a DNA fragment with the correct sequence was confirmed by DNA sequencing, yielding plasmid pBT773, which contains a unique 2306 bp BspH I to Kpn I fragment carrying the tobacco MS coding region only.

To achieve high level expression of the tobacco MS gene in *E. coli* a modified version bacterial expression vector pET-3a [Rosenberg et al., *Gene*, (1987), 56, 125–135[ w]as used. This expression vector employs the bacteriophage T7 RNA polymerase/T7 promoter system. First, an oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG creating pBT430. Then pBT430 was further modified to include a Kpn I site downstream of the Nco I site at the translation initiation codon. The tobacco MS gene was cut out of pBT773 as a 2300 bp BspH I-Kpn I fragment and inserted into the above described expression vector digested with Nco I and Kpn I.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 3

Isolation of a Plant CS Gene

In order to clone the corn CS gene, RNA was isolated from developing seeds of corn line H99 19 days after pollination. This RNA was sent to Clontech Laboratories, Inc., (Palo Alto, Calif.) for the custom synthesis of a cDNA library in the vector Lambda Zap II. The conversion of the Lambda Zap II library into a phagemid library, then into a plasmid library was accomplished following the protocol provided by Clontech. Once converted into a plasmid library the ampicillin-resistant clones obtained carry the cDNA insert in the vector pBluescript SK(−). Expression of the cDNA is under control of the lacZ promoter on the vector.

Two phagemid libraries were generated using the mixtures of the Lambda Zap II phage and the filamentous helper phage of 100 mL to 1 mL. Two additional libraries were generated using mixtures of 100 μL Lambda Zap II to 10 μL helper phage and 20 μL Lambda Zap II to 10 μL helper phage. The titers of the phagemid preparations were similar regardless of the mixture used and were about $2 \times 10^3$ ampicillin-resistant-transfectants per mL with E. coli strain XL1-Blue as the host.

To identify clones that carried the CS gene, E. coli strain BOB105 was constructed by introducing the F' plasmid from E. coli strain XL1-blue into strain UB 1005 [Clark (1984) FEMS Microbiol. Lett. 21:189[ b]y conjugation. The genotype of BOB105 is: F'::Tn10 proA$^+$B$^+$lacI$^q$D(lacZ) M15/nalA37metB1. The strain requires methionine for growth due to a mutation in the metB gene that encodes CS. Functional expression of the plant CS gene should complement the mutation and allow the strain to grow in the absence of methionine.

To select for clones from the corn cDNA library that carried the CS gene, 100 μL of the phagemid library was mixed with 300 μL of an overnight culture of BOB105 grown in L broth and incubated at 37° for 15 min. The cells were collected by centrifugation, resuspended in 400 μL of M9+vitamin B1 broth and plated on M9 media containing vitamin B1, glucose as a carbon and energy source, 20 μL threonine (to prevent the possibility of threonine starvation due to overexpression of CS), 100 μg/mL ampicillin, 20 μg/mL tetracycline, and 0.16 mM IPTG (isopropylthio-β-galactoside). Fifteen plates were prepared and incubated at 37° C. The amount of phagemid added was expected to yield about $2 \times 10^5$ ampicillin-resistant transfectants per plate.

Approximately 30 colonies (an average of 2 per plate or 1 per $10^5$ transfectants) able to grow in the absence of methionine were obtained. No colonies were observed if the phagemids carrying the corn cDNA library were not added. Twelve clones were picked and colony purified by streaking on the same medium described above. Plasmid DNA was isolated from the 12 clones and retransformed into BOB105. All of the 12 DNAs yielded methionine-independent transformants demonstrating that a plasmid-borne gene was responsible for the phenotype. The sequence of the DNA insert in one of the plasmids, FS1088, is shown in SEQ ID NO:16 and the deduced amino acid sequence of the corn CS protein derived from the nucleotide sequence of SEQ ID NO:16 is shown in SEQ ID NO:17. It is 1639 bp in length and contains a long open reading frame and a poly A tail, indicating that it too represents a corn cDNA. The deduced amino acid sequence of the open reading frame shows 59 percent similarity and 34 percent identity to the published sequence of E. coli CS, indicating that it represents a corn homolog to the E. coli metB gene.

The open reading frame in plasmid FS1088 continues to the end of the insert DNA, and does not include an ATG initiator codon, indicating that the cloned cDNA is incomplete. The open reading frame of FS1088 is in frame with the initiator codon of the lacZ gene carried on the cloning vector. Thus, complementation of the metB mutation in BOB105 results from expression of a fusion protein including 39 amino acids from β-galactosidase and the vector polylinker attached to the truncated corn CS protein.

In order to clone the entire 5' end of the corn CS gene, the cDNA clone was used as a DNA hybridization probe to screen a genomic corn library. A genomic library of corn in bacteriophage lambda was purchased from Stratagene (La Jolla, Calif.). Data sheets from the supplier indicated that the corn DNA was from etiolated Missouri 17 corn seedlings. The vector was Lambda FIX™ II carrying Xho I fragments 9–23 kb in size. A titer of $1.0 \times 10^{10}$ plaque forming units (pfu)/mL in the amplified stock was indicated by the supplier when purchased. Prior to screening, the library was re-titered and contained $2.0 \times 10^8$ pfu/mL.

The protocol used for screening the library by DNA hybridization was provided by Clonetech (Palo Alto, Calif.).

From autoradiograms of duplicate filters, 11 plaques which hybridized to a corn CS cDNA probe were identified. After a second round of screening two of the original plaques, number 6-1 and number 10-1, showed positive hybridization. These plaques were tested with the probe a third time; and well isolated plaques were picked from each original. Following a fourth probing all the plaques hybridized, indicating that pure clones had been isolated.

DNA was prepared from these two phage clones, 6-1 and 10-1, using the protocol for plate lysate method [see Sambrook et al. (1989) Molecular Cloning: A Laboratory Manual, Cold Spring Harbor Laboratory Press[. ]Restriction endonuclease digests and agarose gel electrophoresis showed the two clones to be identical. The DNA fragments from the agarose gel were "Southern-blotted" [see Sambrook et al. (1989) Molecular Cloning: A Laboratory Manual, Cold Spring Harbor Laboratory Press[ o]nto nylon filters and probed with labeled corn CS cDNA. A single 7.5 kb Sal I fragment and two Xba I fragments of 3.6 kb and 3.2 kb hybridized to the probe. The 3.2 kb Xba I fragment hybridized weakly to the probe whereas the 3.6 kb Xba I and the 7.5 kb Sal I fragments hybridized strongly.

The 3.6 kb Xba I fragment was cloned into the Xba I site of pGEM®-9Zf(–) that had been treated with calf intestinal alkaline phosphatase. Two subclones from each Xba I fragment with the fragments in both orientations with respect to pGEM®-9Zf(–) DNA were obtained following transformation of E. coli. The two 3.6 kb Xba I subclones were designated FS1179 and FS1180.

Restriction enzyme analysis of the subclones indicated that the 3.6 kb Xba I fragment in FS1179 and FS1180 included the 5' region of the corn CS gene. DNA from FS1180 was sent to LARK Sequencing Technologies Inc. (Houston, Tex.) for complete DNA sequencing analysis. The sequence of the entire 3639 bp Xba I fragment is shown in see SEQ ID NO:18.

Complete sequence analysis of the 3639 bp Xba I fragment revealed 806 bp of sequence upstream from the protein coding region and 2833 bp of DNA encoding two-thirds of the corn CS protein. The 2833 bp includes seven exons and seven introns with the 3' Xba I site located in the seventh intron. Table 1 describes the location and length of exons and introns in the sequence as well the number of amino acids encoded by the exons. The first exon includes the entire chloroplast targeting signal and 12 amino acids into the region that shows amino acid sequence alignment with the E. coli protein. The last codon in Exon 7 encodes amino acid 333 of corn CS as shown in SEQ ID NO:17.

TABLE 5

| REGION | FROM (bp) | TO (bp) | Length (bp) | Number of Encoded Amino Acids |
|---|---|---|---|---|
| Promoter | 1 | 806 | 806 | na* |
| Exon1 | 807 | 1194 | 387 | 129 |
| Intron1 | 1195 | 1301 | 106 | na |
| Exon2 | 1302 | 1405 | 103 | 35 |
| Intron2 | 1406 | 1489 | 83 | na |
| Exon3 | 1490 | 1563 | 73 | 24 |
| Intron3 | 1564 | 1646 | 82 | na |
| Exon4 | 1647 | 1815 | 168 | 57 |
| Intron4 | 1816 | 2507 | 691 | na |
| Exon5 | 2508 | 2567 | 59 | 20 |
| Intron5 | 2568 | 2660 | 92 | na |
| Exon6 | 2661 | 2864 | 203 | 68 |
| Intron6 | 2865 | 2947 | 82 | na |
| Exon7 | 2948 | 3034 | 86 | 29 |
| Intron7 | 3035 | 3639 | >604 | na |

*na = not applicable

Comparison of the corn CS cDNA sequence to the genomic CS DNA sequence indicated that the cDNA of clone FS1088 did not contain the entire chloroplast targeting signal as anticipated. The cDNA was not truncated on the 5' end, but instead contained a 170 bp deletion in the chloroplast transit sequence.

The complete amino acid sequence of the corn CS protein derived from combining the amino terminal sequence deduced from the corn genomic DNA fragment of SEQ ID NO:18 and the carboxy termninal sequence from the corn cDNA fragment of SEQ ID NO:16 is shown in SEQ ID NO:19.

Example 4

Modification of the Corn CS Gene and High Level Expression in E. coli

As indicated in Example 2, the open reading frame in plasmid FS1088 for the corn CS gene does not include an ATG initiator codon. Oligonucleotide adaptors OTG145 and OTG146 were designed to add an initiator codon in frame with the CS coding sequence.

```
OTG 145    5'-AATTCATGAG TGCA-3'    SEQ ID NO:20

OTG 146    5'-AATTTGCACT CATG-3'    SEQ ID NO:21
```

When annealed the oligonucleotides possess EcoR I sticky ends. Upon insertion into FS1088 in the desired orientation, an EcoR I site is present at the 5' end of the adaptor, the ATG initiator codon is within a BspH I restriction endonuclease site, and the EcoR I site at the 3' end of the adaptor is destroyed. The oligonucleotides were ligated into EcoR I digested FS1088, and insertion of the correct sequence in the desired orientation was verified by DNA sequencing.

To achieve high level expression of the corn CS gene in E. coli the bacterial expression vector pBT430 (see Example 2) was used. The corn CS gene was cut out of the modified FS1088 plasmid described above as an 1482 bp BspH I fragment and inserted into the expression vector pBT430 digested with Nco I. Clones with the CS gene in the proper orientation were identified by restriction enzyme mapping.

For high level expression each of the plasmids was transformed into E. coli strain BL21(DE3) or BL21(DE3) lysS [Studier et al., J. Mol. Biol., (1986), 189, 113–130[. ]Cultures were grown in LB medium containing ampicillin (100 mg/L) at 37° C. At an optical density at 600 nm of approximately 1, IPTG (isopropylthio-β-galactoside, the inducer) was added to a final concentration of 0.4 mM and incubation was continued overnight. The cells were collected by centrifugation and resuspended in ½0th the original culture volume in 50 mM NaCl; 50 mM Tris-Cl, pH 7.5; 1 mM EDTA, and frozen at −20° C. Frozen aliquots of 1 mL were thawed at 37° C. and sonicated, in an ice-water bath, to lyse the cells. The lysate was centrifuged at 4° C. for 5 min at 12,000 rpm. The supernatant was removed and the pellet was resuspended in 1 mL of the above buffer.

The supernatant and pellet fractions of uninduced and IPTG-induced cultures were analyzed by SDS polyacrylamide gel electrophoresis. The best of the conditions tested was the induced culture of the BL21(DE3)lysS host. The major protein visible by Coomassie blue staining in the pellet fraction of this induced culture had a molecular weight of about 54 kd, the expected size for corn CS.

Example 5

Isolation of the E. coli lysC Gene and Mutations in lysC Resulting in Lysine-Insensitive AKIII The E. coli lysC gene has been cloned, restriction endonuclease mapped and sequenced previously [Cassan et al., J. Biol. Chem., (1986), 261, 1052–1057[. ]For the present invention the lysC gene was obtained on a bacteriophage lambda clone from an ordered library of 3400 overlapping segments of cloned E. coli DNA constructed by Kohara, Akiyama and Isono [Kohara et al., Cell, (1987), 50, 595–508[. ]This library provides a physical map of the whole E. coli chromosome and ties the physical map to the genetic map. From the knowledge of the map position of lysC at 90 min. on the E. coli genetic map [Theze et al., J. Bacteriol., (1974), 117, 133–143[, ]the restriction endonuclease map of the cloned gene [Cassan et al., J. BioL Chem., (1986), 261, 1052–1057[, ]and the restriction endonuclease map of the cloned DNA fragments in the E. coli library [Kohara et al., Cell, (1987), 50, 595–508[, ]it was possible to choose lambda phages 4E5 and 7A4 [Kohara et al., Cell, (1987), 50, 595–508[ a]s likely candidates for carrying the lysC gene. The phages were grown in liquid culture from single plaques as described [see Current Protocols in Molecular Biology (1987) Ausubel et al. eds. John Wiley & Sons New York[ u]sing LE392 as host [see Sambrook et al. (1989) Molecular Cloning: A Laboratory Manual, Cold Spring Harbor Laboratory Press[. ]Phage DNA was prepared by phenol extraction as described [see Current Protocols in Molecular Biology (1987) Ausubel et al. eds. John Wiley & Sons New York[.%]From the sequence of the gene several restriction endonuclease fragments diagnostic for the lysC gene were predicted, including an 1860 bp EcoR I-Nhe I fragment, a 2140 bp EcoR I-Xmn I fragment and a 1600 bp EcoR I-BamH I fragment. Each of these fragments was detected in both of the phage DNAs confirming that these carried the lysC gene. The EcoR I-Nhe I fragment was isolated and subcloned in plasmid pBR322 digested with the same enzymes, yielding an ampicillin-resistant, tetracycline-sensitive E. coli transformant. The plasmid was designated pBT436.

To establish that the cloned lysC gene was functional, pBT436 was transformed into E. coli strain Gif106M1 (E. coli Genetic Stock Center strain CGSC-5074) which has mutations in each of the three E. coli AK genes [Theze et al., J. Bacteriol., (1974), 117, 133–143[. ]This strain lacks all AK activity and therefore requires diaminopimelate (a precursor to lysine which is also essential for cell wall biosynthesis), threonine and methionine. In the transformed strain all these nutritional requirements were relieved demonstrating that the cloned lysC gene encoded functional AKIII.

Addition of lysine (or diaminopimelate which is readily converted to lysine in vivo) at a concentration of approximately 0.2 mM to the growth medium inhibits the growth of Gif106M1 transformed with pBT436. M9 media [see Sambrook et al. (1989) Molecular Cloning: A Laboratory Manual, Cold Spring Harbor Laboratory Press[ s]upplemented with the arginine and isoleucine, required for Gif106M1 growth, and ampicillin, to maintain selection for the pBT436 plasmid, was used. This inhibition is reversed by addition of threonine plus methionine to the growth media. These results indicated that AKIII could be inhibited by exogenously added lysine leading to starvation for the other amino acids derived from aspartate. This property of pBT436-transforned Gif106M1 was used to select for mutations in lysC that encoded lysine-insensitive AKIII.

Single colonies of Gif106M1 transformed with pBT436 were picked and resuspended in 200 μL of a mixture of 100 μL 1% lysine plus 100 μL of M9 media. The entire cell suspension containing $10^7$–$10^8$ cells was spread on a petri dish containing M9 media supplemented with the arginine, isoleucine, and ampicillin. Sixteen petri dishes were thus prepared. From 1 to 20 colonies appeared on 11 of the 16 petri dishes. One or two (if available) colonies were picked and retested for lysine resistance and from this nine lysine-resistant clones were obtained. Plasmid DNA was prepared from eight of these and re-transformed into Gif106M1 to determine whether the lysine resistance determinant was plasmid-borne. Six of the eight plasmid DNAs yielded lysine-resistant colonies. Three of these six carried lysC genes encoding AKIII that was uninhibited by 15 mM lysine, whereas wild type AKIII is 50% inhibited by 0.3–0.4 mM lysine and >90% inhibited by 1 mM lysine.

To determine the molecular basis for lysine-resistance the sequences of the wild type lysC gene and three mutant genes were determined. The sequence of the wild type lysC gene cloned in pBT436 (SEQ ID NO:22) differed from the published lysC sequence in the coding region at 5 positions. Four of these nucleotide differences were at the third position in a codon and would not result in a change in the amino acid sequence of the AKIII protein. One of the differences would result in a cysteine to glycine substitution at amino acid 58 of AKIII. These differences are probably due to the different strains from which the lysC genes were cloned.

The sequences of the three mutant lysC genes that encoded lysine-insensitive AK each differed from the wild type sequence by a single nucleotide, resulting in a single amino acid substitution in the protein. Mutant M2 had an A substituted for a G at nucleotide 954 of SEQ ID NO:22 resulting in an isoleucine for methionine substitution at amino acid 318 and mutants M3 and M4 had identical T for C substitutions at nucleotide 1055 of SEQ ID NO:22 resulting in an isoleucine for threonine substitution at amino acid 352. Thus, either of these single amino acid substitutions is sufficient to render the AKIII enzyme insensitive to lysine inhibition.

An Nco I (CCATGG) site was inserted at the translation initiation codon of the lysC gene using the following oligonucleotides:

```
                                              SEQ ID NO:24
5'-GATCCATGGC TGAAATTGTT GTCTCCAAAT TTGGCG-3'

SEQ ID NO:25
5'-GTACCGCCAA ATTTGGAGAC AACAATTTCA GCCATG-3'
```

When annealed these oligonucleotides have BamH I and Asp 718 "sticky" ends. The plasmid pBT436 was digested with BamH I, which cuts upstream of the lysC coding sequence and Asp 718 which cuts 31 nucleotides downstream of the initiation codon. The annealed oligonucleotides were ligated to the plasmid vector and E. coli transformants were obtained. Plasmid DNA was prepared and screened for insertion of the oligonucleotides based on the presence of an Nco I site. A plasmid containing the site was sequenced to assure that the insertion was correct, and was designated pBT457. In addition to creating an Nco I site at the initiation codon of lysC, this oligonucleotide insertion changed the second codon from TCT, coding for serine, to GCT, coding for alanine. This amino acid substitution has no apparent effect on the AKIII enzyme activity.

The lysC gene was cut out of plasmid pBT457 as a 1560 bp Nco I-EcoR I fragment and inserted into the expression vector pBT430 digested with the same enzymes, yielding plasmid pBT461. For expression of the mutant lysC-M4 gene pBT461 was digested with Kpn I-EcoR I, which removes the wild type lysC gene from about 30 nucleotides downstream from the translation start codon, and inserting the analogous Kpn I-EcoR I fragments from the mutant genes yielding plasmid pBT492.

Example 6

Molecular Cloning of Corn Genes Encoding Methionine-Rich Seed Storage Proteins

A high methionine 10 kD zein gene [Kirihara et al., Mol. Gen. Genet., (1988), 211, 477–484[ w]as isolated from corn genomic DNA using PCR. Two oligonucleotides 30 bases long flanking this gene were synthesized using an Applied Biosystems DNA synthesizer. Oligomer SM56 (SEQ ID NO:26) codes for the positive strand spanning the first ten amino acids:

SM56   5'-ATGGCAGCCA   AGATGCTTGC ATTGTTCGCT-3' SEQ ID NO:26

Oligomer CFC77 (SEQ ID NO:27) codes for the negative strand spanning the last ten amino acids:

CFC77   5'-GAATGCAGCA   CCAACAAAGG GTTGCTGTAA-3' SEQ ID NO:27

These were employed to generate by polymerase chain reaction (PCR) the 10 kD coding region using maize genomic DNA from strain B85 as the template. PCR was performed using a Perkin-Elmer Cetus kit according to the instructions of the vendor on a thermocycler manufactured by the same company. The reaction product, when run on a 1% agarose gel and stained with ethidium bromide, showed a strong DNA band of the size expected for the 10 kD zein gene, 450 bp, with a faint band at about 650 bp. The 450 bp band was electro-eluted onto DEAE cellulose membrane (Schleicher & Schuell) and subsequently eluted from the membrane at 65° C. with 1 M NaCl, 0.1 mM EDTA, 20 mM Tris-Cl, pH 8.0. The DNA was ethanol precipitated and rinsed with 70% ethanol and dried. The dried pellet was resuspended in 10 µL water and an aliquot (usually 1 µL) was used for another set of PCR reactions, to generate by asymmetric priming single-stranded linear DNAs. For this, the primers SM56 and CFC77 were present in a 1:20 molar ratio and 20:1 molar ratio. The products, both positive and negative strands of the 10 kD zein gene, were phenol extracted, ethanol precipitated, and passed through NACS (Bethesda Research Laboratories) columns to remove the excess oligomers. The eluates were ethanol precipitated twice, rinsed with 70% ethanol, and dried. DNA sequencing was done using the appropriate complementary primers and a sequenase kit from United States Biochemicals Company according to the vendors instructions. The sequence deviated from the published coding sequence (Kirihara et al., Gene, (1988), 71, 359–370) in one base pair at nucleotide position 1504 of the published sequence. An A was changed to a G which resulted in the change of amino acid 123 (with the initiator methionine as amino acid 1) from Gln to Arg. It is not known if the detected mutation was generated during the PCR reaction or if this is another allele of the maize 10 kD zein gene. A radioactive probe was made by nick-translation of the PCR-generated 10 kD zein gene using $^{32}$P-dCTP and a nick-translation kit purchased from Bethesda Research Laboratories.

A genomic library of corn in bacteriophage lambda was purchased from Clontech (Palo Alto, Calif.). Data sheets from the supplier indicated that the corn DNA was from seven-day-old seedlings grown in the dark. The vector was 1-EMBL-3 carrying BamHI fragments 15 kb in average size. A titer of 1 to 9×10$^9$ plaque forming units (pfu)/mL was indicated by the supplier. Upon its arrival the library was titered and contained 2.5×10$^9$ pfu/mL.

The protocol for screening the library by DNA hybridization was provided by the vendor. About 30,000 pfu were plated per 150-mnn plate on a total of 15 Luria Broth (LB) agar plates giving 450,000 plaques. Plating was done using E. coli LE392 grown in LB+0.2% maltose as the host and LB-7.2% agarose as the plating medium. The plaques were absorbed onto nitrocellulose filters (Millipore HATF, 0.45 mM pore size), denatured in 0.5M NaOH, neutralized in 1.5 M NaCl, 0.5 M Tris-Cl pH 7.5, and rinsed in 3×SSC [Sambrook et al. (1989) Molecular Cloning: A Laboratory Manual, Cold Spring Harbor Laboratory Press[2ea]The filters were blotted on Whatman 3 MM paper and heated in a vacuum oven at 80° C. for two hours to allow firm anchorage of phage DNA in the membranes.

The $^{32}$P-labelled 10 kD zein was used as a hybridization probe to screen the library. The fifteen 150-mm nitrocellulose filters carrying the 1 phage plaques were screened using radioactive 10 kD gene probe. After four hours prehybridizing at 60° C. in 50×SSPE, 5× Denhardt's, [see Sambrook et al. (1989) Molecular Cloning: A Laboratory Manual, Cold Spring Harbor Laboratory Press[ 0].1% SDS, 100 μg/mL calf thymus DNA, the filters were transferred to fresh hybridization mix containing the denatured radiolabeled 10 kD zein gene (cpm/mL) and stored overnight at 60° C. They were rinsed the following day under stringent conditions: one hour at room temp in 2×SSC—0.05% SDS and one hour at 68° C. in 1×SSC—0.1% SDS. Blotting on 3 MM Whatman paper followed, then air drying and autoradiography at −70° C. with Kodak XAR-5 films with DuPont Cronex® Lightning Plus intensifying screens. From these autoradiograms, 20 hybridizing plaques were identified. These plaques were picked from the original petri plate and plated out at a dilution to yield about 100 plaques per 80-mm plate. These plaques were absorbed to nitrocellulose filters and re-probed using the same procedure. After autoradiography only one of the original plaques, number 10, showed two hybridizing plaques. These plaques were tested with the probe a third time; all the progeny plaques hybridized, indicating that pure clones had been isolated.

DNA was prepared from these two phage clones, 10-1, 10-2, using the protocol for DNA isolation from small-scale liquid 1-phage lysates (Ansul et al. (1987) Current Protocols in Molecular Biology, pp. 1.12.2, 1.13.5–6). Restriction endonuclease digests and agarose gel electrophoresis showed the two clones to be identical. The DNA fragments from the agarose gel were "Southern-blotted" [see Sambrook et al. (1989) Molecular Cloning: A Laboratory Manual, Cold Spring Harbor Laboratory Press[ o]nto nitrocellulose membrane filters and probed with radioactively-labeled 10 kD zein DNA generated by nick translation. A single 7.5 kb BamH I fragment and a single 1.4 kb Xba I fragment hybridized to the probe.

The 7.5 kb BamH I fragment was isolated from a BamH I digest of the I DNA run on an 0.5% low melting point (LMP) agarose gel. The 7.5 kb band was excised, melted, and diluted into 0.5 M NaCl and loaded onto a NACS column, which was then washed with 0.5 M NaCl, 10 mM Tris-Cl, pH 7.2, 1 mM EDTA and the fragment eluted with 2 M NaCl, 10 mM Tris-Cl, pH 7.2, 1 mM EDTA. This fragment was ligated to the phagemid pTZ18R (Pharmacia) which had been cleaved with BamH I and treated with calf intestinal alkaline phosphatase [see Sambrook et al. (1989) Molecular Cloning: A Laboratory Manual, Cold Spring Harbor Laboratory Press[ t]o prevent ligation of the phagemid to itself. Subclones with these fragments in both orientations with respect to the pTZ18R DNA were obtained following transformation of E. coli.

An Xba I digest of the cloned I phage DNA was run on an 0.8% agarose gel and a 1.4 kb fragment was isolated using DEAE cellulose membrane (same procedure as for the PCR-generated 10 kD zein DNA fragment described above). This fragment was ligated to pTZ18R cut with Xba I in the same way as described above. Subclones with these fragments in both orientations with respect to the pTZ 18R DNA, designated pX8 and pX 10, were obtained following transformation of E. coli . Single-stranded DNAs were made from the subclones using the protocol provided by Pharmacia. The entire 1.4 kb Xba I fragments were sequenced. An additional 700 bases adjacent to the Xba I fragment was sequenced from the BamH I fragment in clone pB3 (fragment pB3 is in the same orientation as pX8) giving a total of 2123 bases of sequence (SEQ ID NO:28).

Encoded on this fragment is another methionine-rich zein, which is related to the 10 kD zein and has been designated High Sulfur Zein (HSZ) [see World Patent Publication No. WO 92/14822[. ]From the deduced amino acid sequence of the protein, its molecular weight is approximately 21 kD and it is about 38% methionine by weight.

Example 7

Modification of the HSZ Gene by Site-Directed Mutagenesis

Three Nco I sites were present in the 1.4 kD Xba I fragment carrying the HSZ gene, all in the HSZ coding region. It was desirable to maintain only one of these sites (nucleotides 751–756 in SEQ ID NO:28) that included the translation start codon. Therefore, the Nco I sites at positions 870–875 and 1333–1338 were eliminated by oligonucleotide-directed site-specific mutagenesis [see Sambrook et al. (1989) Molecular Cloning: A Laboratory Manual, Cold Spring Harbor Laboratory Press[. ]The oligonucleotides synthesized for the mutagenesis were:

CFC99    5'-ATGAACCCTT GGATGCA-3'    SEQ ID NO:30

CFC98    5'-CCCACAGCAA TGGCGAT-3'    SEQ ID NO:31

Mutagenesis was carried out using a kit purchased from Bio-Rad (Richmond, Calif.), following the protocol provided by the vendor.

The process changed the A to T at 872 and the C to A at 1334. These were both at the third position of their respective codons and resulted in no change in the amino acid sequence encoded by the gene, with C C A to C C T, still coding for Pro and G C C to G C A, still coding for Ala. The plasmid clone containing the modified HSZ gene with a single Nco I site at the ATG start codon was designated pX8m. Because the native HSZ gene has a unique Xba I site at the stop codon of the gene (1384–1389, SEQ ID NO:28), a complete digest of the DNA with Nco I and Xba I yields a 637 bp fragment containing the entire coding sequence of the precursor HSZ polypeptide (SEQ ID NO:32).

It was desirable to create a form of the HSZ gene with alternative unique restriction endonuclease sites just past the end of the coding region. To do this oligonucleotides CFC104 (SEQ ID NO:34) and CFC105 (SEQ ID NO:35):

CFC104    5'-CTAGCCCGGGTAC-3'    (SEQ ID NO:34)

CFC105    3'-GGGCCCATGGATC-5'    (SEQ ID NO:35)

were annealed and ligated into the Xba I site, introducing two new restriction sites, Sma I and Kpn I, and destroying the Xba I site. The now unique Xba I site from nucleotide 1–6 in SEQ ID NO:28 and the Ssp I site from nucleotide 1823–1828 in SEQ ID NO:28 were used to obtain a fragment that included the HSZ coding region plus its 5' and 3' regulatory regions. This fragment was cloned into the commercially-available vector pTZ19R (Pharmacia) digested with Xba I and Sma I, yielding plasmid pCC10.

It was desirable to create an altered form of the HSZ gene with a unique restriction endonuclease site at the start of the mature protein, i.e., with the amino terminal signal sequence removed. To accomplish this a DNA fragment was generated using PCR. Template DNA for the PCR reaction was plasmid pX8m. Oligonucleotide primers for the reaction were:

```
CFC106:
5'-CCACTTCATGACCCATATCCCAGGGCACTT-3' SEQ ID NO:36

CFC88:
5'-TTCTATCTAGAATGCAGCACCAACAAAGGG-3' SEQ ID NO:37
```

The CFC106 (SEQ ID NO:36) oligonucleotide provided the PCR-generated fragment with a BspH I site (underlined), which when digested with BspH I results in a cohesive-end identical to that generated by an Nco I digest. This site was located at the junction of the signal sequence and the mature HSZ coding sequence. The CFC88 (SEQ ID NO:37) oligonucleotide provided the PCR-generated fragment with an Xba I site (underlined) at the translation terminus of the HSZ gene. The BspH I-Xba I fragment (SEQ ID NO:38) obtained by digestion of the PCR-generated fragment, encodes the mature form of HSZ with the addition of a methionine residue at the amino terminus of the protein to permit initiation of translation.

Example 8

Construction of Chimeric Genes for Expression of CS, AKIII-M4, and HSZ Proteins in the Seeds of Monocot Plants The following chimeric genes were made for transformation into monocot plants:

globulin 1 promoter/mcts/lysC-M4/globulin 1 3' region globulin 1 promoter/corn CS coding region/globulin 1 3' region glutelin 2 promoter/mcts/lysC-M4/NOS 3' region glutelin 2 promoter/corn CS coding region/10 kD 3' region 10 kD promoter/HSZ coding region/10 kD 3' region glutelin 2 promoter/HSZ coding region/10 kD 3' region A gene expression cassette employing the 10 kD zein regulatory sequences includes about 925 nucleotides upstream (5') from the translation initiation codon and about 945 nucleotides downstream (3') from the translation stop codon. The entire cassette is flanked by an EcoR I site at the 5' end and BamH I, Sal I and Hind III sites at the 3' end. The DNA sequence of these regulatory regions have been described in the literature [Kirihara et al,. *Gene*, (1988), 71, 359–370[ a]nd DNA fragments carrying these regulatory sequences were obtained from corn genomic DNA via PCR. Between the 5' and 3' regions is a unique Nco I site, which includes the ATG translation initiation codon. The oligonucleotides CFC104 (SEQ ID NO:34) and CFC105 (SEQ ID NO:35) (see Example 7) were inserted at the Xba I site near the 10 kD zein translation stop codon, thus adding a unique Sma I site. An Nco I-Sma I fragment containing the HSZ coding region was isolated from plasmid pCC10 (see Example 7) and inserted into Nco I-Sma I digested 10 kD zein expression cassette creating the chimeric gene: 10 kD promoter/HSZ coding region/10 kD 3' region.

The glutelin 2 promoter was cloned from corn genomic DNA using PCR with primers based on the published sequence [Reina et al., *Nucleic Acids Res.*, (1990), 18, 6426–6426[. ]The promoter fragment includes 1020 nucleotides upstream from the ATG translation start codon. An Nco I site was introduced via PCR at the ATG start site to allow for direct translational fusions. A BamH I site was introduced on the 5' end of the promoter. The 1.02 kb BamH I to Nco I promoter fragment was linked to an Nco I to Hind III fragment carrying the HSZ coding region/10 kD 3' region described above yielding the chimeric gene: glutelin 2 promoter/HSZ coding region/10 kD 3' region in a plasmid designated pML103.

The globulin 1 promoter and 3' sequences were isolated from a Clontech corn genomic DNA library using oligonucleotide probes based on the published sequence of the globulin 1 gene [Kriz et al., *Plant Physiol.*, (1989), 91, 636[. ]The cloned segment includes the promoter fragment extending 1078 nucleotides upstream from the ATG translation start codon, the entire globulin coding sequence including introns and the 3' sequence extending 803 bases from the translational stop. To allow replacement of the globulin 1 coding sequence with other coding sequences an Nco I site was introduced at the ATG start codon, and Kpn I and Xba I sites were introduced following the translational stop codon via PCR to create vector pCC50. There is a second Nco I site within the globulin I promoter fragment. The globulin 1 gene cassette is flanked by Hind III sites.

Plant amino acid biosynthetic enzymes are known to be localized in the chloroplasts and therefore are synthesized with a chloroplast targeting signal. Bacterial proteins such as AKIII have no such signal. A chloroplast transit sequence (cts) was therefore fused to the lysC-M4 coding sequence in the chimeric genes described below. For corn the cts used was based on the the cts of the small subunit of ribulose 1,5-bisphosphate carboxylase from corn [Lebrun et al., *Nucleic Acids Res.*, (1987), 15, 4360[ a]nd is designated mcts. The oligonucleotides SEQ ID NOS:40–45 were synthesized and used to attach the mcts to lysC-M4.

Oligonucleotides SEQ ID NO:40 and SEQ ID NO:41, which encode the carboxy terminal part of the corn chloroplast targeting signal, were annealed, resulting in Xba I and Nco I compatible ends, purified via polyacrylamide gel electrophoresis, and inserted into Xba I plus Nco I digested pBT492 (see Example 5). The insertion of the correct sequence was verified by DNA sequencing yielding pBT556. Oligonucleotides SEQ ID NO:42 and SEQ ID NO:43, which encode the middle part of the chloroplast targeting signal, were annealed, resulting in Bgl II and Xba I compatible ends, purified via polyacrylamide gel electrophoresis, and inserted into Bgl II and Xba I digested pBT556. The insertion of the correct sequence was verified by DNA sequencing yielding pBT557. Oligonucleotides SEQ ID NO:44 and SEQ ID NO:45, which encode the amino terminal part of the chloroplast targeting signal, were annealed, resulting in Nco I and Afl II compatible ends, purified via polyacrylamide gel electrophoresis, and inserted into Nco I and Afl II digested pBT557. The insertion of the correct sequence was verified by DNA sequencing yielding pBT558. Thus the mcts was fused to the lysC-M4 gene.

To construct the chimeric gene: globulin 1 promoter/mcts/lysC-M4/globulin 1 3' region an Nco I to Hpa I fragment containing the mcts/lysC-M4 coding sequence was isolated from plasmid pBT558 and inserted into Nco I plus Sma I digested pCC50 creating plasmid pBT663.

To construct the chimeric gene: glutelin 2 promoter/mcts/lysC-M4/NOS 3' region the 1.02 kb BamH I to Nco I glutelin 2 promoter fragment described above was linked to the Nco I to Hpa I fragment containing the mcts/lysC-M4 coding sequence described above and to a Sma I to Hind III fragment carrying the NOS 3' region creating.

To construct the chimeric gene: globulin 1 promoter/corn CS coding region/globulin 1 3' region a 1482 base pair BspH I fragment containing the corn CS coding region (see Example 4) was isolated and inserted into an Nco I partial digest of pCC50. A plasmid designated pML157 carried the CS coding region in the proper orientation to create the indicated chimeric gene, as determined via restriction endonuclease digests.

To construct the chimeric gene: glutelin 2 promoter/corn CS coding region/10 kD 3' region the HSZ coding region was removed from pML103 (above) by digestion with Nco I and Xma I and insertion of an oligonucleotide adaptor containing an EcoR I site and Nco I and Xma I sticky ends. The resulting plasmid was digested with Nco I and the 1482 base pair BspH I fragment containing the corn CS coding region (see above and Example 4) was inserted. A plasmid with the CS coding region in the proper orientation, as determined via restriction endonuclease digests, was obtained, creating the indicated chimeric gene.

A corn CS gene that contained the entire chloroplast targeting signal was constructed by fusing the 5' end of the genomic CS gene to the 3' end of the cDNA. A 697 bp Nco I to Sph I genomic DNA fragment replaced the analogous Nco I to Sph I fragment in the cDNA. Thus, the first 168 amino acids are encoded by the genomic CS sequence and the coding sequence is interrupted by two introns. The remaining 341 amino acids are encoded by cDNA CS sequence with no further introns, resulting in a protein of 509 amino acids in length (SEQ ID NO:19): A 1750 bp Nco I to BspH I DNA fragment that includes the entire CS coding region was inserted into the corn embryo and endosperm expression cassettes resulting in the chimeric genes globulin I promoter/corn CS coding region/globulin 1 3' region in plasmid pFS1198 and glutelin 2 promoter/corn CS coding region/10 kD zein 3' region in plasmid pFS1196, respectively.

Example 9

Construction of Chimeric Genes for Expression of CS, AKIII-M4, and HSZ Proteins in the Seeds of Dicot Plants The following chimeric genes were made for transformation into dicot plants:

phaseolin promoter/scts/lysC-M4/phaseolin 3' region
KTI3 promoter/scts/corn CS coding region/KTI3 3' region
phaeolin promoter/HSZ coding region/phaseolin 3' region
β-conglycinin-conglycinin promoter/HSZ coding region/phaseolin 3' region A first seed-specific expression cassette used for expression in dicotyledonous plants is composed of the promoter and transcription terminator from the gene encoding the b subunit of the seed storage protein phaseolin from the bean *Phaseolus vulgaris* [Doyle et al. (1986) J. Biol. Chem. 261:9228–9238[. ]The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

A second seed-specific expression cassette used for expression in dicotyledonous plants is composed of the promoter from the α' subunit of soybean β-conglycinin (*Glycine max*) and the transcription terminator from the gene encoding the β subunit of the seed storage protein phaseolin from the bean *Phaseolus vulgaris* (above). The conglycinin cassette includes 607 nucleotides upstream (5') from the translation initiation codon of soybean β-conglycinin and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

A third seed-specific expression cassette used for expression in dicotyledonous plants is composed of the promoter and transcription terminator from the soybean Kunitz trysin inhibitor 3 (KTI3) gene [Jofuku et al., *Plant Cell*, (1989), 1, 427–435[. ]The KTI3 cassette includes about 2000 nucleotides upstream (5') from the translation initiation codon and about 240 nucleotides downstream (3') from the translation stop codon of phaseolin. Between the 5' and 3' regions are the unique restriction endonuclease sites Nco I (which includes the ATG translation initiation codon), Xba I, Kpn I and Sma I. The entire cassette is flanked by BamH I sites.

Plant amino acid biosynthetic enzymes are known to be localized in the chloroplasts and therefore are synthesized with a chloroplast targeting signal. Bacterial proteins such as AKIII have no such signal. A chloroplast transit sequence (cts) was therefore fused to the lysC-M4 coding sequence in some chimeric genes. The cts used was based on the the cts of the small subunit of ribulose 1,5-bisphosphate carboxylase from soybean [Berry-Lowe et al., *J. Mol. Appl. Genet.*, (1982), 1, 483–498[. ]The oligonucleotides SEQ ID NOS:46–51 were synthesized and used as described below. The soybean cts (scts) was also used to replace the native corn cts in the corn CS gene.

Oligonucleotides SEQ ID NO:46 and SEQ ID NO:47, which encode the carboxy terminal part of the chloroplast targeting signal, were annealed, resulting in Nco I compatible ends, purified via polyacrylamide gel electrophoresis, and inserted into Nco I digested pBT461. The insertion of the correct sequence in the correct orientation was verified by DNA sequencing yielding pBT496. Oligonucleotides SEQ ID NO:48 and SEQ ID NO:49, which encode the amino terminal part of the chloroplast targeting signal, were annealed, resulting in Nco I compatible ends, purified via polyacrylamide gel electrophoresis, and inserted into Nco I digested pBT496. The insertion of the correct sequence in the correct orientation was verified by DNA sequencing yielding pBT521. Thus the scts was fused to the lysC gene.

To fuse the scts to the lysC-M4 gene, pBT521 was digested with Sal I, and an approximately 900 bp DNA fragment that included the scts and the amino terminal coding region of lysC was isolated. This fragment was inserted into Sal I digested pBT492, effectively replacing the amino terminal coding region of lysC-M4 with the fused scts and the amino terminal coding region of lysC. Since the mutation that resulted in lysine-insensitivity was not in the replaced fragment, the new plasmid, pBT523, carried the scts fused to lysC-M4.

A 1600 bp Nco I-Hpa I fragment containing the cts fused to lysC-M4 plus about 90 bp of 3' non-coding sequence was isolated from pBT523 and inserted into the phaseolin seed-specific expression cassette digested with Nco I and Sma I, yielding plasmid pBT544 carrying the chimeric gene:

phaseolin promoter/scts/lysC-M4/phaseolin 3' region.

An scts DNA fragment that can be readily inserted into dicot gene expression cassettes vas created. Employing PCR with primers CF32 (SEQ ID NO:50) and CF33 (SEQ ID NO:51) and any template DNA carrying the soybean cts, e.g. pBT523 above, results in a DNA fragment carrying the entire scts. This fragment is then cut with Nco I and ligated to any gene that carries an Nco I site in-frame with the translation initiation codon.

The corn CS gene of plasmid pFS1088 (Example 3) was cut with restriction enzyme Sst II and the oligonucleotide adaptor shown in SEQ ID NO:52 was self-annealed and inserted. This removes most of the corn chloroplast transit peptide coding region and adds an Nco I site in-frame with the CS coding sequence. A DNA fragment containing the thus modified corn CS gene was was obtained by digestion with Nco I and BspH I and ligated into the KTI3 expression cassette digested with Nco I. Insertion of the corn CS gene in the proper orientation was determined by restriction enzyme mapping. The scts was then added as an Nco I fragment as described above yielding the chimeric gene: KTI3 promoter/scts/corn CS coding region/KTI3 3' region.

The Nco I-Xba I fragment containing the entire HSZ coding region (see Example 7) was isolated from an agarose gel following electrophoresis and inserted into the phaseolin and β-conglycinin expression cassettes which had been digested with Nco I-Xba I. Thus the two chimeric genes:

1) phaseolin 5' region/HSZ/phaseolin 3' region
2) β-conglycinin 5' region/HSZ/phaseolin 3' region were created.

Example 10

Isolation of the *E. coli* metL Gene and Construction of Chimeric Genes for Expression in the Seeds of Plants The metL gene of *E. coli* encodes a bifunctional protein, AKII-HDHII; the AK and HDH activities of this enzyme are insensitive to all pathway end-products. The metL gene of *E. coli* has been isolated and sequenced previously [Zakin et al., *J. Biol. Chem.*, (1983), 258, 3028–3031[. ]For the present invention a DNA fragment containing the metL gene was isolated and modified from *E. coli* genomic DNA obtained from strain LE392 using PCR. The following PCR primers were designed and synthesized:

```
                                          SEQ ID NO:53
CF23 5'-GAAACCATGG CCAGTGTGAT TGCGCAGGCA-3'

SEQ ID NO:54
CF24 5'-GAAAGGTACC TTACAACAAC TGTGCCAGC-3'
```

These primers add an Nco I site which includes a translation initiation codon at the amino terminus of the AKII-HDHII protein. In order to add the restriction site and additional codon, GCC coding for alanine, was also added to the amino terminus of the protein. The primers also add a Kpn I site immediately following the translation stop codon.

PCR was performed using a Perkin-Elmer Cetus kit according to the instructions of the vendor on a thermocycler manufactured by the same company. The primers were at a concentration of 10 mM and the thermocycling conditions were:

94° 1 min, 50° 2 min, 72° 8 min for 10 cycles followed by 94° 1 min, 72° 8 min for 30 cycles.

Reactions with four different concentrations of template DNA all yielded the expected 2.4 kb DNA fragment, along with several other smaller fragments. The four PCR reaction mixes were pooled, digested with Nco I and Kpn I and the 2.4 kb fragments were purified and isolated from an agarose gel. The fragment was inserted into a modified pBT430 expression vector (see Example 2) containing a Kpn I site downstream of the Nco I site at the translation initiation codon. DNA was isolated from 8 clones carrying the 2.4 kb fragment in the pBT430 expression vector and transformed into the expression host strain BL21(DE3). Cultures were grown in TB medium containing ampicillin (100 mg/L) at 37° C. overnight. The cells were collected by centririgation and resuspended in ½5th the original culture volume in 50 mM NaCl; 50 mM Tris-Cl, pH 7.5; 1 mM EDTA, and frozen at −20° C., thawed at 37° C. and sonicated, in an ice-water bath, to lyse the cells. The lysate was centrifuged at 4° C. for 5 min at 12,000 rpm. The supernatant was removed and the pellet was resuspended in the above buffer. The supernatant fractions were assayed for HDH enzyme activities to identify clones expressing functional proteins. HDH activity was assayed as shown below:

HDH ASSAY

| Stock solutions | 1.0 µl | 0.20 µl | Final conc |
|---|---|---|---|
| 0.2 M KPO$_4$, pH 7.0 | 500 µl | 100 µl | 100 mM |
| 3.7 M KCl | 270 µl | 54 µl | 1.0 M |
| 0.5 M EDTA | 20 µl | 4 µl | 10 mM |
| 1.0 M MgCl$_2$ | 10 µl | 2 µl | 10 mM |
| 2 mM NADPH | 100 µl | 20 µl | 0.20 mM |

Make Mixture of above reagents with amounts multiplied by number of assays. Use 0.9 mL of mix for 1 mL assay; 180 µL of mix for 0.2 mL assay in microtiter dish

| Add | | | |
|---|---|---|---|
| 1.0 M ASA in 1.0 N HCl | 1 µl | 0.2 µl | 1.0 mM | to ½ the assay mix; remaining ½ lacks ASA to serve as blank

| enzyme extract | 10–100 µl | 2–20 µl |
|---|---|---|
| H$_2$O | to 1.0 mL | to 0.20 mL |

Add enzyme extract last to start reaction. Incubate at ~30° C.; monitor NADPH oxidation at 340 nM. 1 unit oxidizes 1 µmol NADPH/min at 30° C. in the 1 mL reaction.

Four of eight extracts showed HDH activity well above the control. These four were then assayed for AK activity. AK activity was assayed as shown below:

AK ASSAY

Assay mix (for 12×1.0 mL or 48×0.25 mL assays):

2.5 mL H$_2$O
2.0 mL 4M KOH
2.0 mL 4M NH$_2$OH—HCl
1.0 mL 1M Tris-HCl pH 8.0
0.5 mL 0.2M ATP (121 mg/ml in 0.2M NaOH)
50 µL 1M MgSO$_4$
pH of assay mix should be 7–8

Each 1.5 mL eppendorf assay tube contains:

| | MACRO assay | micro assay |
|---|---|---|
| assay mix | 0.64 mL | 0.16 mL |
| 0.2 M L-Aspartate | 0.04 mL | 0.01 mL |
| extract | 5–120 µL | 1–30 µl |
| H$_2$0 to total vol. | 0.8 mL | 0.2 mL |

Assay tubes are incubated at 30° C. for 30–60 min

Add to develop color;

| FeCl₃ reagent | 0.4 mL | 0.1 mL |
|---|---|---|
| FeCl₃ reagent is: | 10% w/v FeCl₃ | 50 g |
| | 3.3% TCA | 15.5 g |
| | 0.7% HCl | 35 mL HCl |
| | | H₂O to 500 mL |

Spin for 2 min in eppendorf centrifuge tube.
Read OD at 540 run.

Two extracts also had high levels of AK enzyme activity. These two extracts were then tested for inhibition of AK or HDH activity by the pathway end-products, lys, thr and met. Neither the AK nor the HDH activity of the extract from clone 5 was inhibited by 30 mM concentrations of any of the end-products.

The supernatant and pellet fractions of several of the extracts were also analyzed by SDS polyacrylamide gel electrophoresis. In the extract-from clone 5, the major protein visible by Coomassie blue staining in both the pellet and supernatant fractions had a molecular weight of about 85 kd, the expected size for AKII-HDHII. The metL gene in plasmid pBT718 from clone 5 was used for all subsequent work.

Plant amino acid biosynthetic enzymes are known to be localized in the chloroplasts and therefore are synthesized with a chloroplast targeting signal. Bacterial proteins have no such signal. A chloroplast transit sequence (cts) was therefore fused to the metL coding sequence in the chimeric genes described below. For corn the cts used was based on the the cts of the small subunit of ribulose 1,5-bisphosphate carboxylase from corn [Lebrun et al. (1987) *Nucleic Acids Res.* 15:4360[ a]nd is designated mcts.

Oligonucleotides SEQ ID NO:40 and SEQ ID NO:41, which encode the carboxy terminal part of the corn chloroplast targeting signal, were annealed, resulting in Xba I and Nco I compatible ends, puyified via polyacrylamide gel electrophoresis, and inserted into Xba I plus Nco I digested pBT718. The insertion of the correct sequence was verified by DNA sequencing yielding pBT725. To complete the corn chloroplast targeting signal, pBT725 was digested with Bgl II and Xba I, and a 1.14 kb BamH I to Xba I fragment from pBT580 containing the glutelin 2 promoter plus the amino terminal part of the corn chloroplast targeting signal was inserted creating pBT726.

To construct the chimeric gene:
globulin 1 promoter/mcts/metL/globulin 1 3' region the 2.6 kb Nco I to Kpn I fragment containing the mcts/metL coding sequence was isolated from plasmid pBT726 and inserted into Nco I plus Kpn I digested pCC50 creating plasmid pBT727.

To construct the chimeric gene:
glutelin 2 promoter/mcts/metL/NOS 3' region the 2.6 kb Nco I to Kpn I fragment containing the mcts/metL coding sequence was isolated from plasmid pBT726 and linked to the 1.02 kb BamH I to Nco I glutelin 2 promoter fragment described in Example 8 and to a Kpn I to Hind III fragment carrying the NOS 3' region creating plasmid pBT728.

To construct the chimeric gene:
phaseolin promoter/scts/metL/phaseolin 3' region the 2.4 kb Nco I to Kpn I fragment containing the metL coding sequence was isolated from plasmid pBT718 and inserted into Nco I plus Kpn I digested phaseolin expression cassette. The scts was then added as an Nco I fragment as described in Example 8.

Example 11

Construction of Chimeric MS Genes for Expression in the Seeds of Plants

The following chimeric genes were made for transformation into monocot plants:
globulin 1 promoter/tobacco MS coding region/globulin 1 3' region;
glutelin 2 promoter/tobacco MS coding region/NOS 3' region.

To construct the chimeric gene:
globulin 1 promoter/tobacco MS coding region/globulin 1 3' region, the 2300 bp BspH I-Kpn I fragment containing the tobacco MS coding sequence was isolated from plasmid pBT773 and inserted into Nco I plus Kpn I digested pCC50 (Example 8).

To construct the chimeric gene: p1 glutelin 2 promoter/tobacco MS coding region/NOS 3' region, the 2300 bp BspH I-Kpn I fragment containing the tobacco MS coding sequence was isolated from plasmid pBT773 and linked to the 1.02 kb BamH I to Nco I glutelin 2 promoter fragment described in Example 8 and to a Kpn I to Hind III fragment carrying the NDS 3' region.

The following chimeric gene was made for transformation into dicot plants:
KTI3 promoter/tobacco MS coding region/KTI3 3' region.

To construct the chimeric gene:
KTI3 promoter/tobacco MS coding region/KTI3 3' region, the 2300 bp BspH I-Kpn I fragment containing the tobacco MS coding sequence was isolated from plasmid pBT773 and inserted into the Nco I plus Kpn I digested KTI3 expression cassette described in Example 9.

Example 12

Evaluating Compounds for Their Ability to Inhibit the Activity of Methionine Synthase The plant methionine synthases described herein may be produced using any number of methods known to those skilled in the art. Such methods include, but are not limited to, expression in bacteria as described in Example 2, or expression in eukaryotic cell culture, in planta, and using viral expression systems in suitably infected organisms or cell lines. The instant plant methionine synthases may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant plant methionine synthases, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant plant methionine synthase is expressed as fusion protein, the purification protocol may include the use of an affinity resin which is specific for the fusion protein tag attached to the expressed enzyme or an affinity resin containing ligands which are specific for the enzyme. For example, the instant plant methionine synthase may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond T affinity resin or other resin.

Crude, partially purified or purified enzyme, either alone or as a fusion protein, may be utilized in assays for the evaluation of compounds for their ability to inhibit enzymatic activation of the instant plant methionine synthase disclosed herein. Assays may be conducted under well known experimental conditions which permit optimal enzymatic activity. For example, assays for methionine synthase are presented by Eichel et al. (1995) *Eur J Biochem* 230:1053–1058.

What is claimed is:

1. An isolated nudeic acid fragment comprising:
   (a) a nucleotide sequence encoding a polypeptide having methionine synthase activity, wherein the amino acid sequence of the polypeptide and the amino acid sequence of SEQ ID NO: 2 or 4 have at least 90% sequence identity based on the Clustal alignment method with default parameters, or
   (b) the full complement of the nucleotide sequence of (a).

2. The isolated nucleic acid fragment of claim 1, wherein the amino acid sequence of the polypeptide and the amino acid sequence of SEQ ID NO:2 or 4 have at least 95% sequence identity based on the Clustal alignment method.

3. The isolated nucleic acid fragment of claim 1, wherein the polypeptide comprises the amino acid sequence of SEQ ID NO:2 or 4.

4. The isolated nucleic acid fragment of claim 1, wherein the nucleotide sequence comprises the nucleotide sequence of SEQ ID NO:1 or 3.

5. A vector comprising the isolated nucleic acid fragment of claim 1.

6. A recombinant DNA construct comprising the isolated nucleic acid fragment of claim 1 operably linked to at least one regulatory sequence.

7. A method for producing a plant comprising transforming a plant cell with the isolated nucleic acid fragment of claim 1 and regenerating a plant from the transformed plant cell.

8. A method for isolating a polypeptide encoded by the isolated nucleic acid fragment of claim 1 comprising isolating the polypeptide from a cell containing a recombinant DNA construct comprising the polynucleotide operably linked to at least one regulatory sequence.

9. A method for transforming a cell comprising transforming a cell with the isolated nucleic acid fragment of claim 6.

10. A cell comprising the recombinant DNA construct of claim 6.

11. A plant comprising the recombinant DNA construct of claim 6.

12. A seed comprising the recombinant DNA construct of claim 6.

13. A method for increasing methionine content of the seeds of plants comprising:
   (a) transforming plant cells with the recombinant DNA construct of claim 6;
   (b) growing fertile mature plants from the transformed plant cells obtained from step (a) under conditions suitable to obtain seeds; and
   (c) selecting progeny seed of step (b) for those seeds containing increased levels of methionine compared to untransformed seeds.

14. A method for producing plant methionine synthase comprising:
   (a) transforming microbial host cells with the recombinant DNA construct of claim 6;
   (a) growing the transformed microbial cells obtained from step (a) under conditions that result in expression of the methionine synthase protein.

15. A method for increasing methionine content of the seeds of plants comprising:
   (a) transforming plant cells with the recombinant DNA contruct of claim 6;
   (b) growing fertile mature plants from the transformed plant cells obtained from step (a) under conditions suitable to obtain seeds; and
   (c) selecting progeny seed of step (b) for those seeds containing increased levels of methionine compared to untransformed seeds.

* * * * *

SEQUENCE LISTING

<160> NUMBER OF SEQ ID NOS: 55

<210> SEQ ID NO 1
<211> LENGTH: 2639
<212> TYPE: DNA
<213> ORGANISM: Zea mays

<400> SEQUENCE: 1

```
caccacccac ctcccactcc cagttcaccc cgtcgtcctc ggcgccacca ctcctcgtcc      60
cccggcgcta ctcccccgct ccacggtcca aggaaagatg gcgtcccata ttgttggata     120
ccctcgcatg ggccccaaga gggagctcaa gtttgccttg gagtctttct gggatgggaa     180
gagcagcgcc gaggatttgg agaaagttgc cactgacctg aggtctagca tctggaagca     240
aatgtcagaa gctgggatca agtacattcc cagcaatacc tcgtcgtact acgaccaggt     300
tcttgatacc acggccatgc ttggcgctgt cccagagcgc tactcttgga ctggaggcga     360
gattggcttg agcaccctact tctctatggc caggggaaat gccactgtcc ctgccatgga     420
gatgaccaag tggtttgata caaactacca ctttattgtc cctgaacttg gtccaagcac     480
caagttcaca tacgcttctc acaaggctgt ttctgagtac aaggaggcaa aggcgctcgg     540
cattgataca gtcccagtgc ttgttggacc agtctcatac ttgctcctct ctaagcctgc     600
caagggtgtg gagaaatctt tctctcttct ttcacttctt ggtagcattc ttcccatcta     660
caaggaggtt gttgctgagc tgaaggcagc tggtgcttca tggattcagc ttgatgagcc     720
taccttgtt aaagaccttg atgctcacga attggccgca ttctcttcag catatgctga     780
actggagtca tcgttctctg gattgaatgt gcttatcgag acatacttcg ctgatattcc     840
tgctgagtcc tacaagaccc tcacatcatt gagtggtgtg actgcttacg gtttcgatct     900
tatccgtgga gccaagaccc ttgatcttat caggagcagc ttcccctctg ggaagtacct     960
cttcgctggt gttgtagatg gacgcaacat ttgggctgat gatcttgctg catctcttag    1020
cactcttcat tctcttgagg ctgttgctgg caaggacaaa cttgtggtgt caacctcctg    1080
ctcactgatg cacaccgctg ttgaccttgt aaatgagact aagctggatg atgagattaa    1140
gtcatggctt gcatttgctg cccaaaaggt tgttgaggtt aatgcccttg ccaaggcttt    1200
ggcaggccaa aaggatgagg tctactttgc agccaatgct gctgctcagg cctcaaggag    1260
atcatcgccc agggtgacaa acgaggaggt ccagaaggct gcagctgctt tgagggatc    1320
tgaccaccgc cgttctacca ctgtttctgc tagattggat gctcagcaga aaagctcaa    1380
```

```
cctccctgtc cttcccacaa ccacaattgg ttcattccct cagactgtgg aactcaggag    1440
ggttcgccgt gaatacaagg caaagaagat caccgaggac gaatacatca gtgccatcaa    1500
ggaagaaatc agcaaggtcg tcaagatcca agaggagctt gacattgatg tgcttgtgca    1560
tggagagcca gagagaaatg acatggttga gtacttcggt gagcaattat ctggttttgc    1620
gttcactgcc aacggatggg tgcaatccta tggatcacgc tgtgtgaagc cacccattat    1680
ctacggtgat gtcagccggc cgaaccccat gactgttttc tggtccaaga tggcacagag    1740
catgacccct cgtcccatga agggaatgtt gactggtccg gtcacaatcc tcaactggtc    1800
attcgtcagg aacgaccagc ctaggtttga catgctac caaatagctc ttgcaatcaa     1860
aaaggaggtt gaggatcttg aggctgctgg tattcaggtg atccagatcg atgaggcagc    1920
tctaagggag ggtctgccac tacgcaagtc agagcatgca ttctacctgg actgggctgt    1980
ccactctttc aggatcacca actgcggagt ccaggacacc acccagatcc acacccacat    2040
gtgctactcc aacttcaacg acatcatcca ctccatcatc gacatggatg ccgatgtgat    2100
cacgatcgag aactcccggt ctgacgagaa gctactgtcc gtcttccgtg agggtgtgaa    2160
gtacggagct ggcattggcc ctggtgtcta cgacatccac tctcctagga ttccctccac    2220
agaggagatc gcagaccgcg tcgagaagat gctcgccgtg ttcgacacca acatcctctg    2280
ggtgaaccct gactgtggtc tcaagacacg caagtacacg gaggtcaagc ccgccctgac    2340
caacatggtc tcggccacca agctcatccg cacccagctt gccagcgcga atgaggtcg    2400 tttgatagct ccatggtctg atagcgcgga atgagccagt tgtttttgaat aatttgggtg   2460 ttaccccctg ttccatggtg ttagtgttag gttagcctct cattggtgag atacgccgtt    2520
tcaagatgtg ttctaagttt ggagtgtgtg ttttcctttg ggctatgttt ctggggtat    2580 gtgtgtgctt tggttataaa cagaaatgaa atatgcagtc ttccaattga aaaaaaaaa    2639
```

<210> SEQ ID NO 2
<211> LENGTH: 765
<212> TYPE: PRT
<213> ORGANISM: Zea mays

<400> SEQUENCE: 2

```
Met Ala Ser His Ile Val Gly Tyr Pro Arg Met Gly Pro Lys Arg Glu
 1               5                  10                  15

Leu Lys Phe Ala Leu Glu Ser Phe Trp Asp Gly Lys Ser Ser Ala Glu
                20                  25                  30

Asp Leu Glu Lys Val Ala Thr Asp Leu Arg Ser Ser Ile Trp Lys Gln
            35                  40                  45

Met Ser Glu Ala Gly Ile Lys Tyr Ile Pro Ser Asn Thr Ser Ser Tyr
        50                  55                  60

Tyr Asp Gln Val Leu Asp Thr Thr Ala Met Leu Gly Ala Val Pro Glu
 65                  70                  75                  80

Arg Tyr Ser Trp Thr Gly Gly Glu Ile Gly Leu Ser Thr Tyr Phe Ser
                 85                  90                  95

Met Ala Arg Gly Asn Ala Thr Val Pro Ala Met Glu Met Thr Lys Trp
            100                 105                 110

Phe Asp Thr Asn Tyr His Phe Ile Val Pro Glu Leu Gly Pro Ser Thr
        115                 120                 125

Lys Phe Thr Tyr Ala Ser His Lys Ala Val Ser Glu Tyr Lys Glu Ala
    130                 135                 140

Lys Ala Leu Gly Ile Asp Thr Val Pro Val Leu Val Gly Pro Val Ser
145                 150                 155                 160
```

-continued

```
Tyr Leu Leu Leu Ser Lys Pro Ala Lys Gly Val Glu Lys Ser Phe Ser
            165                 170                 175

Leu Leu Ser Leu Leu Gly Ser Ile Leu Pro Ile Tyr Lys Glu Val Val
        180                 185                 190

Ala Glu Leu Lys Ala Ala Gly Ala Ser Trp Ile Gln Leu Asp Glu Pro
    195                 200                 205

Thr Leu Val Lys Asp Leu Asp Ala His Glu Leu Ala Ala Phe Ser Ser
210                 215                 220

Ala Tyr Ala Glu Leu Glu Ser Ser Phe Ser Gly Leu Asn Val Leu Ile
225                 230                 235                 240

Glu Thr Tyr Phe Ala Asp Ile Pro Ala Glu Ser Tyr Lys Thr Leu Thr
                245                 250                 255

Ser Leu Ser Gly Val Thr Ala Tyr Gly Phe Asp Leu Ile Arg Gly Ala
            260                 265                 270

Lys Thr Leu Asp Leu Ile Arg Ser Ser Phe Pro Ser Gly Lys Tyr Leu
        275                 280                 285

Phe Ala Gly Val Val Asp Gly Arg Asn Ile Trp Ala Asp Asp Leu Ala
    290                 295                 300

Ala Ser Leu Ser Thr Leu His Ser Leu Glu Ala Val Ala Gly Lys Asp
305                 310                 315                 320

Lys Leu Val Val Ser Thr Ser Cys Ser Leu Met His Thr Ala Val Asp
                325                 330                 335

Leu Val Asn Glu Thr Lys Leu Asp Asp Glu Ile Lys Ser Trp Leu Ala
            340                 345                 350

Phe Ala Ala Gln Lys Val Val Glu Val Asn Ala Leu Ala Lys Ala Leu
        355                 360                 365

Ala Gly Gln Lys Asp Glu Val Tyr Phe Ala Ala Asn Ala Ala Ala Gln
    370                 375                 380

Ala Ser Arg Arg Ser Ser Pro Arg Val Thr Asn Glu Glu Val Gln Lys
385                 390                 395                 400

Ala Ala Ala Ala Leu Arg Gly Ser Asp His Arg Arg Ser Thr Thr Val
                405                 410                 415

Ser Ala Arg Leu Asp Ala Gln Gln Lys Lys Leu Asn Leu Pro Val Leu
            420                 425                 430

Pro Thr Thr Thr Ile Gly Ser Phe Pro Gln Thr Val Glu Leu Arg Arg
        435                 440                 445

Val Arg Arg Glu Tyr Lys Ala Lys Lys Ile Thr Glu Asp Glu Tyr Ile
    450                 455                 460

Ser Ala Ile Lys Glu Glu Ile Ser Lys Val Val Lys Ile Gln Glu Glu
465                 470                 475                 480

Leu Asp Ile Asp Val Leu Val His Gly Glu Pro Glu Arg Asn Asp Met
                485                 490                 495

Val Glu Tyr Phe Gly Glu Gln Leu Ser Gly Phe Ala Phe Thr Ala Asn
            500                 505                 510

Gly Trp Val Gln Ser Tyr Gly Ser Arg Cys Val Lys Pro Pro Ile Ile
        515                 520                 525

Tyr Gly Asp Val Ser Arg Pro Asn Pro Met Thr Val Phe Trp Ser Lys
    530                 535                 540

Met Ala Gln Ser Met Thr Pro Arg Pro Lys Gly Met Leu Thr Gly
545                 550                 555                 560

Pro Val Thr Ile Leu Asn Trp Ser Phe Val Arg Asn Asp Gln Pro Arg
                565                 570                 575
```

```
Phe Glu Thr Cys Tyr Gln Ile Ala Leu Ala Ile Lys Lys Glu Val Glu
            580                 585                 590

Asp Leu Glu Ala Ala Gly Ile Gln Val Ile Gln Ile Asp Glu Ala Ala
        595                 600                 605

Leu Arg Glu Gly Leu Pro Leu Arg Lys Ser Glu His Ala Phe Tyr Leu
    610                 615                 620

Asp Trp Ala Val His Ser Phe Arg Ile Thr Asn Cys Gly Val Gln Asp
625                 630                 635                 640

Thr Thr Gln Ile His Thr His Met Cys Tyr Ser Asn Phe Asn Asp Ile
                645                 650                 655

Ile His Ser Ile Ile Asp Met Asp Ala Asp Val Ile Thr Ile Glu Asn
            660                 665                 670

Ser Arg Ser Asp Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
    690                 695                 700

Ile Pro Ser Thr Glu Glu Ile Ala Asp Arg Val Glu Lys Met Leu Ala
705                 710                 715                 720

Val Phe Asp Thr Asn Ile Leu Trp Val Asn Pro Asp Cys Gly Leu Lys
                725                 730                 735

Thr Arg Lys Tyr Thr Glu Val Lys Pro Ala Leu Thr Asn Met Val Ser
            740                 745                 750

Ala Thr Lys Leu Ile Arg Thr Gln Leu Ala Ser Ala Lys
        755                 760                 765

<210> SEQ ID NO 3
<211> LENGTH: 2443
<212> TYPE: DNA
<213> ORGANISM: Glycine max
<220> FEATURE:
<221> NAME/KEY: unsure
<222> LOCATION: (460)
<223> OTHER INFORMATION: n = A, C, G, or T
<220> FEATURE:
<221> NAME/KEY: unsure
<222> LOCATION: (2398)
<223> OTHER INFORMATION: n = A, C, G, or T
<220> FEATURE:
<221> NAME/KEY: unsure
<222> LOCATION: (2442)
<223> OTHER INFORMATION: n = A, C, G, or T

<400> SEQUENCE: 3
ccctcagaag cgaagaagaa gccacagaga accagtctcc tactctctct cacccacaag      60
aaaaatggca tctcacatcg ttggataccc ccgcatgggt cccaagagag agctcaagtt     120
cgctctcgag tctttctggg atggcaagag cagcgccgag gatttgcaga aggtggctgc     180
tgatctcagg tcatccatct ggaagcagat ggctggtgct gggatcaagt acatccccag     240
caacactttc tcgttctatg accagctgct cgacgccacc gccaccctcg gtgccgtccc     300
ccccaggtac ggctggaccg gcggcgagat tggattcgac acctacttct ccatggccag     360
aggtaatgct accgtgcctg ctatggagat gaccaagtgg ttcgacacca actaccactt     420
tattgtccct gaattgggcc ctgatgtgaa cttcacctan gcttctcaaa aggctgttga     480
tgaatacaag gaggccaagg cgcttggagt ggataccatt cccgtactcg ttggccctgt     540
tacatacttg ttgctctcca agcctgccaa gggagtcgag aaatcctttt ctctcctctc     600
tctccttccc aaggttcttg ctgtctacaa ggaagttatt gctgacccta aggcagctgg     660
tgcttcatgg attcaatttg atgagcctac ccttgtcttg gaccttgaat ctcacaagtt     720
```

-continued

```
gcaagctttc actgacgcat atgcagaact tgcacctgct tgtctgatc tgaatgttct    780
tgttgagacc tactttgctg acatccctgc tgaggcgtac aagaccctca catctctgaa    840
tggcgtcact gcatatgggt ttgatttggt ccgtggaacc catactcttg atttgatcaa    900
gggtggattt cccagtggaa atacctctt tgctggagtg gttgatggaa ggaacatctg     960
ggccaatgac cttgctgctt ctctcactac attgcaggt cttgagggca ttgtgggcaa    1020
agataagctt gttgtgtcca cctcctcctc ccttcttcac actgctgttg atcttgttaa   1080
cgagaccaag ttggatgacg agatcaagtc atggctagca tttgctgcac aaaaaattgt   1140
tgaagttaac gcattggcta aggcattgtc tggcaacaag gatgtggcct tcttctctgc   1200
taatgctgca gctcaggctt caaggaagtc ctctccaaga gtgaccaacg aggctgttca   1260
gaaggctgct gctgcattga agggttcaga tcatcgccgt gcaacaaatg tcagtgccag   1320
actggatgct caacaaaaga agctcaacct tccaatcctt ccaaccacca ctattggatc   1380
cttccctcag actgtagaac tgaggagggt acgccgtgag ttcaaggcta acaagatctc   1440
cgaggaagag tatgttaagt caattaagga ggaaattcgc aaagttgttg aacttcaaga   1500
agagcttgat attgatgttc ttgttcatgg agaaccagag aaaatgata tggttgagta    1560
cttcggtgag caattgtcag gctttgcctt cactgttaat gggtgggtgc aatcctatgg   1620
ttcccgttgt gtgaagccac caatcatcta tggtgatgtg agccgcccaa agccaatgac   1680
tgtcttctgg tcatctctgg ctcagagctt taccaagcgc ccaatgaagg gaatgcttac   1740
cggtcctgtt accattctca actggtcctt tgttagaaat gaccaaccta gatctgagac   1800
cacctaccag attgctttgg ctatcaagga cgaagtggag gaccttgaaa aggctggcat   1860
cactgttatc caaattgatg aagctgcttt gagagagggt ctgccactga ggaaatcaga   1920
acaagctcac tacttggact gggctgtcca tgccttcaga atcaccaatg ttggtgtgca   1980
ggataccact cagatccaca cccacatgtg ctactccaac ttcaacgaca tcatccactc   2040
catcatcgac atggacgctg atgttatcac cattgagaac tctcgctccg atgagaagct   2100
cctgtcagtc ttccgtgaag gtgtgaagta tggtgctgga attggccctg tgtctatga    2160
catccactcc ccaagaatac caccaactga agaaatcgct gacagaatca ataagatgct   2220
tgcagtgctc gagaagaaca tcttgtgggt caaccctgac tgtggtctca agacccgcaa   2280
gtacactgaa gtgaagccgc cctcacaaaa catggttgcc gcagcaaaac tcatccgtta   2340
cgaacttgcc aagtgaatgg tataagaaag tagaatctac aagttcaatg ggtccgcntt   2400
taaaatacac caaagaaaaa ttttcaaaat gggttgttca ana                     2443
```

<210> SEQ ID NO 4
<211> LENGTH: 763
<212> TYPE: PRT
<213> ORGANISM: Glycine max
<220> FEATURE:
<221> NAME/KEY: UNSURE
<222> LOCATION: (132)
<223> OTHER INFORMATION: Xaa = any amino acid

<400> SEQUENCE: 4

Met Ala Ser His Ile Val Gly Tyr Pro Arg Met Gly Pro Lys Arg Glu
 1               5                  10                  15

Leu Lys Phe Ala Leu Glu Ser Phe Trp Asp Gly Lys Ser Ser Ala Glu
            20                  25                  30

Asp Leu Gln Lys Val Ala Ala Asp Leu Arg Ser Ser Ile Trp Lys Gln
        35                  40                  45

```
Met Ala Gly Ala Gly Ile Lys Tyr Ile Pro Ser Asn Thr Phe Ser Phe
        50                  55                  60

Tyr Asp Gln Leu Leu Asp Ala Thr Ala Thr Leu Gly Ala Val Pro Pro
 65                  70                  75                  80

Arg Tyr Gly Trp Thr Gly Gly Glu Ile Gly Phe Asp Thr Tyr Phe Ser
                 85                  90                  95

Met Ala Arg Gly Asn Ala Thr Val Pro Ala Met Glu Met Thr Lys Trp
            100                 105                 110

Phe Asp Thr Asn Tyr His Phe Ile Val Pro Glu Leu Gly Pro Asp Val
        115                 120                 125

Asn Phe Thr Xaa Ala Ser Gln Lys Ala Val Asp Glu Tyr Lys Glu Ala
    130                 135                 140

Lys Ala Leu Gly Val Asp Thr Ile Pro Val Leu Val Gly Pro Val Thr
145                 150                 155                 160

Tyr Leu Leu Leu Ser Lys Pro Ala Lys Gly Val Glu Lys Ser Phe Ser
                165                 170                 175

Leu Leu Ser Leu Leu Pro Lys Val Leu Ala Val Tyr Lys Glu Val Ile
            180                 185                 190

Ala Asp Leu Lys Ala Ala Gly Ala Ser Trp Ile Gln Phe Asp Glu Pro
        195                 200                 205

Thr Leu Val Leu Asp Leu Glu Ser His Lys Leu Gln Ala Phe Thr Asp
210                 215                 220

Ala Tyr Ala Glu Leu Ala Pro Ala Leu Ser Asp Leu Asn Val Leu Val
225                 230                 235                 240

Glu Thr Tyr Phe Ala Asp Ile Pro Ala Glu Ala Tyr Lys Thr Leu Thr
                245                 250                 255

Ser Leu Asn Gly Val Thr Ala Tyr Gly Phe Asp Leu Val Arg Gly Thr
            260                 265                 270

His Thr Leu Asp Leu Ile Lys Gly Gly Phe Pro Ser Gly Lys Tyr Leu
        275                 280                 285

Phe Ala Gly Val Val Asp Gly Arg Asn Ile Trp Ala Asn Asp Leu Ala
290                 295                 300

Ala Ser Leu Thr Thr Leu Gln Gly Leu Glu Gly Ile Val Gly Lys Asp
305                 310                 315                 320

Lys Leu Val Val Ser Thr Ser Ser Ser Leu Leu His Thr Ala Val Asp
                325                 330                 335

Leu Val Asn Glu Thr Lys Leu Asp Asp Glu Ile Lys Ser Trp Leu Ala
            340                 345                 350

Phe Ala Ala Gln Lys Ile Val Glu Val Asn Ala Leu Ala Lys Ala Leu
        355                 360                 365

Ser Gly Asn Lys Asp Val Ala Phe Phe Ser Ala Asn Ala Ala Ala Gln
370                 375                 380

Ala Ser Arg Lys Ser Ser Pro Arg Val Thr Asn Glu Ala Val Gln Lys
385                 390                 395                 400

Ala Ala Ala Ala Leu Lys Gly Ser Asp His Arg Arg Ala Thr Asn Val
                405                 410                 415

Ser Ala Arg Leu Asp Ala Gln Gln Lys Lys Leu Asn Leu Pro Ile Leu
            420                 425                 430

Pro Thr Thr Thr Ile Gly Ser Phe Pro Gln Thr Val Glu Leu Arg Arg
        435                 440                 445

Val Arg Arg Glu Phe Lys Ala Asn Lys Ile Ser Glu Glu Glu Tyr Val
450                 455                 460
```

```
Lys Ser Ile Lys Glu Glu Ile Arg Lys Val Val Glu Leu Gln Glu Glu
465                 470                 475                 480

Leu Asp Ile Asp Val Leu Val His Gly Glu Pro Glu Arg Asn Asp Met
            485                 490                 495

Val Glu Tyr Phe Gly Glu Gln Leu Ser Gly Phe Ala Phe Thr Val Asn
        500                 505                 510

Gly Trp Val Gln Ser Tyr Gly Ser Arg Cys Val Lys Pro Pro Ile Ile
    515                 520                 525

Tyr Gly Asp Val Ser Arg Pro Lys Pro Met Thr Val Phe Trp Ser Ser
530                 535                 540

Leu Ala Gln Ser Phe Thr Lys Arg Pro Met Lys Gly Met Leu Thr Gly
545                 550                 555                 560

Pro Val Thr Ile Leu Asn Trp Ser Phe Val Arg Asn Asp Gln Pro Arg
                565                 570                 575

Ser Glu Thr Thr Tyr Gln Ile Ala Leu Ala Ile Lys Asp Glu Val Glu
            580                 585                 590

Asp Leu Glu Lys Ala Gly Ile Thr Val Ile Gln Ile Asp Glu Ala Ala
        595                 600                 605

Leu Arg Glu Gly Leu Pro Leu Arg Lys Ser Glu Gln Ala His Tyr Leu
    610                 615                 620

Asp Trp Ala Val His Ala Phe Arg Ile Thr Asn Val Gly Val Gln Asp
625                 630                 635                 640

Thr Thr Gln Ile His Thr His Met Cys Tyr Ser Asn Phe Asn Asp Ile
                645                 650                 655

Ile His Ser Ile Ile Asp Met Asp Ala Asp Val Ile Thr Ile Glu Asn
            660                 665                 670

Ser Arg Ser Asp Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
    690                 695                 700

Ile Pro Pro Thr Glu Glu Ile Ala Asp Arg Ile Asn Lys Met Leu Ala
705                 710                 715                 720

Val Leu Glu Lys Asn Ile Leu Trp Val Asn Pro Asp Cys Gly Leu Lys
                725                 730                 735

Thr Arg Lys Tyr Thr Glu Val Lys Pro Pro Ser Gln Asn Met Val Ala
            740                 745                 750

Ala Ala Lys Leu Ile Arg Tyr Glu Leu Ala Lys
        755                 760

<210> SEQ ID NO 5
<211> LENGTH: 2296
<212> TYPE: DNA
<213> ORGANISM: Nicotiana plumbaginifolia

<400> SEQUENCE: 5
atggcatctc acattgttgg atatccccgt atgggcccaa agagagagct gaaatttgct      60
ctcgagtctt tctgggatgg gaagaggcgc tgaggacttg aagaaggtgg ctgcagacct     120
aaggtcttcc atctggaaac agatggctga tgctggcatc aagtacatcc ccagcaacac     180
attctcttac tatgatcagg tgcttgacac aactgcaatg ctcggtgctg tcccggctag     240
gtacaattgg gctggtggtg agatagcatt tgacacttac ttctccatgg ccagaggaaa     300
tgcctctgtc cctgctatgg agatgaccaa gtggtttgac accaactacc acttcattgt     360
ccctgagttg ggacctgatg ttaacttttc ttatgcttct cacaaggcag tagatgagta     420
```

-continued

```
caaagaggcc aaggggcttg gtgtagacac ggttccagtc cttattggtc cagtctcata      480
cttgttgcta tccaaacctg ctaagggtgt tgagaaatcc ttccctcttt tgtcacttct      540
tgacaaagtc cttccaatct acaaggaagt tattgcagaa ttgaaggctg ctggtgcttc      600
ttggattcag tttgatgaac ctacacttgt gttggatctc caagctcacc aattggaagc      660
cttcactaag gcctatgccg agttggaatc atctctgtct ggtcttaatg ttctcactga      720
aacctacttc gctgacgtcc ctgctgaagc attcaaaacc ctcactgctt tgaagggagt      780
tactgccttt ggttttgact tggttcgtgg agctcagacc cttgatttga tcaaaggtgg      840
cttcccttca ggcaagtact tgtttgctgg agtggtcgac ggaaggaaca tctgggcaaa      900
tgatcttgcc gcatctctta acctcctgca atctcttgag ggtattgttg aaaagacaa       960
actagttgtc tccacatctt gctcacttct tcatactgct gttgatcttg tcaatgagac     1020
taagctagat gatgaaatca agtcatggtt ggcgtttgct gcccaaaaag tagttgaagt     1080
taacgctttg gccaaggcat tggctggtca caaggatgag gcattcttct ctgcaaatgc     1140
taccgctcag gcttccagga atcctctccc aagagtgaca aatgaagctg tccaaaaggc     1200
tgctgctgca cttaagggtt ctgaccaccg ccgtgctaca aatgtcagtt ctagacttga     1260
tgcccaacaa agaaactta acctcccagt tctcccaaca accaccattg ggtccttccc     1320
tcagacagtg gagcttagga gagttcgccg tgaatacaag gccaagaaga tctctgagga     1380
agagtatgtt aaggccatca aggcagaaat caagaaggtc gttgatctcc aggaagagct     1440
cgacatcgat gtcttggttc acggagagcc agagaggaat gatatggttg aatacttcgg     1500
agagcagctt tctggttttg ccttcactgc taatggatgg gttcaatctt atggatctcg     1560
atgtgtgaag ccaccaatta tctatggtga tgtgagccgc cccaacccaa tgactgtatt     1620
ctggtccaaa acagctcaga gcatgaccaa gcgcccaatg aagggaatgc ttaccgggcc     1680
agttaccatt ctcaactggt cttttgtcag aaatgaccag ccaagatttg aaacttgcta     1740
ccagattgct ttggccatta aggatgaagt ggaagatttg gagaaggcag gcatcactgt     1800
tatccaaatt gatgaagctg ctttgagaga ggggttgcct ctaaggaagg ctgagcacgc     1860
tttttacttg aactgggctg tccactcctt cagaatcacc aacgtcggca ttcaagacac     1920
cacccagatc cacacacaca tgtgctactc caacttcaat gacattatcc actctatcat     1980
tgacatggat gctgatgtga tcacaattga gaactcacgg tccgatgaga agctcctctc     2040
agttttcagg gagggagtta agtatggtgc tggaattggc cctggtgtct atgacatcca     2100
ctcccctaga ataccatcaa cggaagagat tgctgacaga gttaacaaga tgcttgctgt     2160
tcttgacacc aacatcttgt gggtcaaccc agattgtggt ctcaagactc gcaagtacgc     2220
tgaggtaaag ccagccctcg agaacatggt ttctgctgcc aaggccatcc gcacccaact     2280
tgccagctcc aagtga                                                    2296
```

<210> SEQ ID NO 6
<211> LENGTH: 765
<212> TYPE: PRT
<213> ORGANISM: Nicotiana plumbaginifolia

<400> SEQUENCE: 6

```
Met Ala Ser His Ile Val Gly Tyr Pro Arg Met Gly Pro Lys Arg Glu
 1               5                  10                  15

Leu Lys Phe Ala Leu Glu Ser Phe Trp Asp Gly Lys Ser Ser Ala Glu
            20                  25                  30

Asp Leu Lys Lys Val Ala Ala Asp Leu Arg Ser Ser Ile Trp Lys Gln
```

```
              35                  40                  45
Met Ala Asp Ala Gly Ile Lys Tyr Ile Pro Ser Asn Thr Phe Ser Tyr
          50                  55                  60

Tyr Asp Gln Val Leu Asp Thr Thr Ala Met Leu Gly Ala Val Pro Ala
 65                  70                  75                  80

Arg Tyr Asn Trp Ala Gly Gly Glu Ile Ala Phe Asp Thr Tyr Phe Ser
                 85                  90                  95

Met Ala Arg Gly Asn Ala Ser Val Pro Ala Met Glu Met Thr Lys Trp
            100                 105                 110

Phe Asp Thr Asn Tyr His Phe Ile Val Pro Glu Leu Gly Pro Asp Val
            115                 120                 125

Asn Phe Ser Tyr Ala Ser His Lys Ala Val Asp Glu Tyr Lys Glu Ala
        130                 135                 140

Lys Gly Leu Gly Val Asp Thr Val Pro Val Leu Ile Gly Pro Val Ser
145                 150                 155                 160

Tyr Leu Leu Leu Ser Lys Pro Ala Lys Gly Val Glu Lys Ser Phe Pro
                165                 170                 175

Leu Leu Ser Leu Leu Asp Lys Val Leu Pro Ile Tyr Lys Glu Val Ile
            180                 185                 190

Ala Glu Leu Lys Ala Ala Gly Ala Ser Trp Ile Gln Phe Asp Glu Pro
        195                 200                 205

Thr Leu Val Leu Asp Leu Gln Ala His Gln Leu Glu Ala Phe Thr Lys
210                 215                 220

Ala Tyr Ala Glu Leu Glu Ser Ser Leu Ser Gly Leu Asn Val Leu Thr
225                 230                 235                 240

Glu Thr Tyr Phe Ala Asp Val Pro Ala Glu Ala Phe Lys Thr Leu Thr
                245                 250                 255

Ala Leu Lys Gly Val Thr Ala Phe Gly Phe Asp Leu Val Arg Gly Ala
            260                 265                 270

Gln Thr Leu Asp Leu Ile Lys Gly Gly Phe Pro Ser Gly Lys Tyr Leu
        275                 280                 285

Phe Ala Gly Val Val Asp Gly Arg Asn Ile Trp Ala Asn Asp Leu Ala
290                 295                 300

Ala Ser Leu Asn Leu Leu Gln Ser Leu Glu Gly Ile Val Gly Lys Asp
305                 310                 315                 320

Lys Leu Val Val Ser Thr Ser Cys Ser Leu Leu His Thr Ala Val Asp
                325                 330                 335

Leu Val Asn Glu Thr Lys Leu Asp Asp Glu Ile Lys Ser Trp Leu Ala
            340                 345                 350

Phe Ala Ala Gln Lys Val Val Glu Val Asn Ala Leu Ala Lys Ala Leu
        355                 360                 365

Ala Gly His Lys Asp Glu Ala Phe Phe Ser Ala Asn Ala Thr Ala Gln
370                 375                 380

Ala Ser Arg Lys Ser Ser Pro Arg Val Thr Asn Glu Ala Val Gln Lys
385                 390                 395                 400

Ala Ala Ala Ala Leu Lys Gly Ser Asp His Arg Arg Ala Thr Asn Val
                405                 410                 415

Ser Ser Arg Leu Asp Ala Gln Gln Lys Lys Leu Asn Leu Pro Val Leu
            420                 425                 430

Pro Thr Thr Thr Ile Gly Ser Phe Pro Gln Thr Val Glu Leu Arg Arg
        435                 440                 445

Val Arg Arg Glu Tyr Lys Ala Lys Lys Ile Ser Glu Glu Glu Tyr Val
450                 455                 460
```

-continued

```
Lys Ala Ile Lys Ala Glu Ile Lys Lys Val Val Asp Leu Gln Glu Glu
465                 470                 475                 480

Leu Asp Ile Asp Val Leu Val His Gly Glu Pro Glu Arg Asn Asp Met
            485                 490                 495

Val Glu Tyr Phe Gly Glu Gln Leu Ser Gly Phe Ala Phe Thr Ala Asn
        500                 505                 510

Gly Trp Val Gln Ser Tyr Gly Ser Arg Cys Val Lys Pro Pro Ile Ile
    515                 520                 525

Tyr Gly Asp Val Ser Arg Pro Asn Pro Met Thr Val Phe Trp Ser Lys
530                 535                 540

Thr Ala Gln Ser Met Thr Lys Arg Pro Met Lys Gly Met Leu Thr Gly
545                 550                 555                 560

Pro Val Thr Ile Leu Asn Trp Ser Phe Val Arg Asn Asp Gln Pro Arg
                565                 570                 575

Phe Glu Thr Cys Tyr Gln Ile Ala Leu Ala Ile Lys Asp Glu Val Glu
            580                 585                 590

Asp Leu Glu Lys Ala Gly Ile Thr Val Ile Gln Ile Asp Glu Ala Ala
        595                 600                 605

Leu Arg Glu Gly Leu Pro Leu Arg Lys Ala Glu His Ala Phe Tyr Leu
    610                 615                 620

Asn Trp Ala Val His Ser Phe Arg Ile Thr Asn Val Gly Ile Gln Asp
625                 630                 635                 640

Thr Thr Gln Ile His Thr His Met Cys Tyr Ser Asn Phe Asn Asp Ile
                645                 650                 655

Ile His Ser Ile Ile Asp Met Asp Ala Asp Val Ile Thr Ile Glu Asn
            660                 665                 670

Ser Arg Ser Asp Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
    690                 695                 700

Ile Pro Ser Thr Glu Glu Ile Ala Asp Arg Val Asn Lys Met Leu Ala
705                 710                 715                 720

Val Leu Asp Thr Asn Ile Leu Trp Val Asn Pro Asp Cys Gly Leu Lys
                725                 730                 735

Thr Arg Lys Tyr Ala Glu Val Lys Pro Ala Leu Glu Asn Met Val Ser
            740                 745                 750

Ala Ala Lys Ala Ile Arg Thr Gln Leu Ala Ser Ser Lys
        755                 760                 765

<210> SEQ ID NO 7
<211> LENGTH: 475
<212> TYPE: DNA
<213> ORGANISM: Triticum aestivum
<220> FEATURE:
<221> NAME/KEY: unsure
<222> LOCATION: (344)
<223> OTHER INFORMATION: n = A, C, G, or T
<220> FEATURE:
<221> NAME/KEY: unsure
<222> LOCATION: (367)
<223> OTHER INFORMATION: n = A, C, G, or T
<220> FEATURE:
<221> NAME/KEY: unsure
<222> LOCATION: (433)
<223> OTHER INFORMATION: n = A, C, G, or T
<220> FEATURE:
<221> NAME/KEY: unsure
<222> LOCATION: (452)
<223> OTHER INFORMATION: n = A, C, G, or T
```

```
<220> FEATURE:
<221> NAME/KEY: unsure
<222> LOCATION: (473)..(474)
<223> OTHER INFORMATION: n = A, C, G, or T

<400> SEQUENCE: 7
cgccatcctc ctcctctccc cctatcgtct tcctccccat ctccggcgcc gctccgcgac      60
tcctccaagg aaagatggca tcccacattg ttggataccc tcgcatgggc cccaagaggg     120
agctcaagtt tgccttggag tctttctggg atgggaagag cagcgctgag gatttggaga     180
aggttgccgc cgacctcagg gccagcatct ggaagcagat gtcagaggct gggattaagt     240
acattcccag caacaccttc tcatactatg accaggtgct tgacacaacg gccatgcttg     300
gtgccgtccc ggaccgctac tcatggactg gcggagagat tggncacagc acctacttct     360
caatggncaa gggcaatgcc actgtccctg ctatggagat gaccaagtgg tttgacacca     420
actaacactt cantgtgcct gaattgagcc ancaaccaag ttctcatatg ctnna          475

<210> SEQ ID NO 8
<211> LENGTH: 124
<212> TYPE: PRT
<213> ORGANISM: Triticum aestivum
<220> FEATURE:
<221> NAME/KEY: UNSURE
<222> LOCATION: (98)
<223> OTHER INFORMATION: Xaa = any amino acid
<220> FEATURE:
<221> NAME/KEY: UNSURE
<222> LOCATION: (117)
<223> OTHER INFORMATION: Xaa = any amino acid
<220> FEATURE:
<221> NAME/KEY: UNSURE
<222> LOCATION: (120)
<223> OTHER INFORMATION: Xaa = any amino acid

<400> SEQUENCE: 8

Met Ala Ser His Ile Val Gly Tyr Pro Arg Met Gly Pro Lys Arg Glu
  1               5                  10                  15

Leu Lys Phe Ala Leu Glu Ser Phe Trp Asp Gly Lys Ser Ser Ala Glu
             20                  25                  30

Asp Leu Glu Lys Val Ala Ala Asp Leu Arg Ala Ser Ile Trp Lys Gln
         35                  40                  45

Met Ser Glu Ala Gly Ile Lys Tyr Ile Pro Ser Asn Thr Phe Ser Tyr
     50                  55                  60

Tyr Asp Gln Val Leu Asp Thr Thr Ala Met Leu Gly Ala Val Pro Asp
 65                  70                  75                  80

Arg Tyr Ser Trp Thr Gly Gly Glu Ile Gly His Ser Thr Tyr Phe Ser
                 85                  90                  95

Met Xaa Lys Gly Asn Ala Thr Val Pro Ala Met Glu Met Thr Lys Trp
            100                 105                 110

Phe Asp Thr Asn Xaa His Phe Xaa Val Pro Glu Leu
        115                 120

<210> SEQ ID NO 9
<211> LENGTH: 628
<212> TYPE: DNA
<213> ORGANISM: Triticum aestivum
<220> FEATURE:
<221> NAME/KEY: unsure
<222> LOCATION: (219)
<223> OTHER INFORMATION: n = A, C, G, or T
<220> FEATURE:
<221> NAME/KEY: unsure
<222> LOCATION: (254)
```

-continued

```
<223> OTHER INFORMATION: n = A, C, G, or T
<220> FEATURE:
<221> NAME/KEY: unsure
<222> LOCATION: (300)
<223> OTHER INFORMATION: n = A, C, G, or T
<220> FEATURE:
<221> NAME/KEY: unsure
<222> LOCATION: (319)
<223> OTHER INFORMATION: n = A, C, G, or T
<220> FEATURE:
<221> NAME/KEY: unsure
<222> LOCATION: (331)
<223> OTHER INFORMATION: n = A, C, G, or T
<220> FEATURE:
<221> NAME/KEY: unsure
<222> LOCATION: (335)
<223> OTHER INFORMATION: n = A, C, G, or T
<220> FEATURE:
<221> NAME/KEY: unsure
<222> LOCATION: (338)
<223> OTHER INFORMATION: n = A, C, G, or T
<220> FEATURE:
<221> NAME/KEY: unsure
<222> LOCATION: (348)
<223> OTHER INFORMATION: n = A, C, G, or T
<220> FEATURE:
<221> NAME/KEY: unsure
<222> LOCATION: (350)
<223> OTHER INFORMATION: n = A, C, G, or T
<220> FEATURE:
<221> NAME/KEY: unsure
<222> LOCATION: (360)
<223> OTHER INFORMATION: n = A, C, G, or T
<220> FEATURE:
<221> NAME/KEY: unsure
<222> LOCATION: (413)
<223> OTHER INFORMATION: n = A, C, G, or T
<220> FEATURE:
<221> NAME/KEY: unsure
<222> LOCATION: (416)
<223> OTHER INFORMATION: n = A, C, G, or T
<220> FEATURE:
<221> NAME/KEY: unsure
<222> LOCATION: (424)
<223> OTHER INFORMATION: n = A, C, G, or T
<220> FEATURE:
<221> NAME/KEY: unsure
<222> LOCATION: (428)
<223> OTHER INFORMATION: n = A, C, G, or T
<220> FEATURE:
<221> NAME/KEY: unsure
<222> LOCATION: (440)
<223> OTHER INFORMATION: n = A, C, G, or T
<220> FEATURE:
<221> NAME/KEY: unsure
<222> LOCATION: (455)
<223> OTHER INFORMATION: n = A, C, G, or T
<220> FEATURE:
<221> NAME/KEY: unsure
<222> LOCATION: (469)
<223> OTHER INFORMATION: n = A, C, G, or T
<220> FEATURE:
<221> NAME/KEY: unsure
<222> LOCATION: (473)
<223> OTHER INFORMATION: n = A, C, G, or T
<220> FEATURE:
<221> NAME/KEY: unsure
<222> LOCATION: (484)
<223> OTHER INFORMATION: n = A, C, G, or T
<220> FEATURE:
<221> NAME/KEY: unsure
<222> LOCATION: (504)
<223> OTHER INFORMATION: n = A, C, G, or T
<220> FEATURE:
<221> NAME/KEY: unsure
<222> LOCATION: (506)
<223> OTHER INFORMATION: n = A, C, G, or T
<220> FEATURE:
<221> NAME/KEY: unsure
```

```
<222> LOCATION: (526)
<223> OTHER INFORMATION: n = A, C, G, or T
<220> FEATURE:
<221> NAME/KEY: unsure
<222> LOCATION: (533)
<223> OTHER INFORMATION: n = A, C, G, or T
<220> FEATURE:
<221> NAME/KEY: unsure
<222> LOCATION: (535)
<223> OTHER INFORMATION: n = A, C, G, or T
<220> FEATURE:
<221> NAME/KEY: unsure
<222> LOCATION: (552)
<223> OTHER INFORMATION: n = A, C, G, or T
<220> FEATURE:
<221> NAME/KEY: unsure
<222> LOCATION: (568)
<223> OTHER INFORMATION: n = A, C, G, or T
<220> FEATURE:
<221> NAME/KEY: unsure
<222> LOCATION: (580)
<223> OTHER INFORMATION: n = A, C, G, or T
<220> FEATURE:
<221> NAME/KEY: unsure
<222> LOCATION: (598)
<223> OTHER INFORMATION: n = A, C, G, or T
<220> FEATURE:
<221> NAME/KEY: unsure
<222> LOCATION: (600)
<223> OTHER INFORMATION: n = A, C, G, or T
<220> FEATURE:
<221> NAME/KEY: unsure
<222> LOCATION: (606)
<223> OTHER INFORMATION: n = A, C, G, or T
<220> FEATURE:
<221> NAME/KEY: unsure
<222> LOCATION: (613)
<223> OTHER INFORMATION: n = A, C, G, or T

<400> SEQUENCE: 9
ggtcgtcacc cagagtgaac aattaggagg ttcagaaggc tgcggctgct ttgaagggct      60
ctgaccaccg ccgtgctacc cctgtctctg ctagactgga cgctcagcag aagaagctca     120
accttcctat cctcccaaca acaacaattg gttcattccc tcagacaatg gacctcagga     180
gggtccgccg tgagtacaag gcgaaagaag atctctgang aggagtatgt cagtgctatc     240
aaggaagaaa ttancaaagg ttgtcaagat tcaaagagga gcttgacatt gatgttctcn     300
tccaatggaa aagcctgana aaaatgacat nggtnaanta cttcggcnan caaattatcn     360
gggtttgcaa ttactgccaa tggatgggtg caatcctatg gattacttgc gtnaancacc     420
gatnatcnat gggatgtaan cgcccaaccc atganatctt ctggtcaana tgntcaggac     480
atancctccc ccaatgaagg aatntnacgg cctttaaatc ccaacnggct ttntnagaac     540
acaaccaggt tnagaatgca caaattcnct gccataaaan gagttaggtt ccagctgngn     600
atcagngtca atnataggg ccaaaagg                                         628

<210> SEQ ID NO 10
<211> LENGTH: 118
<212> TYPE: PRT
<213> ORGANISM: Triticum aestivum
<220> FEATURE:
<221> NAME/KEY: UNSURE
<222> LOCATION: (8)
<223> OTHER INFORMATION: Xaa = any amino acid
<220> FEATURE:
<221> NAME/KEY: UNSURE
<222> LOCATION: (72)..(73)
<223> OTHER INFORMATION: Xaa = any amino acid
<220> FEATURE:
<221> NAME/KEY: UNSURE
<222> LOCATION: (84)
```

```
<223> OTHER INFORMATION: Xaa = any amino acid
<220> FEATURE:
<221> NAME/KEY: UNSURE
<222> LOCATION: (100)
<223> OTHER INFORMATION: Xaa = any amino acid
<220> FEATURE:
<221> NAME/KEY: UNSURE
<222> LOCATION: (106)
<223> OTHER INFORMATION: Xaa = any amino acid
<220> FEATURE:
<221> NAME/KEY: UNSURE
<222> LOCATION: (110)
<223> OTHER INFORMATION: Xaa = any amino acid
<220> FEATURE:
<221> NAME/KEY: UNSURE
<222> LOCATION: (112)
<223> OTHER INFORMATION: Xaa = any amino acid
<220> FEATURE:
<221> NAME/KEY: UNSURE
<222> LOCATION: (116)
<223> OTHER INFORMATION: Xaa = any amino acid

<400> SEQUENCE: 10

Ser Ser Pro Arg Val Asn Asn Xaa Glu Val Gln Lys Ala Ala Ala Ala
 1               5                  10                  15

Leu Lys Gly Ser Asp His Arg Arg Ala Thr Pro Val Ser Ala Arg Leu
            20                  25                  30

Asp Ala Gln Gln Lys Lys Leu Asn Leu Pro Ile Leu Pro Thr Thr Thr
        35                  40                  45

Ile Gly Ser Phe Pro Gln Thr Met Asp Leu Arg Arg Val Arg Arg Glu
 50                  55                  60

Tyr Lys Ala Lys Glu Asp Leu Xaa Xaa Gly Val Cys Gln Cys Tyr Gln
 65                  70                  75                  80

Gly Arg Asn Xaa Gln Arg Leu Ser Arg Phe Lys Glu Glu Leu Asp Ile
            85                  90                  95

Asp Val Leu Xaa Gln Trp Arg Ser Leu Xaa Lys Met Thr Xaa Val Xaa
        100                 105                 110

Tyr Phe Gly Xaa Gln Ile
        115

<210> SEQ ID NO 11
<211> LENGTH: 765
<212> TYPE: PRT
<213> ORGANISM: Catharanthus roseus

<400> SEQUENCE: 11

Met Ala Ser His Ile Val Gly Tyr Pro Arg Met Gly Pro Lys Arg Glu
 1               5                  10                  15

Leu Lys Phe Ala Leu Glu Ser Phe Trp Asp Lys Lys Ser Ser Ala Glu
            20                  25                  30

Asp Leu Gln Lys Val Ala Ala Asp Leu Arg Ser Ser Ile Trp Lys Gln
        35                  40                  45

Met Ala Asp Ala Gly Ile Lys Tyr Ile Pro Ser Asn Thr Phe Ser Tyr
 50                  55                  60

Tyr Asp Gln Val Leu Asp Thr Ala Thr Met Leu Gly Ala Val Pro Pro
 65                  70                  75                  80

Arg Tyr Asn Phe Ala Gly Gly Glu Ile Gly Phe Asp Thr Tyr Phe Ser
            85                  90                  95

Met Ala Arg Gly Asn Ala Ser Val Pro Ala Met Glu Met Thr Lys Trp
        100                 105                 110

Phe Asp Thr Asn Tyr His Tyr Ile Val Pro Glu Leu Gly Pro Glu Val
        115                 120                 125
```

-continued

Asn Phe Ser Tyr Ala Ser His Lys Ala Val Asn Glu Tyr Lys Glu Ala
    130                 135                 140

Lys Glu Leu Gly Val Asp Thr Val Pro Val Leu Val Gly Pro Val Thr
145                 150                 155                 160

Phe Leu Leu Leu Ser Lys Pro Ala Lys Gly Val Glu Lys Thr Phe Pro
                165                 170                 175

Leu Leu Ser Leu Leu Asp Lys Ile Leu Pro Val Tyr Lys Glu Val Ile
            180                 185                 190

Gly Glu Leu Lys Ala Ala Gly Ala Ser Trp Ile Gln Phe Asp Glu Pro
        195                 200                 205

Thr Leu Val Leu Asp Leu Glu Ser His Gln Leu Glu Ala Phe Thr Lys
    210                 215                 220

Ala Tyr Ser Glu Leu Glu Ser Thr Leu Ser Gly Leu Asn Val Ile Val
225                 230                 235                 240

Glu Thr Tyr Phe Ala Asp Ile Pro Ala Glu Thr Tyr Lys Ile Leu Thr
                245                 250                 255

Ala Leu Lys Gly Val Thr Gly Phe Gly Phe Asp Leu Val Arg Gly Ala
            260                 265                 270

Lys Thr Leu Asp Leu Ile Lys Gly Gly Phe Pro Ser Gly Lys Tyr Leu
        275                 280                 285

Phe Ala Gly Val Val Asp Gly Arg Asn Ile Trp Ala Asn Asp Leu Ala
    290                 295                 300

Ala Ser Leu Ser Thr Leu Gln Ser Leu Glu Gly Ile Val Gly Lys Asp
305                 310                 315                 320

Lys Leu Val Val Ser Thr Ser Cys Ser Leu Leu His Thr Ala Val Asp
                325                 330                 335

Leu Val Asn Glu Pro Lys Leu Asp Lys Glu Ile Lys Ser Trp Leu Ala
            340                 345                 350

Phe Ala Ala Gln Lys Val Val Glu Val Asn Ala Leu Ala Lys Ala Leu
        355                 360                 365

Ala Gly Glu Lys Asp Glu Ala Phe Phe Ser Glu Asn Ala Ala Ala Gln
    370                 375                 380

Ala Ser Arg Lys Ser Ser Pro Arg Val Thr Asn Gln Ala Val Gln Lys
385                 390                 395                 400

Ala Ala Ala Ala Leu Arg Gly Ser Asp His Arg Arg Ala Thr Thr Val
                405                 410                 415

Ser Ala Arg Leu Asp Ala Gln Gln Lys Lys Leu Asn Leu Pro Val Leu
            420                 425                 430

Pro Thr Thr Thr Ile Gly Ser Phe Pro Gln Thr Leu Glu Leu Arg Arg
        435                 440                 445

Val Arg Arg Glu Tyr Lys Ala Lys Lys Ile Ser Glu Asp Asp Tyr Val
    450                 455                 460

Lys Ala Ile Lys Glu Glu Ile Ser Lys Val Val Lys Leu Gln Glu Glu
465                 470                 475                 480

Leu Asp Ile Asp Val Leu Val His Gly Glu Pro Glu Arg Asn Asp Met
                485                 490                 495

Val Glu Tyr Phe Gly Glu Gln Leu Ser Gly Phe Ala Phe Thr Ala Asn
            500                 505                 510

Gly Trp Val Gln Ser Tyr Gly Ser Arg Cys Val Lys Pro Pro Ile Ile
        515                 520                 525

Tyr Gly Asp Val Ser Arg Pro Asn Pro Met Thr Val Phe Trp Ser Gln
    530                 535                 540

```
Thr Ala Gln Ser Met Thr Lys Arg Pro Met Lys Gly Met Leu Thr Gly
545                 550                 555                 560

Pro Val Thr Ile Leu Asn Trp Ser Phe Val Arg Asn Asp Gln Pro Arg
                565                 570                 575

Phe Glu Thr Cys Tyr Gln Ile Ala Leu Ala Ile Lys Asp Glu Val Glu
            580                 585                 590

Asp Leu Glu Lys Ala Gly Ile Asn Val Ile Gln Ile Asp Glu Ala Ala
        595                 600                 605

Leu Arg Glu Gly Leu Pro Leu Arg Lys Ala Glu His Ala Phe Tyr Leu
610                 615                 620

Asp Trp Ala Val His Ser Phe Arg Ile Thr Asn Leu Pro Leu Gln Asp
625                 630                 635                 640

Thr Thr Gln Ile His Thr His Met Cys Tyr Ser Asn Phe Asn Asp Ile
                645                 650                 655

Ile His Ser Ile Ile Asp Met Asp Ala Asp Val Met Thr Ile Glu Asn
            660                 665                 670

Ser Arg Ser Ser Glu Lys Leu Leu Ser Val Phe Arg Glu Gly Val Lys
        675                 680                 685

Tyr Gly Ala Gly Ile Gly Pro Gly Val Tyr Asp Ile His Ser Pro Arg
690                 695                 700

Ile Pro Ser Thr Glu Glu Ile Ala Asp Arg Ile Asn Lys Met Leu Ala
705                 710                 715                 720

Val Leu Asp Thr Asn Ile Leu Trp Val Asn Pro Asp Cys Gly Leu Lys
                725                 730                 735

Thr Arg Lys Tyr Ala Glu Val Lys Pro Ala Leu Glu Asn Met Val Ser
            740                 745                 750

Ala Ala Lys Leu Ile Arg Thr Gln Leu Ala Ser Ala Lys
        755                 760                 765

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 12
atccaacaat gtgagatgtc atgaattctg ac                                  32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 13
gtcagaattc atgacatctc acattgttgg at                                  32

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 14
```

```
ctcacggtcc gatgagaagc tcct                                          24
```

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 15

```
gatcggtacc tcacttggag ctggcaagtt g                                  31
```

<210> SEQ ID NO 16
<211> LENGTH: 1638
<212> TYPE: DNA
<213> ORGANISM: Zea mays

<400> SEQUENCE: 16

```
gaattccggc tcgaagccgc cgcgaccgaa cgagcgaagc gtcccttccc gcgccgacgc    60
cgaaaccctg gctcctctta cgccatggcc accgtgtcgc tcactccgca ggcggtcttc   120
tccaccgagt ccggcggcgc cctggcctct gccaccatcc tccgcttccc gccaaacttc   180
gtccgcctcc gcggcggcgg atgtcagcgc aattcctaac gctaaggttg cgcagccgtc   240
cgccgtcgta ttggccgagc gtaacctgct cggctccgac gccagcctcg ccgtccacgc   300
gggggagagg ctgggaagaa ggatagccac ggatgctatc accacgccgg tagtgaacac   360
gtcggcctac tggttcaaca actcgcaaga gctaatcgac tttaaggagg ggaggcatgc   420
tagcttcgag tatgggaggt atgggaaccc gaccacggag gcattagaga agaagatgag   480
cgcactggag aaagcagagt ccaccgtgtt tgtggcgtca gggatgtatg cagctgtggc   540
tatgctcagc gcacttgtcc ctgctggtgg gcacattgtg accaccacgg attgctaccg   600
caagacaagg atttacatgg aaaatgagct ccctaagagg ggaatttcga tgactgtcat   660
taggcctgct gacatggatg ctctccaaaa tgccttggac aacaataatg tatctctttt   720
cttcacggag actcctacaa atccatttct cagatgcatt gatattgaac atgtatcaaa   780
tatgtgccat agcaagggag cgttgctttg tattgacagt actttcgcgt cacctatcaa   840
tcagaaggca ttaactttag gtgctgacct agttattcat tctgcaacga agtacattgc   900
tggacacaat gatgttattg gaggatgcgt cagtggcaga gatgagttag tttccaaagt   960
tcgtatttac caccatgtag ttggtggtgt tctaaacccg aatgctgcgt accttatcct  1020
tcgaggtatg aagacactgc atctccgtgt gcaatgtcag aacgacactg ctcttcggat  1080
ggcccagttt ttagaggagc atccaaagat tgctcgtgtc tactatcctg gcttgccaag  1140
tcaccctgaa catcacattg ccaagagtca atgactggc tttggcggtg ttgttagttt   1200
tgaggttgct ggagactttg atgctacgag gaaattcatt gattctgtta aaatacccta  1260
tcatgcgcct tcttttggag gctgtgagag cataattgat cagcctgcca tcatgtccta  1320
ctgggattca aaggagcagc gggacatcta cgggatcaag gacaacctga tcaggttcag  1380
cattggtgtg gaggatttcg aggatcttaa gaacgatctc gtgcaggccc tcgagaagat  1440
ctaagcactc taatcagttt gtattgacaa aatatgaggt gatggctgtc ttggatcttg  1500
tcaagatctg tgacaatgat atgagctgat gactgcgaat aagttctctt ttgcttattt  1560
tatccgtcaa attcaaaaaa aaaaaaaaaa aaaaaaaaaa aaaaaaaaaa aaaaaaaaa   1620
aaaaaaaaaa aactcgag                                                1638
```

<210> SEQ ID NO 17
<211> LENGTH: 480
<212> TYPE: PRT
<213> ORGANISM: Zea mays

<400> SEQUENCE: 17

```
Asn Ser Gly Ser Lys Pro Pro Arg Pro Asn Glu Arg Ser Val Pro Ser
  1               5                  10                  15

Arg Ala Asp Ala Glu Thr Leu Ala Pro Leu Thr Pro Trp Pro Pro Cys
             20                  25                  30

Arg Ser Leu Arg Arg Ser Ser Pro Ser Pro Ala Ala Pro Trp
         35                  40                  45

Pro Leu Pro Pro Ser Ser Ala Ser Arg Gln Thr Ser Ser Ala Ser Ala
     50                  55                  60

Ala Ala Asp Val Ser Ala Ile Pro Asn Ala Lys Val Ala Gln Pro Ser
 65                  70                  75                  80

Ala Val Val Leu Ala Glu Arg Asn Leu Gly Ser Asp Ala Ser Leu
                 85                  90                  95

Ala Val His Ala Gly Glu Arg Leu Gly Arg Arg Ile Ala Thr Asp Ala
            100                 105                 110

Ile Thr Thr Pro Val Val Asn Thr Ser Ala Tyr Trp Phe Asn Asn Ser
            115                 120                 125

Gln Glu Leu Ile Asp Phe Lys Glu Gly Arg His Ala Ser Phe Glu Tyr
        130                 135                 140

Gly Arg Tyr Gly Asn Pro Thr Thr Glu Ala Leu Glu Lys Lys Met Ser
145                 150                 155                 160

Ala Leu Glu Lys Ala Glu Ser Thr Val Phe Val Ala Ser Gly Met Tyr
                165                 170                 175

Ala Ala Val Ala Met Leu Ser Ala Leu Val Pro Ala Gly Gly His Ile
            180                 185                 190

Val Thr Thr Thr Asp Cys Tyr Arg Lys Thr Arg Ile Tyr Met Glu Asn
            195                 200                 205

Glu Leu Pro Lys Arg Gly Ile Ser Met Thr Val Ile Arg Pro Ala Asp
        210                 215                 220

Met Asp Ala Leu Gln Asn Ala Leu Asp Asn Asn Val Ser Leu Phe
225                 230                 235                 240

Phe Thr Glu Thr Pro Thr Asn Pro Phe Leu Arg Cys Ile Asp Ile Glu
                245                 250                 255

His Val Ser Asn Met Cys His Ser Lys Gly Ala Leu Leu Cys Ile Asp
            260                 265                 270

Ser Thr Phe Ala Ser Pro Ile Asn Gln Lys Ala Leu Thr Leu Gly Ala
        275                 280                 285

Asp Leu Val Ile His Ser Ala Thr Lys Tyr Ile Ala Gly His Asn Asp
    290                 295                 300

Val Ile Gly Gly Cys Val Ser Gly Arg Asp Glu Leu Val Ser Lys Val
305                 310                 315                 320

Arg Ile Tyr His His Val Val Gly Gly Val Leu Asn Pro Asn Ala Ala
                325                 330                 335

Tyr Leu Ile Leu Arg Gly Met Lys Thr Leu His Leu Arg Val Gln Cys
            340                 345                 350

Gln Asn Asp Thr Ala Leu Arg Met Ala Gln Phe Leu Glu Glu His Pro
        355                 360                 365

Lys Ile Ala Arg Val Tyr Tyr Pro Gly Leu Pro Ser His Pro Glu His
    370                 375                 380
```

```
His Ile Ala Lys Ser Gln Met Thr Gly Phe Gly Val Val Ser Phe
385                 390                 395                 400

Glu Val Ala Gly Asp Phe Asp Ala Thr Arg Lys Phe Ile Asp Ser Val
                405                 410                 415

Lys Ile Pro Tyr His Ala Pro Ser Phe Gly Gly Cys Glu Ser Ile Ile
            420                 425                 430

Asp Gln Pro Ala Ile Met Ser Tyr Trp Asp Ser Lys Glu Gln Arg Asp
        435                 440                 445

Ile Tyr Gly Ile Lys Asp Asn Leu Ile Arg Phe Ser Ile Gly Val Glu
    450                 455                 460

Asp Phe Glu Asp Leu Lys Asn Asp Leu Val Gln Ala Leu Glu Lys Ile
465                 470                 475                 480

<210> SEQ ID NO 18
<211> LENGTH: 3639
<212> TYPE: DNA
<213> ORGANISM: Zea mays

<400> SEQUENCE: 18
tctagattac ataatacacc taataatctt gtgttgtttg tttacttctc aacttattta      60
agttggatta tattccatct tttctttttt atttgtctgt tttagttaaa aatgaactaa     120
caaacgacaa atattcgaga acgagatagt ataatctata ggataatcag acatgtcctt     180
agagggtgtt tgtttagaat tataatatgt atagaatata taatccaaca aattttgaac     240
taacaagttt aaaatttgat agattatata atctgggcac attataatcc taaacaaaca     300
ccatcttagt aatttttat ttagtgctcc gtttggatgt gaagaagatg gagttgaata     360
ccaaatcatg tatgatactg aaatgagatg taattttaat tctattgttt ggatgtcgtt     420
gaattggagt ttgaagttat gcggtctaat tttacgcaat accgagatga gactttatac     480
taggagaggg gtttctagtt atagcctaat tctaaagaat tgagtctcta tttccaaatc     540
ttaattttat gcaactaaac aacacaattt agaaaaactg ttttcaattt cttattctgt     600
gctccaaacg aggtggagta tttagaagta gataagcgcc tctgctgcac gaagcgatga     660
acgcactctg acggtcttgc cactacaaat aagccgcacc gcatttcgga aggccacgcg     720
accgccacct ccccgaagct gccgcgaccg atcgagcgaa gcgtcgctcc ccgcgccgcc     780
gccaaaaccc tagcttctcc tactccatgg ccactgtctc gctcaccccg caggctgtct     840
tctccacgga gtccggtggc gccctggcct ctgctaccat cctccgcttt ccgccaaact     900
ttgtccgcca gcttagcacc aaggcacgcc gcaactgcag caacatcggc gtcgcgcaga     960
tcgtcgccgc cgcgtggtcc gactgccccg ccgctcgccc ccacttaggc ggcggcggcc    1020
gccgcgcccg cggcgtggcc tcctcccacg ccgcggctgc atcggccgcc gccgccgcct    1080
ccgcggcggc ggaggtcagc gcaattccca acgctaaggt tgcgcaaccg tccgccgtcg    1140
tcttggccga gcgtaacctg ctcggctccg acgccagcct cgccgtccac gcgggtaccc    1200 tacccctgcta gctcgtctct ttactgtaag atctaggttc tatgcttttt tccccttttcg    1260 atgattcctt tgtggctttg ctgccttttt atctgaaaca ggggagaggc tgggaagaag    1320
gatcgccacg gatgcgatca ccacaccggt agtgaacacg tcggcctact ggttcaacaa    1380
ctcgcaagag ctaatcgact ttaaggtagt gaatattcgt gcttgctctt gtctaatttg    1440
acggatgtga gttttgacgc cgaaatatta agtttatct gttccttagg aggggaggca    1500
tgctagcttc gagtatggga ggtatgggaa cccgaccacg gaggcattag agaagaagat    1560
```

-continued

```
gaggtgatgc tcgatagtgg aaatgtcggc accctgttgg ttgcatttgg ctggaggcta      1620
aacagttgcg tgttctcatg gtgcagcgca ctggagaaag cagagtccac agtgttcgtg      1680
gcatcgggga tgtatgcagc tgcggctatg ctcagtgcac ttgttccggc tggtgggcac      1740
attgtgacca ccacggattg ctaccggaaa acaaggattt acatggaaac tgagctcccc      1800
aagaggggaa tttcggtaat accatgcgat cttttaagct ctacttgttt ttagaacggg      1860
acatctgcta tcactattgg ttgtcttcct gtcactgtgc tacagtagtg ggtctacaat      1920
gaacttgctc ttattcagtt aaaattactc tgtcgtgttg tccttatcta gctaatagtc      1980
tctacaaagt tcagttactt cagcatagcc aataggagta gcataactac tgcagggtat      2040
atgaacaata tccttttgcag tagctgttgg gagtacacag tacagtatgg cttcagactt      2100
tattctttgt actgcattgg gtgaagccac atagggtttg ccgagtgcac gtgcaccagg      2160
gaaaaaacaa tttctacttt tctagtgatt aaaaactaaa ttttaccact catgcacacc      2220
ctaattttta attagagaag attttcaata catgtgtata ttgaaatgtc aagtgtgcac      2280
tcggattctc cggcctctag cttcgcccga ctgcaatgtc aataggattg gctatctgta      2340
aaggatttaa gtagaactgc ttgtggtaat aaattttagg atccctcaca ataagattta      2400
ttatataatc acaccatcta ccagttgaaa tgcagtgaga gcactttgtg agttgtatac      2460
caatgtttct cacgcttcac ttagcatgtg atactgttta tgctcagatg actgtcatta      2520
ggcctgctga catggatgct ctacaaaatg cgttggacaa caataatgtg agtgtggtat      2580
catttccatt gccctgatc gtggtaaaaa acatacatta atacatttgc aaatgtagcc       2640
taaccttatg gccatgtcag gtatctcttt tcttcacgga gactcccaca aatccatttc      2700
tcagatgcat tgatattgaa catgtatcaa atatgtgcca tagcaaggga gcgttgcttt      2760
gtatcgacag tacttttgcc tccctatca atcagaaggc actgactta ggcgctgacc        2820 tagttattca ttctgcaaca aagtacattg ctggacacaa cgatgtgagt tgatatactg      2880
aaccccatct cccctcatta aagttatgtg tttgcacatt gcactaacta gtacttcaac      2940
ttcccaggtt attggaggat gcgtcagtgg cagagatgag ttggtttcca agtccgtat      3000 ttatcaccat gtggttggtg gtgttctaaa cccggtaagt ttagattgtt aaagttttgt      3060
ttccatttat ttcatcttcc ttgcacaggt tgtatgtatt tacagattcc catagttaca      3120
agcttctatt tttataggta gaaaatcgtg taattttctt tagtagcata tgtttaggtt      3180
agaaaaataa tttgctttct ctgagtatca caaaccgcat ccagttctct gttacatgaa      3240
ctagaattct ggttctggaa aggaagaaat aggatatgtt ctgtgcactg caatatatat      3300
ctaatcatta atccggagct ttatgtcaca gactcacagg ccaggctacc actttatgaa      3360
atattccaaa ttatgcttgt ctcaaaatgg aatgactcat gttgtactct gttccaacgt      3420
tttcaaatca tgactaggat tctagttgcc cggacaccga ctaggtgatt aatcgtgact      3480
aggcattgac tagtcacgat tagttttgag ctagtcgaac ttatcaacaa cttgttccag      3540
gcaatatatt gcagtactat gccttattga ttgggtatat aaatgaattt tagcacacag      3600
atagagcaga agtaagacaa attaacacaa agttctaga                             3639
```

<210> SEQ ID NO 19
<211> LENGTH: 509
<212> TYPE: PRT
<213> ORGANISM: Zea mays

<400> SEQUENCE: 19

Met Ala Thr Val Ser Leu Thr Pro Gln Ala Val Phe Ser Thr Glu Ser

-continued

```
  1               5              10              15
Gly Gly Ala Leu Ala Ser Ala Thr Ile Leu Arg Phe Pro Pro Asn Phe
                20              25              30
Val Arg Gln Leu Ser Thr Lys Ala Arg Arg Asn Cys Ser Asn Ile Gly
                35              40              45
Val Ala Gln Ile Val Ala Ala Trp Ser Asp Cys Pro Ala Ala Arg
                50              55              60
Pro His Leu Gly Gly Gly Arg Arg Ala Arg Gly Val Ala Ser Ser
 65                 70              75                  80
His Ala Ala Ala Ser Ala Ala Ala Ala Ser Ala Ala Ala Glu
                85              90                  95
Val Ser Ala Ile Pro Asn Ala Lys Val Ala Gln Pro Ser Ala Val Val
                100             105             110
Leu Ala Glu Arg Asn Leu Leu Gly Ser Asp Ala Ser Leu Ala Val His
                115             120             125
Ala Gly Glu Arg Leu Gly Arg Arg Ile Ala Thr Asp Ala Ile Thr Thr
                130             135             140
Pro Val Asn Thr Ser Ala Tyr Trp Phe Asn Asn Ser Gln Glu Leu
145             150             155             160
Ile Asp Phe Lys Glu Gly Arg His Ala Ser Phe Glu Tyr Gly Arg Tyr
                165             170             175
Gly Asn Pro Thr Thr Glu Ala Leu Glu Lys Lys Met Ser Ala Leu Glu
                180             185             190
Lys Ala Glu Ser Thr Val Phe Val Ala Ser Gly Met Tyr Ala Ala Val
                195             200             205
Ala Met Leu Ser Ala Leu Val Pro Ala Gly His Ile Val Thr Thr
                210             215             220
Thr Asp Cys Tyr Arg Lys Thr Arg Ile Tyr Met Glu Asn Glu Leu Pro
225             230             235             240
Lys Arg Gly Ile Ser Met Thr Val Ile Arg Pro Ala Asp Met Asp Ala
                245             250             255
Leu Gln Asn Ala Leu Asp Asn Asn Val Ser Leu Phe Phe Thr Glu
                260             265             270
Thr Pro Thr Asn Pro Phe Leu Arg Cys Ile Asp Ile Glu His Val Ser
                275             280             285
Asn Met Cys His Ser Lys Gly Ala Leu Leu Cys Ile Asp Ser Thr Phe
                290             295             300
Ala Ser Pro Ile Asn Gln Lys Ala Leu Thr Leu Gly Ala Asp Leu Val
305             310             315             320
Ile His Ser Ala Thr Lys Tyr Ile Ala Gly His Asn Asp Val Ile Gly
                325             330             335
Gly Cys Val Ser Gly Arg Asp Glu Leu Val Ser Lys Val Arg Ile Tyr
                340             345             350
His His Val Gly Gly Val Leu Asn Pro Asn Ala Ala Tyr Leu Ile
                355             360             365
Leu Arg Gly Met Lys Thr Leu His Leu Arg Val Gln Cys Gln Asn Asp
                370             375             380
Thr Ala Leu Arg Met Ala Gln Phe Leu Glu Glu His Pro Lys Ile Ala
385             390             395             400
Arg Val Tyr Tyr Pro Gly Leu Pro Ser His Pro Glu His Ile Ala
                405             410             415
Lys Ser Gln Met Thr Gly Phe Gly Gly Val Val Ser Phe Glu Val Ala
                420             425             430
```

```
Gly Asp Phe Asp Ala Thr Arg Lys Phe Ile Asp Ser Val Lys Ile Pro
        435                 440                 445

Tyr His Ala Pro Ser Phe Gly Gly Cys Glu Ser Ile Ile Asp Gln Pro
        450                 455                 460

Ala Ile Met Ser Tyr Trp Asp Ser Lys Glu Gln Arg Asp Ile Tyr Gly
465                 470                 475                 480

Ile Lys Asp Asn Leu Ile Arg Phe Ser Ile Gly Val Glu Asp Phe Glu
                485                 490                 495

Asp Leu Lys Asn Asp Leu Val Gln Ala Leu Glu Lys Ile
            500                 505

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 20
aattcatgag tgca                                                         14

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 21
aatttgcact catg                                                         14

<210> SEQ ID NO 22
<211> LENGTH: 1350
<212> TYPE: DNA
<213> ORGANISM: Escherichia coli

<400> SEQUENCE: 22
atggctgaaa ttgttgtctc caaatttggc ggtaccagcg tagctgattt tgacgccatg        60
aaccgcagcg ctgatattgt gctttctgat gccaacgtgc gtttagttgt cctctcggct       120
tctgctggta tcactaatct gctggtcgct ttagctgaag gactggaacc tggcgagcga       180
ttcgaaaaac tcgacgctat ccgcaacatc cagtttgcca ttctggaacg tctgcgttac       240
ccgaacgtta tccgtgaaga gattgaacgt ctgctggaga acattactgt tctggcagaa       300
gcggcggcgc tggcaacgtc tccggcgctg acagatgagc tggtcagcca cggcgagctg       360
atgtcgaccc tgctgtttgt tgagatcctg cgcgaacgcg atgttcaggc acagtggttt       420
gatgtacgta aagtgatgcg taccaacgac cgatttggtc gtgcagagcc agatatagcc       480
gcgctggcgg aactggccgc gctgcagctg ctcccacgtc tcaatgaagg cttagtgatc       540
acccagggat ttatcggtag cgaaaataaa ggtcgtacaa cgacgcttgg ccgtggaggc       600
agcgattata cggcagcctt gctggcggag gctttacacg catctcgtgt tgatatctgg       660
accgacgtcc cgggcatcta caccaccgat ccacgcgtag tttccgcagc aaaacgcatt       720
gatgaaatcg cgtttgccga agcggcagag atggcaactt ttggtgcaaa agtactgcat       780
ccggcaacgt tgctacccgc agtacgcagc gatatcccgg tctttgtcgg ctccagcaaa       840
gacccacgcg caggtggtac gctggtgtgc aataaaactg aaaatccgcc gctgttccgc       900
```

```
gctctggcgc ttcgtcgcaa tcagactctg ctcactttgc acagcctgaa tatgctgcat    960
tctcgcggtt tcctcgcgga agttttcggc atcctcgcgc ggcataatat ttcggtagac   1020
ttaatcacca cgtcagaagt gagcgtggca ttaaccttg ataccaccgg ttcaacctcc   1080
actggcgata cgttgctgac gcaatctctg ctgatggagc tttccgcact gtgtcgggtg   1140
gaggtggaag aaggtctggc gctggtcgcg ttgattggca atgacctgtc aaaagcctgc   1200
gccgttggca agaggtatt cggcgtactg gaaccgttca acattcgcat gatttgttat   1260
ggcgcatcca gccataacct gtgcttcctg gtgcccggcg aagatgccga gcaggtggtg   1320
caaaaactgc atagtaattt gtttgagtaa                                    1350
```

<210> SEQ ID NO 23
<211> LENGTH: 449
<212> TYPE: PRT
<213> ORGANISM: Escherichia coli

<400> SEQUENCE: 23

```
Met Ala Glu Ile Val Val Ser Lys Phe Gly Gly Thr Ser Val Ala Asp
 1               5                  10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
        50                  55                  60

Asp Ala Ile Arg Asn Ile Gln Phe Ala Ile Leu Glu Arg Leu Arg Tyr
 65                  70                  75                  80

Pro Asn Val Ile Arg Glu Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285
```

```
Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Ala Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 24
gatccatggc tgaaattgtt gtctccaaat ttggcg                              36

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 25
gtaccgccaa atttggagac aacaatttca gccatg                              36

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 26
atggcagcca agatgcttgc attgttcgct                                     30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:
      Synthetic oligonucleotide
```

<400> SEQUENCE: 27
gaatgcagca ccaacaaagg gttgctgtaa                                              30

<210> SEQ ID NO 28
<211> LENGTH: 2123
<212> TYPE: DNA
<213> ORGANISM: Zea mays

<400> SEQUENCE: 28
tctagagcct attaccatct ctactcacgg gtcgtagagg tggtgaggta ggctacagct      60
ggtgacaatc ctactcaccc tttgtaatcc tctacggctc tacgcgtagt taattggtta     120
gatgtcaacc ccctctctaa gtggcagtag tgggcttggt tatacctgct agtgcctggg     180
gatgttctat ttttctagta gtgcttgatc aaacattgca tagtttgact tgggacaaac     240
tgtctgatat atatatatat ttttgggcag agggagcagt aagaacttat ttagaaatgt     300
aatcatttgt taaaaaggt ttaatttgc tgctttcttt cgttaatgtt gttttcacat       360
tagattttct ttgtgttata tacactggat acatacaaat tcagttgcag tagtctctta     420
atccacatca gctaggcata ctttagcaaa agcaaattac acaaatctag tgtgcctgtc     480
gtcacattct caataaactc gtcatgtttt actaaaagta ccttttcgaa gcatcatatt     540
aatccgaaaa cagttaggga agtctccaaa tctgaccaaa tgccaagtca tcgtccagct     600
tatcagcatc caactttcag tttcgcatgt gctagaaatt gttttcatc tacatggcca      660
tgttgactg catgcatcta taaataggac ctagacgatc aatcgcaatc gcatatccac      720
tattctctag gaagcaaggg aatcacatcg ccatggcagc caagatgttt gcattgtttg     780
cgctcctagc tctttgtgca accgccacta gtgctaccca tcccagggg cacttgtcac      840
cactactgat gccattggct accatgaacc catggatgca gtactgcatg aagcaacagg     900
gggttgccaa cttgttagcg tggccgaccc tgatgctgca gcaactgttg gcctcaccgc     960
ttcagcagtg ccagatgcca atgatgatgc cgggtatgat gccaccgatg acgatgatgc    1020
cgatgccgag tatgatgcca tcgatgatgg tgccgactat gatgtcacca atgacgatgg    1080
ctagtatgat gccgccgatg atgatgccaa gcatgatttc accaatgacg atgccgagta    1140
tgatgccttc gatgataatg ccgaccatga tgtcaccaat gattatgccg agtatgatgc    1200
caccaatgat gatgccgagc atggtgtcac caatgatgat gccaaacatg atgacagtgc    1260
cacaatgtta ctctggttct atctcacaca ttatacaaca acaacaatta ccattcatgt    1320
tcagccccac agccatggcg atcccaccca tgttcttaca gcagcccttt gttggtgctg    1380
cattctagat ctagatataa gcatttgtgt agtacccaat aatgaagtcg gcatgccatc    1440
gcatacgact cattgtttag gaataaaaca agctaataat gacttttctc tcattataac    1500
ttatatctct ccatgtctgt tgtgtgtttt gtaatgtctg ttaatcttag tagattatat    1560
tgtatatata accatgtatt ctctccattc caaattatag gtcttgcatt tcaagataaa    1620
tagttttaac catacctaga cattatgtat atataggcgg cttaacaaaa gctatgtact    1680
cagtaaaatc aaaacgactt acaatttaaa atttagaaag tacatttta ttaatagact     1740
aggtgagtac ttgtgcgttg caacgggaac atataataac ataataactt atatacaaaa    1800
tgtatcttat attgttataa aaaatatttc ataatccatt tgtaatccta gtcatacata    1860
aattttgtta ttttaatta gttgtttcac tactacattg caaccattag tatcatgcag     1920
acttcgatat atgccaagat ttgcatggtc tcatcattga agagcacatg tcacacctgc    1980

```
cggtagaagt tctctcgtac attgtcagtc atcaggtacg caccaccata cacgcttgct    2040
taaacaaaaa aacaagtgta tgtgtttgcg aagagaatta agacaggcag acacaaagct    2100
acccgacgat ggcgagtcgg tca                                            2123
```

<210> SEQ ID NO 29
<211> LENGTH: 211
<212> TYPE: PRT
<213> ORGANISM: Zea mays

<400> SEQUENCE: 29

```
Met Ala Ala Lys Met Phe Ala Leu Phe Ala Leu Leu Ala Leu Cys Ala
 1               5                  10                  15
Thr Ala Thr Ser Ala Thr His Ile Pro Gly His Leu Ser Pro Leu Leu
             20                  25                  30
Met Pro Leu Ala Thr Met Asn Pro Trp Met Gln Tyr Cys Met Lys Gln
         35                  40                  45
Gln Gly Val Ala Asn Leu Leu Ala Trp Pro Thr Leu Met Leu Gln Gln
     50                  55                  60
Leu Leu Ala Ser Pro Leu Gln Gln Cys Gln Met Pro Met Met Met Pro
 65                  70                  75                  80
Gly Met Met Pro Pro Met Thr Met Met Pro Met Pro Ser Met Met Pro
                 85                  90                  95
Ser Met Met Val Pro Thr Met Met Ser Pro Met Thr Met Ala Ser Met
                100                 105                 110
Met Pro Pro Met Met Met Pro Ser Met Ile Ser Pro Met Thr Met Pro
            115                 120                 125
Ser Met Met Pro Ser Met Ile Met Pro Thr Met Met Ser Pro Met Ile
        130                 135                 140
Met Pro Ser Met Met Pro Pro Met Met Met Pro Ser Met Val Ser Pro
145                 150                 155                 160
Met Met Met Pro Asn Met Met Thr Val Pro Gln Cys Tyr Ser Gly Ser
                165                 170                 175
Ile Ser His Ile Ile Gln Gln Gln Leu Pro Phe Met Phe Ser Pro
            180                 185                 190
Thr Ala Met Ala Ile Pro Pro Met Phe Leu Gln Gln Pro Phe Val Gly
        195                 200                 205
Ala Ala Phe
    210
```

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence:
    Synthetic oligonucleotide

<400> SEQUENCE: 30

```
atgaaccctt ggatgca                                                     17
```

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:
    Synthetic oligonucleotide

<400> SEQUENCE: 31

```
cccacagcaa tggcgat                                              17

<210> SEQ ID NO 32
<211> LENGTH: 639
<212> TYPE: DNA
<213> ORGANISM: Zea mays

<400> SEQUENCE: 32
ccatggcagc caagatgttt gcattgtttg cgctcctagc tctttgtgca accgccacta    60
gtgctaccca tatcccaggg cacttgtcac cactactgat gccattggct accatgaacc   120
cttggatgca gtactgcatg aagcaacagg gggttgccaa cttgttagcg tggccgaccc   180
tgatgctgca gcaactgttg gcctcaccgc ttcagcagtg ccagatgcca atgatgatgc   240
cgggtatgat gccaccgatg acgatgatgc cgatgccgag tatgatgcca tcgatgatgg   300
tgccgactat gatgtcacca atgacgatgg ctagtatgat gccgccgatg atgatgccaa   360
gcatgatttc accaatgacg atgccgagta tgatgccttc gatgataatg ccgaccatga   420
tgtcaccaat gattatgccg agtatgatgc caccaatgat gatgccgagc atggtgtcac   480
caatgatgat gccaaacatg atgacagtgc cacaatgtta ctctggttct atctcacaca   540
ttatacaaca acaacaatta ccattcatgt tcagccccac agcaatggcg atcccaccca   600
tgttcttaca gcagcccttt gttggtgctg cattctaga                         639

<210> SEQ ID NO 33
<211> LENGTH: 211
<212> TYPE: PRT
<213> ORGANISM: Zea mays

<400> SEQUENCE: 33

Met Ala Ala Lys Met Phe Ala Leu Phe Ala Leu Leu Ala Leu Cys Ala
  1               5                  10                  15

Thr Ala Thr Ser Ala Thr His Ile Pro Gly His Leu Ser Pro Leu Leu
             20                  25                  30

Met Pro Leu Ala Thr Met Asn Pro Trp Met Gln Tyr Cys Met Lys Gln
         35                  40                  45

Gln Gly Val Ala Asn Leu Leu Ala Trp Pro Thr Leu Met Leu Gln Gln
     50                  55                  60

Leu Leu Ala Ser Pro Leu Gln Gln Cys Gln Met Pro Met Met Met Pro
 65                  70                  75                  80

Gly Met Met Pro Pro Met Thr Met Met Pro Met Pro Ser Met Met Pro
                 85                  90                  95

Ser Met Met Val Pro Thr Met Met Ser Pro Met Thr Met Ala Ser Met
            100                 105                 110

Met Pro Pro Met Met Met Pro Ser Met Ile Ser Pro Met Thr Met Pro
        115                 120                 125

Ser Met Met Pro Ser Met Ile Met Pro Thr Met Met Ser Pro Met Ile
    130                 135                 140

Met Pro Ser Met Met Pro Pro Met Met Met Pro Ser Met Val Ser Pro
145                 150                 155                 160

Met Met Met Pro Asn Met Met Thr Val Pro Gln Cys Tyr Ser Gly Ser
                165                 170                 175

Ile Ser His Ile Ile Gln Gln Gln Leu Pro Phe Met Phe Ser Pro
            180                 185                 190

Thr Ala Met Ala Ile Pro Pro Met Phe Leu Gln Gln Pro Phe Val Gly
        195                 200                 205
```

Ala Ala Phe
   210

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 34
ctagcccggg tac                                                          13

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 35
ctaggtaccc ggg                                                          13

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 36
ccacttcatg acccatatcc cagggcactt                                        30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 37
ttctatctag aatgcagcac caacaaaggg                                        30

<210> SEQ ID NO 38
<211> LENGTH: 579
<212> TYPE: DNA
<213> ORGANISM: Zea mays

<400> SEQUENCE: 38
tcatgaccca tatcccaggg cacttgtcac cactactgat gccattggct accatgaacc       60
cttggatgca gtactgcatg aagcaacagg gggttgccaa cttgttagcg tggccgaccc      120
tgatgctgca gcaactgttg gcctcaccgc ttcagcagtg ccagatgcca atgatgatgc      180
cgggtatgat gccaccgatg acgatgatgc cgatgccgag tatgatgcca tcgatgatgg      240
tgccgactat gatgtcacca atgacgatgg ctagtatgat gccgccgatg atgatgccaa      300
gcatgatttc accaatgacg atgccgagta tgatgccttc gatgataatg ccgaccatga      360
tgtcaccaat gattatgccg agtatgatgc caccaatgat gatgccgagc atggtgtcac      420
caatgatgat gccaaacatg atgacagtgc cacaatgtta ctctggttct atctcacaca      480

```
ttatacaaca acaacaatta ccattcatgt tcagccccac agcaatggcg atcccaccca    540
tgttcttaca gcagccettt gttggtgctg cattctaga                            579

<210> SEQ ID NO 39
<211> LENGTH: 191
<212> TYPE: PRT
<213> ORGANISM: Zea mays

<400> SEQUENCE: 39

Met Thr His Ile Pro Gly His Leu Ser Pro Leu Leu Met Pro Leu Ala
  1               5                  10                  15

Thr Met Asn Pro Trp Met Gln Tyr Cys Met Lys Gln Gln Gly Val Ala
             20                  25                  30

Asn Leu Leu Ala Trp Pro Thr Leu Met Leu Gln Gln Leu Leu Ala Ser
         35                  40                  45

Pro Leu Gln Gln Cys Gln Met Pro Met Met Pro Gly Met Met Pro
     50                  55                  60

Pro Met Thr Met Met Pro Met Pro Ser Met Met Pro Ser Met Met Val
 65                  70                  75                  80

Pro Thr Met Met Ser Pro Met Thr Met Ala Ser Met Met Pro Pro Met
                 85                  90                  95

Met Met Pro Ser Met Ile Ser Pro Met Thr Met Pro Ser Met Met Pro
            100                 105                 110

Ser Met Ile Met Pro Thr Met Met Ser Pro Met Ile Met Pro Ser Met
            115                 120                 125

Met Pro Pro Met Met Met Pro Ser Met Val Ser Pro Met Met Met Pro
        130                 135                 140

Asn Met Met Thr Val Pro Gln Cys Tyr Ser Gly Ser Ile Ser His Ile
145                 150                 155                 160

Ile Gln Gln Gln Leu Pro Phe Met Phe Ser Pro Thr Ala Met Ala
                165                 170                 175

Ile Pro Pro Met Phe Leu Gln Gln Pro Phe Val Gly Ala Ala Phe
            180                 185                 190

<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 40
ctagaagcct cggcaacgtc agcaacggcg gaagaatccg gtg                       43

<210> SEQ ID NO 41
<211> LENGTH: 43
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 41
catgcaccgg attcttccgc cgttgctgac gttgccgagg ctt                       43

<210> SEQ ID NO 42
<211> LENGTH: 55
<212> TYPE: DNA
```

```
<213> ORGANISM: Artificial Sequence
<220> FEATURE:
<223> OTHER INFORMATION: Description of Artificial Sequence:
      Synthetic oligonucleotide

<400> SEQUENCE: 42
gatcccatgg cgccccttaa gtccaccgcc agcctccccg tcgcccgccg ctcct          55

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 43
ctagaggagc ggcgggcgac ggggaggctg gcggtggact taagggggcgc catgg         55

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 44
catggcgccc accgtgatga tggcctcgtc ggccaccgcc gtcgctccgt tccaggggc      59

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 45
ttaagcccct ggaacggagc gacggcggtg gccgacgagg ccatcatcac ggtgggcgc      59

<210> SEQ ID NO 46
<211> LENGTH: 75
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 46
catggctggc ttccccacga ggaagaccaa caatgacatt acctccattg ctagcaacgg     60
tggaagagta caatg                                                     75

<210> SEQ ID NO 47
<211> LENGTH: 75
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 47
catgcattgt actcttccac cgttgctagc aatggaggta atgtcattgt tggtcttcct     60 cgtgggggaag ccagc                                                    75
```

```
<210> SEQ ID NO 48
<211> LENGTH: 90
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 48
catggcttcc tcaatgatct cctccccagc tgttaccacc gtcaaccgtg ccggtgccgg      60
catggttgct ccattcaccg gcctcaaaag                                      90

<210> SEQ ID NO 49
<211> LENGTH: 90
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 49
catgcttttg aggccggtga atggagcaac catgccggca ccggcacggt tgacggtggt      60
aacagctggg gaggagatca ttgaggaagc                                      90

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 50
gactatccat ggcacattgt actcttccac c                                    31

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 51
tactaaccat ggcttcctca                                                 20

<210> SEQ ID NO 52
<211> LENGTH: 12
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 52
ggccatggcc gc                                                         12

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 53
```

```
gaaaccatgg ccagtgtgat tgcgcaggca                                        30
```

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 54

```
gaaaggtacc ttacaacaac tgtgccagc                                         29
```

<210> SEQ ID NO 55
<211> LENGTH: 1494
<212> TYPE: DNA
<213> ORGANISM: Glycine max
<220> FEATURE:
<221> NAME/KEY: unsure
<222> LOCATION: (1461)
<223> OTHER INFORMATION: n = A, C, G, or T
<220> FEATURE:
<221> NAME/KEY: unsure
<222> LOCATION: (1464)
<223> OTHER INFORMATION: n = A, C, G, or T
<220> FEATURE:
<221> NAME/KEY: unsure
<222> LOCATION: (1465)
<223> OTHER INFORMATION: n = A, C, G, or T

<400> SEQUENCE: 55

```
atttgcagca caaaaagttg ttgaagtaaa tgccttggcc aaggcattgt ctggacagaa        60
ggatgaggtt ttcttttctg ctaatgctgc tgccttggct tcaaggaagt cctccccaag       120
ggtgataaat gaggctgtcc aaaaagccgc tgctgctctg aagggctctg atcatcggag       180
ggccacaaat gttagtgcca ggttggatgc tcaacagaag aaattgaatc tttctgttct       240
tccaacaact acaattggat ctttccctca aactgccgat cttagaagrg twcgycgtga       300
attcaaggct aacaagatct ccgaggaaga gtatgthaag tcaattaagg aggaaattcg       360
caaagttgtt garcttcaag aagagcttga tattgatgtt cttgttcatg agaaccaga       420
gagaaatgat atggttgagt acttcggtga rcaattgtca ggctttgcct tcacygttaa       480
tgggtgggtg caatcctatg gttcccgttg ygtgaagcca ccratcatct atggtgatgt       540
gagccgccca agccaatga cygtcttctg gtcatctctg gctcagagct ttaccaagcg       600
cccaatgaag ggaatgctta ccggtcctgt taccattctc aactggkcct ttgtwagaaa       660
tgaccaacct agatctgaga ccacctacca gattgctttg ctatcaagg acgaagtgga       720
ggaccttgaa aaggctggca tcactgttat ccaaattgat gaagctgctt tgagagaggg       780
tctgccactg rggaaatcag aacaagctca ctacttggac tgggctgtcc atgccttcag       840
aatcaccaat gttggtgtgc aggataccac tcagatccac acccacatgt gctactccaa       900
cttcaacgac atcatccact ccatcatcga catggacgct gatgttatca ccattgagaa       960
ctctcgctcc gatgagaagc tcctgtcagt cttccgtgaa ggtgtgaagt atggtgctgg      1020
aattgsccct ggtgtctatg acatccactc cccaagaata ccaccaactg aagaaatcgc      1080
tgacagaatc aataagatgc tggcagtgct cgagaagaac atcttgtggg tcaaccctga      1140
ctgtggtctc aagacccgca agtacactga agtgaagccc gccctcacaa acatggttgc      1200
cgcagcaaaa ctcatccgta acgaacttgc caagtgaatg gtataagaaa gtagaatcta      1260
caagttcatt ggttctgctt ttataataca ccaaagaaaa attttctata ttgggttgtt      1320
```

```
tcaataaccg tgtgtggaat atttagatgt tttagcatgc tctgtgagca attgattctt    1380
cctcaacccc tctcccctta tttttcccaa ctcctgtttt ccctaatgaa tgttgtatct    1440
ttgctttgcc gcaatcctta nttnngatat gaaatattac cagttttgtg caaa          1494
```